(12) United States Patent
Lin et al.

(10) Patent No.: US 7,947,652 B2
(45) Date of Patent: May 24, 2011

(54) COMPOSITIONS AND METHODS FOR MODULATING PGC-1α TO TREAT HUNTINGTON'S DISEASE

(75) Inventors: Jiandie Lin, Ann Arbor, MI (US); Bruce M. Spiegelman, Waban, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 14 days.

(21) Appl. No.: 11/660,986

(22) PCT Filed: Sep. 6, 2005

(86) PCT No.: PCT/US2005/031715
§ 371 (c)(1),
(2), (4) Date: Feb. 4, 2008

(87) PCT Pub. No.: WO2006/026785
PCT Pub. Date: Mar. 9, 2006

(65) Prior Publication Data
US 2009/0005314 A1 Jan. 1, 2009

Related U.S. Application Data

(60) Provisional application No. 60/607,412, filed on Sep. 3, 2004.

(51) Int. Cl.
*A01N 37/18* (2006.01)
*A61K 38/00* (2006.01)
(52) U.S. Cl. ............ 514/17.7; 514/1; 514/1.1; 514/21.2
(58) Field of Classification Search ........................ None
See application file for complete search history.

(56) References Cited

U.S. PATENT DOCUMENTS 6,525,178 B2 2/2003 Spiegelman et al.

FOREIGN PATENT DOCUMENTS

WO WO-02/062297 8/2002
WO WO-2004/000313 12/2003

OTHER PUBLICATIONS

Chaturverdi et al., 2009, Human Mol. Genetics, vol. 18, No. 16, pp. 3048-3065.*
Aoki, T. T., "Metabolic Adaptations to Starvation, Semistarvation, and Carbohydrate Restriction," Prog Clin Biol Res 67:161-177 (1981).
Baar et al., "Adaptations of skeletal muscle to exercise: rapid increase in the transcriptional coactivator PGC-1," FASEB Journal, 1879-1886 (2002).
Bouillaud, F. et al., "Molecular approach to thermogenesis in brown adipose tissue: cDNA cloning of the mitochondrial uncoupling protein," Proc Natl Acad Sci USA 82:445-448 (1985).
Carling, D., "The AMP-activated protein kinase cascade—a unifying system for energy control," Trends Biochem Sd 29:18-24 (2004).

Croniger, C. et al., "Role of the Isoforms of CCAAT/Enhancer-binding Protein in the Initiation of Phosphoenolpyruvat Carboxykinase (GTP) Gene Transcription at Birth," J Biol Chem 272:26306-26312 (1997).
Croniger, C. et al., "C/EBP and the Control of Phosphoenolpyruvate Carboxykinase Gene Transcription in the Liver," J Biol Chem 273:31629-31632 (1998).
Fan, M., et al., "Suppression of mitochondrial respiration through recruitment of p160 myb binding protein to PGC-1α: modulation by p38 MAPK," Genes Dev 18:278-289 (2004).
Goto et al., "cDNA Cloning and mRNA Analysis of PGC-1 in Epitrochlearis Muscle in Swimming-Exercised Rats," Biochem Biophys Res Commun 274, 350-354 (2000).
Hanson, R. W., and Reshef, L., "Regulation of Phosphoenolpyruvate Carboxykinase (GTP) Gene Experssion," Annu Rev Biochem 66:581-611 (1997).
Herzig, S., et al., "CREB regulates hepatic gluconeogenesis through the coactivator PGC-1," Nature 413:179-183 (2001).
Horton, J. D., et al., "SREBPs: activators of the complete program of cholesterol and fatty acid synthesis in the liver," J Clin Invest 109:1125-1 131 (2002).
Jacobsson, A., et al., Mitochondrial Uncoupling Protein from Mouse Brown Fat, J Biol Chem 260:16250-16254 (1985).
Kelly, D. P., and Scarpulla, R. C., "Transcriptional regulatory circuits controlling mitochondrial biogenesis and function," Genes Dev 18:357-368 (2004).
Lehman et al, "Peroxisome proliferator-activated receptor γ coactivator-1 promotes cardiac mitochondrial biogenesis," J Clin Invest 106:847-856 (2000).
Lehman et al., "Transcriptional Activation of Energy Metabolic Switches in the Developing and Hypertrophied Heart," Clin. Exp. Pharmacol. Phys. 29:339-345 (2002).
Lewandoski, M. et al., "Zp3-cre, a transgenic mouse line for the activation or inactivation of *loxP*-flanked target genes specifically in the female germ line," Curr Biol 7, 148-151 (1997).
Lin et al., "Transcriptional co-activator PGC-1α drives the formation of slow-twitch muscle fibres," Nature 418:797-801 (2002).
Liu, S. et al., Hypoglycemia and impaired hepatic glucose production in mice with a deletion of the C/EBPβ gene, J Clin Invest 103:207-213 (1999).
Miyake, K., et al., "Hyperinsulinemia, glucose intolerance, and dyslipidemia induced by acute inhibition of phosphoinositide 3-kinase signaling in the liver," J Clin Invest 110:1483-1491 (2002).
Mootha et al., "PGC-1α-responsive genes involved in oxidative phosphorylation are coordinately downregulated in human diabetes," Nat. Genet., 34:267-273 (2003).
Moyes, C.D., "Controlling muscle mitochondrial content," Exp. Biol. 206:4385-4391 (2003).
Park, E. A. et al., "Relative Roles of CCAAT/Enhancer-binding Protein β and cAMP Regulatory Element-binding Protein in Controlling Transcription of the Gene for Phosphoenolpyruvate Carboxykinase (GTP)," J Biol Chem 268:613-619 (1993).

(Continued)

*Primary Examiner* — Olga N Chernyshev
(74) *Attorney, Agent, or Firm* — Foley Hoag, LLP

(57) ABSTRACT

The present invention provides methods for modulating mitochondrial function, modulating lesion formation in the brain, modulating neurite growth, modulating neuronal degeneration, and treating and preventing neurological diseases or disorders comprising modulating the expression or activity of PGC-1α. The present invention also provides an animal, e.g., transgenic mouse, in which the PGC-1α gene is misexpressed. Methods for identifying compounds which are capable of treating or preventing a neurological disease or disorder are also described.

8 Claims, 10 Drawing Sheets

OTHER PUBLICATIONS

Patti, M. et al., "Coordinated reduction of genes of oxidative metabolism in humans with insulin resistance and diabetes: Potential role of PGC1 and NRF1," PNAS 100:8466-8471 (2003).

Pilkis, S. J., and Granner, D. K., "Molecular Physiology of the Regulation of Hepatic Gluconeogenesis and Glycolysis," Annu Rev Physiol 54:885-909 (1992).

Portilla, D., "Energy Metabolism and Cytotoxicity," Seminars Nephrol. 23:432-438 (2003).

Puigserver et al. A Cold-Inducible Coactivator of Nuclear Receptors Linked to Adaptive Thermogenesis, Cell 92:829-839 (1998).

Puigserver, P., and Spiegelman, B.M., "Peroxisome Proliferator-Activated Receptor-γ Coactivator 1α (PGC-1α): Transcriptional Coactivator and Metabolic Regulator," Endocrine Rev 24:78-90 (2003).

Rhee, J., et al., "Regulation of hepatic fasting response by PPARγ coactivator-1α (PGC10): Requirement for hepatocyte nuclear factor 4α in gluconeogenesis," PNAS 100:4012-4017 (2003).

Roesler, W. J., "The Role of C/EBP in Nutrient and Hormonal Regulation of Gene Expression," Annu Rev. Nutr 21:141-165 (2001).

Schilling, G. et al., "Intranuclear inclusions and neuritic aggregates in transgenic mice expressing a mutant N-terminal fragment of huntingtin," Human Mol. Genet. 8(3):397-407 (1999).

Schon, E.A. and Manfredi, G., "Neuronal degeneration and mitochondrial dysfunction," J. Clin. Invest. 111(3):303-312 (2003).

Shin, D. J., et al., "PGC-1α Activates CYP7A1 and Bile Acid Biosynthesis," J Biol Chem 278:50047-50052 (2003).

St-Pierre et al., "Bioenergetic Analysis of Peroxisome Proliferator-activated Receptor γ Coactivators 1α and 1β (PGC-1α and PGC-1β) in Muscle Cells," J Biol Chem 278:26597-26603 (2003).

Tritos et al., "Characterization of the peroxisome proliferator activated receptor coactivator 1 alpha (PGC 1α) expression in the murine brain," Brain Res. 961:255-260 (2003).

Wu, Z., "Mechanisms Controlling Mitochondrial Biogenesis and Respiration through the Thermogenic Coactivator PGC-1," Cell 98:115-124 (1999).

Yoon et al., "Control of hepatic gluconeogenesis through the transcriptional coactivator PGC-1," Nature 413:131-138 (2001).

Presentation "Control of Lipid and Energy Homeostasis Through Transcriptional Coactivation" presented at Northwestern Medical School on Jun. 8, 2004 (9 pages).

Houten et al., "PGC-1α: Turbocharging Mitochondria," Cell, 119(1):5-7 (2004) XP-002551130.

Koo et al., "PGC-1 promotes insulin resistance in liver through PPAR-α-dependent induction of TRB-3," Nature Medicine, 10(5):530-534 (2004).

Leone et al., "PGC-1α Deficiency Causes Multi-System Energy Metabolic Derangements: Muscle Dysfunction, Abnormal Weight Control and Hepatic Steatosis," PloS Biology, 3(4):672-687 (2005).

Lin et al., "Defects in Adaptive Energy Metabolism with CNS-Linked Hyperactivity in PGC-1α Null Mice," Cell, 119(1):121-135 (2004).

Lin et al., "Metabolic control through the PGC-1 family of transcription coactivators," Cell Metabolism, 1(6):361-370 (2005).

Supplemental European Search Report dated Oct. 30, 2009 from Application No. 05809824.5.

GenBank Accession No. NM_013261 (GI: 29570796) dated Sep. 24, 2006.

GenBank Accession No. NM_008904 (GI: 6679432) dated Oct. 14, 2007.

* cited by examiner

SEQUENCE LISTING

<160> NUMBER OF SEQ ID NOS: 47

<210> SEQ ID NO 1
<211> LENGTH: 6317

```
<212> TYPE: DNA
<213> ORGANISM: Homo sapiens

<400> SEQUENCE: 1
tagtaagaca ggtgccttca gttcactctc agtaaggggc tggttgcctg catgagtgtg      60
tgctctgtgt cactgtggat tggagttgaa aaagcttgac tggcgtcatt caggagctgg     120
atggcgtggg acatgtgcaa ccaggactct gagtctgtat ggagtgacat cgagtgtgct     180
gctctggttg gtgaagacca gcctctttgc ccagatcttc ctgaacttga tctttctgaa     240
ctagatgtga acgacttgga tacagacagc tttctgggtg gactcaagtg gtgcagtgac     300
caatcagaaa taatatccaa tcagtacaac aatgagcctt caaacatatt tgagaagata     360
gatgaagaga atgaggcaaa cttgctagca gtcctcacag agacactaga cagtctccct     420
gtggatgaag acggattgcc ctcatttgat gcgctgacag atggagacgt gaccactgac     480
aatgaggcta gtccttcctc catgcctgac ggcaccccte cacccaggag ggcagaagag     540
ccgtctctac ttaagaagct cttactggca ccagccaaca ctcagctaag ttataatgaa     600
tgcagtggtc tcagtaccca gaaccatgca aatcacaatc acaggatcag aacaaaccct     660
gcaattgtta agactgagaa ttcatggagc aataaagcga agagtatttg tcaacagcaa     720
aagccacaaa gacgtccctg ctcggagctt ctcaaatatc tgaccacaaa cgatgaccct     780
cctcacacca aacccacaga gaacagaaac agcagcagag acaaatgcac ctccaaaaag     840
aagtcccaca cacagtcgca gtcacaacac ttacaagcca aaccaacaac tttatctctt     900
cctctgaccc cagagtcacc aaatgacccc aagggttccc catttgagaa caagactatt     960
gaacgcacct taagtgtgga actctctgga actgcaggcc taactccacc caccactcct    1020
cctcataaag ccaaccaaga taaccctttt agggcttctc caaagctgaa gtcctcttgc    1080
aagactgtgg tgccaccacc atcaaagaag cccaggtaca gtgagtcttc tggtacacaa    1140
ggcaataact ccaccaagaa agggccggag caatccgagt tgtatgcaca actcagcaag    1200
tcctcagtcc tcactggtgg acacgaggaa aggaagacca gcggcccag tctgcggctg    1260
tttggtgacc atgactattg ccagtcaatt aattccaaaa cagaaatact cattaatata    1320
tcacaggagc tccaagactc tagacaacta gaaaataaag atgtctcctc tgattggcag    1380
gggcagattt gttcttccac agattcagac cagtgctacc tgagagagac tttggaggca    1440
agcaagcagg tctctccttg cagcacaaga aaacagctcc aagaccagga aatccgagcc    1500
gagctgaaca agcacttcgg tcatcccagt caagctgttt ttgacgacga agcagacaag    1560
accggtgaac tgagggacag tgatttcagt aatgaacaat tctccaaact acctatgttt    1620
ataaattcag gactagccat ggatggcctg tttgatgaca cgcaagatga agtgataaa     1680
ctgagctacc cttgggatgg cacgcaatcc tattcattgt tcaatgtgtc tccttcttgt    1740
tcttctttta actctccatg tagagattct gtgtcaccac ccaaatcctt atttcttcaa    1800
agaccccaaa ggatgcgctc tcgttcaagg tcctttttctc gacacaggtc gtgttcccga    1860
tcaccatatt ccaggtcaag atcaaggtct ccaggcagta gatcctcttc aagatcctgc    1920
tattactatg agtcaagcca ctacagacac cgcacgcacc gaaattctcc cttgtatgtg    1980
agatcacgtt caagatcgcc ctacagccgt cggcccaggt atgacagcta cgaggaatat    2040
cagcacgaga ggctgaagag gaagaatat cgcagagagt atgagaagcg agagtctgag    2100
agggccaagc aaagggagag gcagaggcag aaggcaattg aagagcgccg tgtgatttat    2160
gtcggtaaaa tcagacctga cacaacacgg acagaactga gggaccgttt tgaagttttt    2220
ggtgaaattg aggagtgcac agtaaatctg cgggatgatg agacagcta tggtttcatt    2280
```

```
acctaccgtt ataccgtgtga tgcttttgct gctcttgaaa atggatacac tttgcgcagg   2340
tcaaacgaaa ctgactttga gctgtacttt tgtggacgca agcaattttt caagtctaac   2400
tatgcagacc tagattcaaa ctcagatgac tttgaccctg cttccaccaa gagcaagtat   2460
gactctctgg attttgatag tttactgaaa gaagctcaga gaagcttgcg caggtaacat   2520
gttccctagc tgaggatgac agagggatgg cgaatacctc atgggacagc gcgtccttcc   2580
ctaaagacta ttgcaagtca tacttaggaa tttctcctac tttacactct ctgtacaaaa   2640
acaaaacaaa acaacaacaa tacaacaaga acaacaacaa caataacaac aatggtttac   2700
atgaacacag ctgctgaaga ggcaagagac agaatgatat ccagtaagca catgtttatt   2760
catgggtgtc agctttgctt ttcctggagt ctcttggtga tggagtgtgc gtgtgtgcat   2820
gtatgtgtgt gtgtatgtat gtgtgtggtg tgtgtgcttg gtttagggga agtatgtgtg   2880
ggtacatgtg aggactgggg gcacctgacc agaatgcgca agggcaaacc atttcaaatg   2940
gcagcagttc catgaagaca cgcttaaaac ctagaacttc aaaatgttcg tattctattc   3000
aaaaggaaat atatatatat atatatatat atatatatat atatataaat taaaaaggaa   3060
agaaaactaa caaccaacca accaaccaac caaccacaaa ccaccctaaa atgacagccg   3120
ctgatgtctg ggcatcagcc tttgtactct gttttttttaa gaaagtgcag aatcaacttg   3180
aagcaagctt tctctcataa cgtaatgatt atatgacaat cctgaagaaa ccacaggttc   3240
catagaacta atatcctgtc tctctctctc tctctctctc tctcttttt ttttcttttt   3300 ccttttgcca tggaatctgg gtgggagagg atactgcggg caccagaatg ctaaagtttc   3360
ctaacatttt gaagtttctg tagttcatcc ttaatcctga cacccatgta aatgtccaaa   3420
atgttgatct tccactgcaa atttcaaaag ccttgtcaat ggtcaagcgt gcagcttgtt   3480
cagcggttct ttctgaggag cggacaccgg gttacattac taatgagagt tgggtagaac   3540
tctctgagat gtgttcagat agtgtaattg ctacattctc tgatgtagtt aagtatttac   3600
agatgttaaa tggagtattt ttattttatg tatatactat acaacaatgt tcttttttgt   3660
tacagctatg cactgtaaat gcagcctttct tttcaaaact gctaaatttt tcttaatcaa   3720
gaatattcaa atgtaattat gaggtgaaac aattattgta cactaacata tttagaagct   3780
gaacttactg cttatatata tttgattgta aaaacaaaaa gacagtgtgt gtgtctgttg   3840
agtgcaacaa gagcaaaatg atgctttccg cacatccatc ccttaggtga gcttcaatct   3900
aagcatcttg tcaagaaata tcctagtccc ctaaaggtat taaccacttc tgcgatattt   3960
ttccacattt tcttgtcgct tgttttttctt tgaagtttta tacactggat ttgttagggg   4020
aatgaaattt tctcatctaa aattttttcta gaagatatca tgattttatg taaagtctct   4080
caatgggtaa ccattaagaa atgttttat tttctctatc aacagtagtt ttgaaactag   4140
aagtcaaaaa tctttttaaa atgctgtttt gttttaattt ttgtgatttt aatttgatac   4200
aaaatgctga ggtaataatt atagtatgat ttttacaata attaatgtgt gtctgaagac   4260
tatctttgaa gccagtattt ctttcccttg gcagagtatg acgatggtat ttatctgtat   4320
tttttacagt tatgcatcct gtataaatac tgatatttca ttcctttgtt tactaaagag   4380
acatatttat cagttgcaga tagcctattt attataaaatt atgagatgat gaaaataata   4440
aagccagtgg aaatttctaa cctaggatgc atgacaattg tcaggttgga gtgtaagtgc   4500
ttcatttggg aaattcagct tttgcagaag cagtgtttct acttgcacta gcatggcctc   4560
tgacgtgacc atggtgttgt tcttgatgac attgcttctg ctaaatttaa taaaaacttc   4620
agaaaaacct ccattttgat catcaggatt tcatctgagt gtggagtccc tggaatggaa   4680
```

-continued

```
ttcagtaaca tttggagtgt gtattcaagt ttctaaattg agattcgatt actgtttggc    4740
tgacatgact tttctggaag acatgataca cctactactc aattgttctt ttcctttctc    4800
tcgcccaaca cgatcttgta agatggattt cacccccagg ccaatgcagc taattttgat    4860
agctgcattc atttatcacc agcatattgt gttctgagtg aatccactgt ttgtcctgtc    4920
ggatgcttgc ttgatttttt ggcttcttat ttctaagtag atagaaagca ataaaaatac    4980
tatgaaatga agaacttgt tcacaggttc tgcgttacaa cagtaacaca tctttaatcc     5040
gcctaattct tgttgttctg taggttaaat gcaggtattt taactgtgtg aacgccaaac    5100
taaagtttac agtctttctt tctgaatttt gagtatcttc tgttgtagaa taataataaa    5160
aagactatta agagcaataa attattttta agaaatcgag atttagtaaa tcctattatg    5220
tgttcaagga ccacatgtgt tctctatttt gcctttaaat ttttgtgaac caattttaaa    5280
tacattctcc tttttgccct ggattgttga catgagtgga atacttggtt tcttttctta    5340
cttatcaaaa gacagcacta cagatatcat attgaggatt aatttatccc cctacccccc    5400
agcctgacaa atattgttac catgaagata gttttcctca atggacttca aattgcatct    5460
agaattagtg gagcttttgt atcttctgca gacactgtgg gtagcccatc aaaatgtaag    5520
ctgtgctcct ctcatttta tttttatttt tttgggagag aatatttcaa atgaacacgt     5580
gcaccccatc atcactggag gcaaatttca gcatagatct gtaggatttt tagaagaccg    5640
tgggccattg ccttcatgcc gtggtaagta ccacatctac aatttggta accgaactgg     5700 tgctttagta atgtggattt ttttctttt taaaagagat gtagcagaat aattcttcca     5760
gtgcaacaaa atcaattttt tgctaaacga ctccgagaac aacagttggg ctgtcaacat    5820
tcaaagcagc agagagggaa ctttgcacta ttggggtatg atgtttgggt cagttgataa    5880
aaggaaacct tttcatgcct ttagatgtga gcttccagta ggtaatgatt atgtgtcctt    5940
tcttgatggc tgtaatgaga acttcaatca ctgtagtcta agacctgatc tatagatgac    6000
ctagaatagc catgtactat aatgtgatga ttctaaattt gtacctatgt gacagacatt    6060
ttcaataatg tgaactgctg atttgatgga gctacttta gatttgtagg tgaaagtgta     6120
atactgttgg ttgaactatg ctgaagaggg aaagtgagcg attagttgag cccttgccgg    6180
gccttttttc cacctgccaa ttctacatgt attgttgtgg ttttattcat tgtatgaaaa    6240
ttcctgtgat tttttttaaa tgtgcagtac acatcagcct cactgagcta ataaagggaa    6300
acgaatgttt caaatct                                                  6317
```

<210> SEQ ID NO 2
<211> LENGTH: 798
<212> TYPE: PRT
<213> ORGANISM: Homo sapiens

<400> SEQUENCE: 2

Met Ala Trp Asp Met Cys Asn Gln Asp Ser Glu Ser Val Trp Ser Asp
 1               5                  10                  15

Ile Glu Cys Ala Ala Leu Val Gly Glu Asp Gln Pro Leu Cys Pro Asp
             20                  25                  30

Leu Pro Glu Leu Asp Leu Ser Glu Leu Asp Val Asn Asp Leu Asp Thr
         35                  40                  45

Asp Ser Phe Leu Gly Gly Leu Lys Trp Cys Ser Asp Gln Ser Glu Ile
     50                  55                  60

Ile Ser Asn Gln Tyr Asn Asn Glu Pro Ser Asn Ile Phe Glu Lys Ile
 65                  70                  75                  80

-continued

```
Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Gln Glu Ala Glu Pro Ser Leu Leu
    130                 135                 140

Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
                165                 170                 175

Arg Thr Asn Pro Ala Ile Val Lys Thr Glu Asn Ser Trp Ser Asn Lys
            180                 185                 190

Ala Lys Ser Ile Cys Gln Gln Lys Pro Gln Arg Arg Pro Cys Ser
        195                 200                 205

Glu Leu Leu Lys Tyr Leu Thr Thr Asn Asp Asp Pro His Thr Lys
    210                 215                 220

Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
                245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Pro Thr Thr Pro Pro His Lys Ala
    290                 295                 300

Asn Gln Asp Asn Pro Phe Arg Ala Ser Pro Lys Leu Lys Ser Ser Cys
305                 310                 315                 320

Lys Thr Val Val Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
    370                 375                 380

Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
                405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
        435                 440                 445

Thr Arg Lys Gln Leu Gln Asp Gln Glu Ile Arg Ala Glu Leu Asn Lys
    450                 455                 460

His Phe Gly His Pro Ser Gln Ala Val Phe Asp Asp Glu Ala Asp Lys
465                 470                 475                 480

Thr Gly Glu Leu Arg Asp Ser Asp Phe Ser Asn Glu Gln Phe Ser Lys
                485                 490                 495

Leu Pro Met Phe Ile Asn Ser Gly Leu Ala Met Asp Gly Leu Phe Asp
            500                 505                 510
```

```
Asp Ser Glu Asp Glu Ser Asp Lys Leu Ser Tyr Pro Trp Asp Gly Thr
        515                 520                 525

Gln Ser Tyr Ser Leu Phe Asn Val Ser Pro Ser Cys Ser Ser Phe Asn
        530                 535                 540

Ser Pro Cys Arg Asp Ser Val Ser Pro Lys Ser Leu Phe Ser Gln
545                 550                 555                 560

Arg Pro Gln Arg Met Arg Ser Arg Ser Arg Phe Ser Arg His Arg
                565                 570                 575

Ser Cys Ser Arg Ser Pro Tyr Ser Arg Ser Arg Ser Arg Pro Gly
        580                 585                 590

Ser Arg Ser Ser Ser Arg Ser Cys Tyr Tyr Glu Ser Ser His Tyr
        595                 600                 605

Arg His Arg Thr His Arg Asn Ser Pro Leu Tyr Val Arg Ser Arg Ser
        610                 615                 620

Arg Ser Pro Tyr Ser Arg Arg Pro Arg Tyr Asp Ser Tyr Glu Glu Tyr
625                 630                 635                 640

Gln His Glu Arg Leu Lys Arg Glu Glu Tyr Arg Arg Glu Tyr Glu Lys
                645                 650                 655

Arg Glu Ser Glu Arg Ala Lys Gln Arg Glu Arg Gln Arg Gln Lys Ala
                660                 665                 670

Ile Glu Glu Arg Arg Val Ile Tyr Val Gly Lys Ile Arg Pro Asp Thr
                675                 680                 685

Thr Arg Thr Glu Leu Arg Asp Arg Phe Glu Val Phe Gly Glu Ile Glu
        690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
                725                 730                 735

Thr Leu Arg Arg Ser Asn Glu Thr Asp Phe Glu Leu Tyr Phe Cys Gly
                740                 745                 750

Arg Lys Gln Phe Phe Lys Ser Asn Tyr Ala Asp Leu Asp Ser Asn Ser
                755                 760                 765

Asp Asp Phe Asp Pro Ala Ser Thr Lys Ser Lys Tyr Asp Ser Leu Asp
        770                 775                 780

Phe Asp Ser Leu Leu Lys Glu Ala Gln Arg Ser Leu Arg Arg
785                 790                 795
```

```
<210> SEQ ID NO 3
<211> LENGTH: 22
<212> TYPE: DNA
<213> ORGANISM: Artificial Sequence
<220> FEATURE:
<223> OTHER INFORMATION: Forward primer

<400> SEQUENCE: 3
agccgtgacc actgacaacg ag                                              22

<210> SEQ ID NO 4
<211> LENGTH: 22
<212> TYPE: DNA
<213> ORGANISM: Artificial Sequence
<220> FEATURE:
<223> OTHER INFORMATION: Forward primer

<400> SEQUENCE: 4
cgctccagga gactgaatcc ag                                              22
```

<210> SEQ ID NO 5
<211> LENGTH: 23
<212> TYPE: DNA
<213> ORGANISM: Artificial Sequence
<220> FEATURE:
<223> OTHER INFORMATION: Forward primer

<400> SEQUENCE: 5
catatgctga tcctgggcat aac                                              23

<210> SEQ ID NO 6
<211> LENGTH: 22
<212> TYPE: DNA
<213> ORGANISM: Artificial Sequence
<220> FEATURE:
<223> OTHER INFORMATION: Forward primer

<400> SEQUENCE: 6
acaccgacta ctacagcaac ag                                               22

<210> SEQ ID NO 7
<211> LENGTH: 22
<212> TYPE: DNA
<213> ORGANISM: Artificial Sequence
<220> FEATURE:
<223> OTHER INFORMATION: Forward primer

<400> SEQUENCE: 7
ggcattcaga ggcaaatcag ct                                               22

<210> SEQ ID NO 8
<211> LENGTH: 20
<212> TYPE: DNA
<213> ORGANISM: Artificial Sequence
<220> FEATURE:
<223> OTHER INFORMATION: Forward primer

<400> SEQUENCE: 8
gtctcccagg ctctggtccg                                                  20

<210> SEQ ID NO 9
<211> LENGTH: 22
<212> TYPE: DNA
<213> ORGANISM: Artificial Sequence
<220> FEATURE:
<223> OTHER INFORMATION: Forward primer

<400> SEQUENCE: 9
tccgaagact gtcgctcctg tg                                               22

<210> SEQ ID NO 10
<211> LENGTH: 22
<212> TYPE: DNA
<213> ORGANISM: Artificial Sequence
<220> FEATURE:
<223> OTHER INFORMATION: Forward primer

<400> SEQUENCE: 10
ggtacgcact ggccgaagca tc                                               22

<210> SEQ ID NO 11
<211> LENGTH: 24
<212> TYPE: DNA
<213> ORGANISM: Artificial Sequence
<220> FEATURE:
<223> OTHER INFORMATION: Forward primer

<400> SEQUENCE: 11

```
gtcggtacct ggaagctagt ggac                                              24
```

<210> SEQ ID NO 12
<211> LENGTH: 22
<212> TYPE: DNA
<213> ORGANISM: Artificial Sequence
<220> FEATURE:
<223> OTHER INFORMATION: Forward primer

<400> SEQUENCE: 12

```
gttctgcaga ggatcttcag gc                                                22
```

<210> SEQ ID NO 13
<211> LENGTH: 23
<212> TYPE: DNA
<213> ORGANISM: Artificial Sequence
<220> FEATURE:
<223> OTHER INFORMATION: Forward primer

<400> SEQUENCE: 13

```
cagtgtggtg cacgtctcca atc                                               23
```

<210> SEQ ID NO 14
<211> LENGTH: 21
<212> TYPE: DNA
<213> ORGANISM: Artificial Sequence
<220> FEATURE:
<223> OTHER INFORMATION: Forward primer

<400> SEQUENCE: 14

```
caggtcactg tgcccttacc a                                                 21
```

<210> SEQ ID NO 15
<211> LENGTH: 21
<212> TYPE: DNA
<213> ORGANISM: Artificial Sequence
<220> FEATURE:
<223> OTHER INFORMATION: Forward primer

<400> SEQUENCE: 15

```
agtccctgcc ctttgtacac a                                                 21
```

<210> SEQ ID NO 16
<211> LENGTH: 22
<212> TYPE: DNA
<213> ORGANISM: Artificial Sequence
<220> FEATURE:
<223> OTHER INFORMATION: Forward primer

<400> SEQUENCE: 16

```
cactgtagtg ggcgttggac aa                                                22
```

<210> SEQ ID NO 17
<211> LENGTH: 22
<212> TYPE: DNA
<213> ORGANISM: Artificial Sequence
<220> FEATURE:
<223> OTHER INFORMATION: Forward primer

<400> SEQUENCE: 17

```
caacgtgttc ctcaagtcgc gg                                                22
```

<210> SEQ ID NO 18
<211> LENGTH: 22
<212> TYPE: DNA
<213> ORGANISM: Artificial Sequence

```
<220> FEATURE:
<223> OTHER INFORMATION: Forward primer

<400> SEQUENCE: 18
gctggacagt gagctgagaa ac                                              22

<210> SEQ ID NO 19
<211> LENGTH: 22
<212> TYPE: DNA
<213> ORGANISM: Artificial Sequence
<220> FEATURE:
<223> OTHER INFORMATION: Forward primer

<400> SEQUENCE: 19
gatgagctac acgctggact cg                                              22

<210> SEQ ID NO 20
<211> LENGTH: 23
<212> TYPE: DNA
<213> ORGANISM: Artificial Sequence
<220> FEATURE:
<223> OTHER INFORMATION: Forward primer

<400> SEQUENCE: 20
actccaagcg tgagatcgtg gac                                             23

<210> SEQ ID NO 21
<211> LENGTH: 21
<212> TYPE: DNA
<213> ORGANISM: Artificial Sequence
<220> FEATURE:
<223> OTHER INFORMATION: Forward primer

<400> SEQUENCE: 21
tcatcgtagc caacgtgcca g                                               21

<210> SEQ ID NO 22
<211> LENGTH: 23
<212> TYPE: DNA
<213> ORGANISM: Artificial Sequence
<220> FEATURE:
<223> OTHER INFORMATION: Reverse primer

<400> SEQUENCE: 22
gctgcatggt tctgagtgct aag                                             23

<210> SEQ ID NO 23
<211> LENGTH: 21
<212> TYPE: DNA
<213> ORGANISM: Artificial Sequence
<220> FEATURE:
<223> OTHER INFORMATION: Reverse primer

<400> SEQUENCE: 23
cttgactact gtctgtgagg c                                               21

<210> SEQ ID NO 24
<211> LENGTH: 22
<212> TYPE: DNA
<213> ORGANISM: Artificial Sequence
<220> FEATURE:
<223> OTHER INFORMATION: Reverse primer

<400> SEQUENCE: 24
caaacttcat ccaggcaatg tc                                              22
```

```
<210> SEQ ID NO 25
<211> LENGTH: 22
<212> TYPE: DNA
<213> ORGANISM: Artificial Sequence
<220> FEATURE:
<223> OTHER INFORMATION: Reverse primer

<400> SEQUENCE: 25
cctcgaaaga tagcaagagt ag                                              22

<210> SEQ ID NO 26
<211> LENGTH: 21
<212> TYPE: DNA
<213> ORGANISM: Artificial Sequence
<220> FEATURE:
<223> OTHER INFORMATION: Reverse primer

<400> SEQUENCE: 26
caatgaacac tgccacacct c                                               21

<210> SEQ ID NO 27
<211> LENGTH: 22
<212> TYPE: DNA
<213> ORGANISM: Artificial Sequence
<220> FEATURE:
<223> OTHER INFORMATION: Reverse primer

<400> SEQUENCE: 27
ctgtacagga cgttgtccat tc                                              22

<210> SEQ ID NO 28
<211> LENGTH: 22
<212> TYPE: DNA
<213> ORGANISM: Artificial Sequence
<220> FEATURE:
<223> OTHER INFORMATION: Reverse primer

<400> SEQUENCE: 28
tatgttcacc agtgttatgc ca                                              22

<210> SEQ ID NO 29
<211> LENGTH: 22
<212> TYPE: DNA
<213> ORGANISM: Artificial Sequence
<220> FEATURE:
<223> OTHER INFORMATION: Reverse primer

<400> SEQUENCE: 29
tgatcctgct ccgtcatctc ag                                              22

<210> SEQ ID NO 30
<211> LENGTH: 23
<212> TYPE: DNA
<213> ORGANISM: Artificial Sequence
<220> FEATURE:
<223> OTHER INFORMATION: Reverse primer

<400> SEQUENCE: 30
gatctctgtg ttcttgaagg tac                                             23

<210> SEQ ID NO 31
<211> LENGTH: 22
<212> TYPE: DNA
<213> ORGANISM: Artificial Sequence
<220> FEATURE:
<223> OTHER INFORMATION: Reverse primer

<400> SEQUENCE: 31
```
gtcctccaga tgcctgtcgc tt                                          22

<210> SEQ ID NO 32
<211> LENGTH: 21
<212> TYPE: DNA
<213> ORGANISM: Artificial Sequence
<220> FEATURE:
<223> OTHER INFORMATION: Reverse primer

<400> SEQUENCE: 32
tgaaccaaag ttgaccacca g                                           21

<210> SEQ ID NO 33
<211> LENGTH: 21
<212> TYPE: DNA
<213> ORGANISM: Artificial Sequence
<220> FEATURE:
<223> OTHER INFORMATION: Reverse primer

<400> SEQUENCE: 33
cactacgttc caggatccca a                                           21

<210> SEQ ID NO 34
<211> LENGTH: 19
<212> TYPE: DNA
<213> ORGANISM: Artificial Sequence
<220> FEATURE:
<223> OTHER INFORMATION: Reverse primer

<400> SEQUENCE: 34
cgatccgagg gcctcacta                                              19

<210> SEQ ID NO 35
<211> LENGTH: 22
<212> TYPE: DNA
<213> ORGANISM: Artificial Sequence
<220> FEATURE:
<223> OTHER INFORMATION: Reverse primer

<400> SEQUENCE: 35
cggccacaat tttcggagtc tg                                          22

<210> SEQ ID NO 36
<211> LENGTH: 21
<212> TYPE: DNA
<213> ORGANISM: Artificial Sequence
<220> FEATURE:
<223> OTHER INFORMATION: Reverse primer

<400> SEQUENCE: 36
gccaggttct ctttactcat c                                           21

<210> SEQ ID NO 37
<211> LENGTH: 22
<212> TYPE: DNA
<213> ORGANISM: Artificial Sequence
<220> FEATURE:
<223> OTHER INFORMATION: Reverse primer

<400> SEQUENCE: 37
caaagccaat ccgacactct tc                                          22

<210> SEQ ID NO 38
<211> LENGTH: 22
<212> TYPE: DNA
<213> ORGANISM: Artificial Sequence

```
<220> FEATURE:
<223> OTHER INFORMATION: Reverse primer

<400> SEQUENCE: 38
tgtaggagga ggacacggtg ct                                              22

<210> SEQ ID NO 39
<211> LENGTH: 22
<212> TYPE: DNA
<213> ORGANISM: Artificial Sequence
<220> FEATURE:
<223> OTHER INFORMATION: Reverse primer

<400> SEQUENCE: 39
ggacgcagct ggctggtgct tg                                              22

<210> SEQ ID NO 40
<211> LENGTH: 22
<212> TYPE: DNA
<213> ORGANISM: Artificial Sequence
<220> FEATURE:
<223> OTHER INFORMATION: Reverse primer

<400> SEQUENCE: 40
gtcttgtctg agcagatggt ag                                              22

<210> SEQ ID NO 41
<211> LENGTH: 21
<212> TYPE: DNA
<213> ORGANISM: Artificial Sequence
<220> FEATURE:
<223> OTHER INFORMATION: Genotyping primer

<400> SEQUENCE: 41
cttccatgtg tcactgtagt c                                               21

<210> SEQ ID NO 42
<211> LENGTH: 20
<212> TYPE: DNA
<213> ORGANISM: Artificial Sequence
<220> FEATURE:
<223> OTHER INFORMATION: Genotyping primer

<400> SEQUENCE: 42
ggatgatagg tatgcgttac                                                 20

<210> SEQ ID NO 43
<211> LENGTH: 23
<212> TYPE: DNA
<213> ORGANISM: Artificial Sequence
<220> FEATURE:
<223> OTHER INFORMATION: Genotyping primer

<400> SEQUENCE: 43
tccagtaggc agagatttat gac                                             23

<210> SEQ ID NO 44
<211> LENGTH: 23
<212> TYPE: DNA
<213> ORGANISM: Artificial Sequence
<220> FEATURE:
<223> OTHER INFORMATION: Genotyping primer

<400> SEQUENCE: 44
ccaactgtct ataattccag ttc                                             23
```

<210> SEQ ID NO 45
<211> LENGTH: 3029
<212> TYPE: DNA
<213> ORGANISM: Mus musculus

<400> SEQUENCE: 45

| | | | | | | |
|---|---|---|---|---|---|---|
| aattcggcac | gaggttgcct | gcatgagtgt | gtgctgtgtg | tcagagtgga | ttggagttga | 60 |
| aaaagcttga | ctggcgtcat | tcgggagctg | gatggcttgg | gacatgtgca | gccaagactc | 120 |
| tgtatggagt | gacatagagt | gtgctgctct | ggttggtgag | gaccagcctc | tttgcccaga | 180 |
| tcttcctgaa | cttgaccttt | ctgaacttga | tgtgaatgac | ttggatacag | acagctttct | 240 |
| gggtggattg | aagtggtgta | gcgaccaatc | ggaaatcata | tccaaccagt | acaacaatga | 300 |
| gcctgcgaac | atatttgaga | gatagatga | agagaatgag | gcaaacttgc | tagcggtcct | 360 |
| cacagagaca | ctggacagtc | tccccgtgga | tgaagacgga | ttgccctcat | ttgatgcact | 420 |
| gacagatgga | gccgtgacca | ctgacaacga | ggccagtcct | tcctccatgc | ctgacggcac | 480 |
| ccctccccct | caggaggcag | aagagccgtc | tctacttaag | aagctcttac | tggcaccagc | 540 |
| caacactcag | ctcagctaca | atgaatgcag | cggtcttagc | actcagaacc | atgcagcaaa | 600 |
| ccacacccac | aggatcagaa | caaaccctgc | cattgttaag | accgagaatt | catggagcaa | 660 |
| taaagcgaag | agcatttgtc | aacagcaaaa | gccacaaaga | cgtccctgct | cagagcttct | 720 |
| caagtatctg | accacaaacg | atgaccctcc | tcacaccaaa | cccacagaaa | acaggaacag | 780 |
| cagcagagac | aaatgtgctt | ccaaaaagaa | gtcccataca | caaccgcagt | cgcaacatgc | 840 |
| tcaagccaaa | ccaacaactt | tatctcttcc | tctgacccca | gagtcaccaa | atgaccccaa | 900 |
| gggttcccca | tttgagaaca | agactattga | gcgaacctta | agtgtggaac | tctctggaac | 960 |
| tgcaggccta | actcctccca | caactcctcc | tcataaagcc | aaccaagata | ccctttcaa | 1020 |
| ggcttcgcca | agctgaagc | cctcttgcaa | gaccgtggtg | ccaccgccaa | ccaagagggc | 1080 |
| ccggtacagt | gagtgttctg | gtacccaagg | cagccactcc | accaagaaag | ggcccgagca | 1140 |
| atctgagttg | tacgcacaac | tcagcaagtc | ctcagggctc | agccgaggac | acgaggaaag | 1200 |
| gaagactaaa | cggcccagtc | tccggctgtt | tggtgaccat | gactactgtc | agtcactcaa | 1260 |
| ttccaaaacg | gatatactca | ttaacatatc | acaggagctc | caagactcta | gacaactaga | 1320 |
| cttcaaagat | gcctcctgtg | actggcaggg | gcacatctgt | tcttccacag | attcaggcca | 1380 |
| gtgctacctg | agagagactt | tggaggccag | caagcaggtc | tctccttgca | gcaccagaaa | 1440 |
| acagctccaa | gaccaggaaa | tccgagcgga | gctgaacaag | cacttcggtc | atccctgtca | 1500 |
| agctgtgttt | gacgacaaat | cagacaagac | cagtgaacta | agggatggcg | acttcagtaa | 1560 |
| tgaacaattc | tccaaactac | ctgtgtttat | aaattcagga | ctagccatgg | atggcctatt | 1620 |
| tgatgacagt | gaagatgaaa | gtgataaact | gagctaccct | tgggatggca | cgcagcccta | 1680 |
| ttcattgttc | gatgtgtcgc | cttcttgctc | ttccttaac | tctccgtgtc | gagactcagt | 1740 |
| gtcaccaccg | aaatccttat | tttctcaaag | accccaaagg | atgcgctctc | gttcaagatc | 1800 |
| cttttctcga | cacaggtcgt | gttcccgatc | accatattcc | aggtcaagat | caaggtcccc | 1860 |
| aggcagtaga | tcctcttcaa | gatcctgtta | ctactatgaa | tcaagccact | acagacaccg | 1920 |
| cacacaccgc | aattctccct | tgtatgtgag | atcacgttca | aggtcaccct | acagccgtag | 1980 |
| gcccaggtac | gacagctatg | aagcctatga | gcacgaaagg | ctcaagaggg | atgaataccg | 2040 |
| caaagagcac | gagaagcggg | agtctgaaag | ggccaaacag | agagagaggc | agaagcagaa | 2100 |
| agcaattgaa | gagcgccgtg | tgatttacgt | tggtaaaatc | agacctgaca | caacgcggac | 2160 |
| agaattgaga | gaccgctttg | aagttttgg | tgaaattgag | gaatgcaccg | taaatctgcg | 2220 |

```
ggatgatgga  gacagctatg  gtttcatcac  ctaccgttac  acctgtgacg  ctttcgctgc   2280
tcttgagaat  ggatatactt  tacgcaggtc  gaacgaaact  gacttcgagc  tgtactttttg  2340 tggacggaag  caattttttca agtctaacta  tgcagaccta  gataccaact  cagacgattt   2400
tgaccctgct  tccaccaaga  gcaagtatga  ctctctggat  tttgatagtt  tactgaagga   2460
agctcagaga  agcttgcgca  ggtaacgtgt  tcccaggctg  aggaatgaca  gagagatggt   2520
caatacctca  tgggacagcg  tgtcctttcc  caagactctt  gcaagtcata  cttaggaatt   2580
tctcctactt  tacactctct  gtacaaaaat  aaaacaaaac  aaaacaacaa  taacaacaac   2640
aacaacaaca  ataacaacaa  caaccatacc  agaacaagaa  caacggttta  catgaacaca   2700
gctgctgaag  aggcaagaga  cagaatgata  atccagtaag  cacacgttta  ttcacgggtg   2760
tcagctttgc  tttccctgga  ggctcttggt  gacagtgtgt  gtgcgtgtgt  gtgtgtgggt   2820
gtgcgtgtgt  gtatgtgtgt  gtgtgtactt  gtttggaaag  tacatatgta  cacatgtgag   2880 gacttgggggg cacctgaaca  gaacgaacaa  gggcgacccc  ttcaaatggc  agcatttcca   2940
tgaagacaca  cttaaaacct  acaacttcaa  aatgttcgta  ttctatacaa  aaggaaaata   3000
aataaatata  aaaaaaaaaa  aaaaaaaaa                                       3029
```

<210> SEQ ID NO 46
<211> LENGTH: 797
<212> TYPE: PRT
<213> ORGANISM: Mus musculus

<400> SEQUENCE: 46

```
Met Ala Trp Asp Met Cys Ser Gln Asp Ser Val Trp Ser Asp Ile Glu
 1               5                  10                  15

Cys Ala Ala Leu Val Gly Glu Asp Gln Pro Leu Cys Pro Asp Leu Pro
             20                  25                  30

Glu Leu Asp Leu Ser Glu Leu Asp Val Asn Asp Leu Asp Thr Asp Ser
         35                  40                  45

Phe Leu Gly Gly Leu Lys Trp Cys Ser Asp Gln Ser Glu Ile Ile Ser
     50                  55                  60

Asn Gln Tyr Asn Asn Glu Pro Ala Asn Ile Phe Glu Lys Ile Asp Glu
 65                  70                  75                  80

Glu Asn Glu Ala Asn Leu Leu Ala Val Leu Thr Glu Thr Leu Asp Ser
                 85                  90                  95

Leu Pro Val Asp Glu Asp Gly Leu Pro Ser Phe Asp Ala Leu Thr Asp
            100                 105                 110

Gly Ala Val Thr Thr Asp Asn Glu Ala Ser Pro Ser Ser Met Pro Asp
        115                 120                 125

Gly Thr Pro Pro Pro Gln Glu Ala Glu Glu Pro Ser Leu Leu Lys Lys
    130                 135                 140

Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Gln Lys Pro Gln Arg Arg Pro Cys Ser Glu
        195                 200                 205

Leu Leu Lys Tyr Leu Thr Thr Asn Asp Asp Pro Pro His Thr Lys Pro
    210                 215                 220

Thr Glu Asn Arg Asn Ser Ser Arg Asp Lys Cys Ala Ser Lys Lys Lys
```

```
            225                 230                 235                 240
Ser His Thr Gln Pro Gln Ser Gln His Ala Gln Ala Lys Pro Thr Thr
                    245                 250                 255

Leu Ser Leu Pro Leu Thr Pro Glu Ser Pro Asn Asp Pro Lys Gly Ser
                    260                 265                 270

Pro Phe Glu Asn Lys Thr Ile Glu Arg Thr Leu Ser Val Glu Leu Ser
                    275                 280                 285

Gly Thr Ala Gly Leu Thr Pro Pro Thr Thr Pro His Lys Ala Asn
            290                 295                 300

Gln Asp Asn Pro Phe Lys Ala Ser Pro Lys Leu Lys Pro Ser Cys Lys
305                 310                 315                 320

Thr Val Val Pro Pro Thr Lys Arg Ala Arg Tyr Ser Glu Cys Ser
                    325                 330                 335

Gly Thr Gln Gly Ser His Ser Thr Lys Lys Gly Pro Glu Gln Ser Glu
                    340                 345                 350

Leu Tyr Ala Gln Leu Ser Lys Ser Ser Gly Leu Ser Arg Gly His Glu
            355                 360                 365

Glu Arg Lys Thr Lys Arg Pro Ser Leu Arg Leu Phe Gly Asp His Asp
        370                 375                 380

Tyr Cys Gln Ser Leu Asn Ser Lys Thr Asp Ile Leu Ile Asn Ile Ser
385                 390                 395                 400

Gln Glu Leu Gln Asp Ser Arg Gln Leu Asp Phe Lys Asp Ala Ser Cys
                    405                 410                 415

Asp Trp Gln Gly His Ile Cys Ser Ser Thr Asp Ser Gly Gln Cys Tyr
                    420                 425                 430

Leu Arg Glu Thr Leu Glu Ala Ser Lys Gln Val Ser Pro Cys Ser Thr
            435                 440                 445

Arg Lys Gln Leu Gln Asp Gln Glu Ile Arg Ala Glu Leu Asn Lys His
        450                 455                 460

Phe Gly His Pro Cys Gln Ala Val Phe Asp Asp Lys Ser Asp Lys Thr
465                 470                 475                 480

Ser Glu Leu Arg Asp Gly Asp Phe Ser Asn Glu Gln Phe Ser Lys Leu
                    485                 490                 495

Pro Val Phe Ile Asn Ser Gly Leu Ala Met Asp Gly Leu Phe Asp Asp
                    500                 505                 510

Ser Glu Asp Glu Ser Asp Lys Leu Ser Tyr Pro Trp Asp Gly Thr Gln
            515                 520                 525

Pro Tyr Ser Leu Phe Asp Val Ser Pro Ser Cys Ser Ser Phe Asn Ser
        530                 535                 540

Pro Cys Arg Asp Ser Val Ser Pro Pro Lys Ser Leu Phe Ser Gln Arg
545                 550                 555                 560

Pro Gln Arg Met Arg Ser Arg Ser Arg Ser Phe Ser Arg His Arg Ser
                    565                 570                 575

Cys Ser Arg Ser Pro Tyr Ser Arg Ser Arg Ser Arg Ser Pro Gly Ser
                    580                 585                 590

Arg Ser Ser Ser Arg Ser Cys Tyr Tyr Tyr Glu Ser Ser His Tyr Arg
            595                 600                 605

His Arg Thr His Arg Asn Ser Pro Leu Tyr Val Arg Ser Arg Ser Arg
        610                 615                 620

Ser Pro Tyr Ser Arg Arg Pro Arg Tyr Asp Ser Tyr Glu Ala Tyr Glu
625                 630                 635                 640

His Glu Arg Leu Lys Arg Asp Glu Tyr Arg Lys Glu His Glu Lys Arg
                    645                 650                 655
```

```
Glu Ser Glu Arg Ala Lys Gln Arg Glu Arg Gln Lys Gln Lys Ala Ile
            660                 665                 670

Glu Glu Arg Arg Val Ile Tyr Val Gly Lys Ile Arg Pro Asp Thr Thr
        675                 680                 685

Arg Thr Glu Leu Arg Asp Arg Phe Glu Val Phe Gly Glu Ile Glu Glu
    690                 695                 700

Cys Thr Val Asn Leu Arg Asp Asp Gly Asp Ser Tyr Gly Phe Ile Thr
705                 710                 715                 720

Tyr Arg Tyr Thr Cys Asp Ala Phe Ala Ala Leu Glu Asn Gly Tyr Thr
                725                 730                 735

Leu Arg Arg Ser Asn Glu Thr Asp Phe Glu Leu Tyr Phe Cys Gly Arg
            740                 745                 750

Lys Gln Phe Phe Lys Ser Asn Tyr Ala Asp Leu Asp Thr Asn Ser Asp
        755                 760                 765

Asp Phe Asp Pro Ala Ser Thr Lys Ser Lys Tyr Asp Ser Leu Asp Phe
    770                 775                 780

Asp Ser Leu Leu Lys Glu Ala Gln Arg Ser Leu Arg Arg
785                 790                 795

<210> SEQ ID NO 47
<211> LENGTH: 5
<212> TYPE: PRT
<213> ORGANISM: Mus musculus
<220> FEATURE:
<221> NAME/KEY: misc_feature
<222> LOCATION: (2)..(3)
<223> OTHER INFORMATION: Xaa's at postions 2 and 3 may be any amino
      acid

<400> SEQUENCE: 47

Leu Xaa Xaa Leu Leu
1               5
```

US 7,947,652 B2

COMPOSITIONS AND METHODS FOR MODULATING PGC-1α TO TREAT HUNTINGTON'S DISEASE

GOVERNMENT RIGHTS

This invention was made at least in part with support by grants awarded from the National Institute of Diabetes and Kidney Diseases (NIDDK) of the National Institutes of Health, grant numbers DK54477, DK61562, and K01DK065584. The U.S. government may have certain rights in the invention.

BACKGROUND OF THE INVENTION

Understanding the regulatory circuits that govern cellular energy and glucose metabolism has been a focus of research interest in the past decade. Recent studies have implicated transcription coactivators of the PGC-1 family, in particular PGC-1α and PGC-1β, as important regulators of mitochondrial biogenesis and cellular respiration in several cell types (Kelly, D. P., and Scarpulla, R. C. (2004) *Genes Dev* 18, 357-368; Puigserver, P., and Spiegelman, B. M. (2003) *Endocr Rev* 24, 78-90.). Notably, the expression of PGC-1α has been found to be dysregulated in diabetic liver and skeletal muscle, tissues critical for maintaining normal blood glucose levels, while PGC-1β mRNA levels are also lowered in diabetic muscle (Mootha et al. (2003) *Nat Genet* 34, 267-273; Patti, M. et al. (2003) *Proc Natl Acad Sci USA* 100, 8466-8471; Yoon J. C., et al. (2001) *Nature* 413, 131-138). PGC-1α was initially identified as a cold-inducible coactivator for PPARγ in brown fat (Puigserver et al. (1998) *Cell* 92, 829-839). Subsequent studies revealed that PGC-1α is able to bind to and augment transcriptional activities of many nuclear receptors and several other transcription factors outside the nuclear receptor superfamily. Adenoviral-mediated or transgenic expression of PGC-1α in cultured cells and in vivo leads to activation of mitochondrial biogenesis and increases in cellular respiration (Lehman et al., (2000) *J Clin Invest* 106, 847-856; Lin et al. (2002b) *Nature* 418, 797-801; St-Pierre et al. (2003) *J Biol Chem* 278, 26597-26603; Wu et al. (1999) *Cell* 98, 115-124). Consistent with a regulatory role in the cellular adaptations to increased energy requirements, the expression of PGC-1α itself is highly regulated in response to nutritional and environmental stimuli. For example, PGC-1α mRNA is strongly induced in brown fat by cold exposure and in skeletal muscle following physical activity (Baar et al. (2002) *Faseb J* 16, 1879-1886; Goto et al. (2000) *Biochem Biophys Res Commun* 274, 350-354; Puigserver et al. (1998) *Cell* 92, 829-839). Increased PGC-1α levels in these tissues lead to enhanced mitochondrial electron transport activities that enable cells to meet rising energy demands, such as during adaptive thermogenesis in brown fat and contraction in muscle.

In addition to its role in mitochondrial biology, PGC-1α also regulates several key metabolic programs that go beyond simple mitochondrial biogenesis and oxidative phosphorylation. For example, PGC-1α drives expression of myofibrillar proteins characteristic of slow-twitch muscle fibers when expressed in fast-twitch muscle beds of transgenic mice (Lin et al. (2002b) *Nature* 418, 797-801). In the liver, PGC-1α mRNA level is rapidly induced following short-term fasting (Yoon et al. (2001) *Nature* 413, 131-138). Adenoviral-mediated expression of PGC-1α in cultured primary hepatocytes and in live rats leads to activation of the entire program of gluconeogenesis and increased glucose production (Yoon et al. (2001) *Nature* 413, 131-138). In all of these cases, PGC-1α interacts with cell-selective transcription factors to execute these tissue-specific functions, such as MEF2c in skeletal muscle and HNF4α and FOXO1 in the liver.

SUMMARY OF THE INVENTION

The present invention is based, at least in part, on the discovery that modulation of PGC-1α, e.g., PGC-1α expression or activity, leads to the modulation of lesion formation, e.g., brain lesion formation, neurological degeneration, and neurite formation. Therefore, in one aspect, the present invention provides a method for treating and/or preventing a neurological disease or disorder in a subject, e.g., a human, by administering a PGC-1α modulator.

Examples of neurological diseases or disorders include Alzheimer's disease, Parkinson's disease, Huntington's disease, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis (MS), amyotrophic lateral sclerosis (ALS), progressive supranuclear palsy (PSP), epilepsy, Creutzfeldt-Jakob disease, deafness-dytonia syndrome, Leigh syndrome, Leber hereditary optic neuropathy (LHON), parkinsonism, dystonia, motor neuron disease, neuropathy-ataxia and retinitis pimentosa (NARP), maternal inherited Leigh syndrome (MILS), Friedreich ataxia, hereditary spastic paraplegia, Mohr-Tranebjaerg syndrome, Wilson disease, sporatic Alzheimer's disease, sporadic amyotrophic lateral sclerosis, sporadic Parkinson's disease, autonomic function disorders, hypertension, sleep disorders, neuropsychiatric disorders, depression, schizophrenia, schizoaffective disorder, korsakoff's psychosis, mania, anxiety disorders, phobic disorder, learning or memory disorders, amnesia or age-related memory loss, attention deficit disorder, dysthymic disorder, major depressive disorder, obsessive-compulsive disorder, psychoactive substance use disorders, panic disorder, bipolar affective disorder, severe bipolar affective (mood) disorder (BP-1), migraines, hyperactivity and movement disorders.

In one embodiment, a PGC-1α modulator is used in the methods of the invention, wherein the modulator is capable of modulating PGC-1α polypeptide activity. In another embodiment, the modulator is a PGC-1α polypeptide comprising the amino acid sequence of SEQ ID NO: 2, or a fragment thereof. In still another embodiment, the modulator includes a PGC-1α polypeptide comprising an amino acid sequence which is at least 90 percent identical to the amino acid sequence of SEQ ID NO: 2.

In yet another embodiment, the PGC-1α modulator is an isolated naturally occurring allelic variant of a polypeptide consisting of the amino acid sequence of SEQ ID NO:2, wherein the polypeptide is encoded by a nucleic acid molecule which hybridizes to a complement of a nucleic acid molecule consisting of SEQ ID NO:1 at 6×SSC at 45° C., followed by one or more washes in 0.2×SSC, 0.1% SDS at 65° C.

In still a further embodiment, the PGC-1α modulator is capable of modulating PGC-1α nucleic acid expression. For example, the PGC-1α modulator includes a PGC-1α nucleic acid molecule, e.g., a PGC-1α nucleic acid molecule comprising the nucleotide sequence of SEQ ID NO:1, or a fragment thereof. In another embodiment, the PGC-1α modulator is a modulator of a transcriptional activator which modulates the expression of PGC-1α.

In yet another embodiment, the PGC-1α modulator modulates mitochondrial function, e.g., mitochondrial function in the brain. In still another embodiment, the PGC-1α modulator is capable of modulating lesion formation in the brain. In still a further embodiment, the PGC-1α modulator is capable of modulating neurite growth.

In another aspect, the invention provides a method of modulating brain lesion formation by contacting a cell with a PGC-1α modulator such that brain lesion formation is modulated. In yet another aspect, the invention provides a method for modulating neuronal degeneration by contacting a cell with a PGC-1α modulator such that neuronal degeneration is modulated.

In still another aspect, the invention provides methods for identifying a compound capable of treating or preventing a neurological disease or disorder comprising the step of assaying the ability of the compound to modulate PGC-1α nucleic acid expression or PGC-1α polypeptide activity. In one embodiment, a modulating compound is identified by detecting modulation of mitochondrial function or by detecting modulation in the expression or activity of mitochondrial genes, e.g., LDH2, Ndufb5, COX6a1, and ATP5j. In another embodiment, a modulating compound is identified by detecting modulation in the expression or activity of neuronal genes, e.g., NF-H, NF-M, MOBP, ATPa1, and ATPa2. A PGC-1α modulator identified by the methods of the invention includes, but is not limited to, a small molecule, a nucleic acid molecule, a polypeptide, a peptide or peptidomimetic.

In still another aspect, the invention provides methods for assessing whether a subject is afflicted with a neurological disease or disorder or is at risk of developing a neurological disease or disorder, comprising the step of detecting the expression of the PGC-1α gene or the activity of PGC-1α in a cell or tissue sample of a subject, e.g., cerebrospinal fluid, spinal fluid, and neural tissue.

In yet another aspect, the invention provides a non-human animal, in which a PGC-1α gene is misexpressed, e.g., a transgenic animal, in particular, a mouse. In a further embodiment, the animal has a PGC-1α gene that is disrupted by the removal of DNA encoding all or part of the PGC-1α gene. The present invention also includes animals that are homozygous for the disrupted gene or heterozygous for the disrupted gene. In one embodiment, the invention provides a transgenic mouse with a disruption of the PGC-1α gene, e.g., an insertion or deletion of the PGC-1α gene.

BRIEF DESCRIPTION OF THE DRAWINGS

FIG. 1A depicts hybridization analysis of PGC-1αmRNA in liver and skeletal muscle using a probe spanning exons 3 to 5 of PGC-1α. Hybridization with a probe specific for ribosomal protein 36B4 was included as a loading control. FIG. 1B depicts the results of immunoblotting of PGC-1α protein. Lysates containing in vitro translated PGC-1α were used as a positive control. Note the absence of PGC-1α protein in brown fat extracts from PGC-1α$^{-/-}$ mice. FIGS. 1C-D depict H&E staining of paraffin-embedded liver sections. FIGS. 1E-F depict H&E staining of plastic-embedded brown fat sections.

FIG. 2A depicts plasma glucose levels in PGC-1α$^{+/+}$ (filled box), PGC-1α$^{+/-}$ (dotted box) and PGC-1α$^{-/-}$ (open box) in the fed and fasted (24 hours) states. *p=0.0007. FIG. 2B depicts plasma insulin concentrations in the same group of mice used in (2A). *p=0.005. FIG. 2C depicts total and uncoupled respiration in wild-type (+/+) and PGC-1α deficient (−/−) hepatocytes. *p<0.02. Data in FIGS. 2A-C represent mean±s.e.m. Furthermore, FIG. 2D depicts defective hormone-induced gluconeogenic gene expression in hepatocytes lacking PGC-1α. Primary hepatocytes were isolated from PGC-1α$^{+/+}$ and PGC-1α$^{-/-}$ mice and treated with 0.2 µM or 1.0 µM of a combination of forskolin and dex for 3 or 6 hours before RNA isolation and hybridization. Hybridization for ribosomal protein 36B4 mRNA was included as a loading control. FIG. 2E depicts the results of pyruvate tolerance test. Three-month old male mice were fasted overnight before receiving IP injection of a pyruvate solution as described in the Examples Section. *p<0.0002; **p<0.02.

FIG. 3A depicts hybridization analysis of mRNAs for metabolic genes in the fed and fasted liver. Three-month old male mice were fed ad libitum or fasted for 24 hours before harvesting tissues for mRNA analysis. FIG. 3B depicts expression of mRNAs for transcription factors that regulate hepatic metabolism. Note the dramatic induction of C/EBPβ mRNA in fed PGC-1α$^{-/-}$ liver compared to wild-type liver. FIG. 3C is a graph depicting real-time PCR analysis of mRNA levels for the C/EBP family members. FIG. 3D is a graph which illustrates that PGC-1α does not coactivate C/EBPβ. H2.35 hepatoma cells were transiently transfected with a UAS-luciferase reporter with Gal-4-DBD-C/EBPβ in the presence or absence of PGC-1α. Luciferase activity was measured 30 hours following transfection. FIG. 3E is a graph which depicts induction of endogenous gluconeogenic genes by C/EBPβ in primary hepatocytes. Primary hepatocytes were isolated from PGC-1α$^{+/+}$ (filled box) and PGC-1α$^{-/-}$ (open box) mouse liver and infected with adenoviruses expression GFP or C/EBPβ. Total RNA were harvested following 3 hours of treatments with 0.2 µM forskolin and 0.1 µM dex. Relative abundance of G6Pase and PEPCK mRNA was examined by real-time PCR followed by normalization to 18S ribosomal RNA.

FIG. 4A is a graph which depicts body weight of PGC-1α$^{+/+}$ (filled circle, n=6) and PGC-1α$^{-/-}$ (filled square, n=6) mice fed a high-fat diet. Twelve-week old males were fed a high-fat diet for 16 weeks. Body weight was measured weekly. FIG. 4B depicts representative DEXA scanning images of PGC-1α$^{+/+}$ and PGC-1α$^{-/-}$ mice after 12 weeks of high-fat feeding. FIG. 4C is a graph depicting body fat content in PGC-1α$^{+/+}$ and PGC-1α$^{-/-}$ mice under chow (four month-old males) or high-fat feeding. Percent body fat was determined by automated analysis of DEXA images with a program supplied by manufacturer. *p=0.005; **p=0.001. FIG. 4D is a graph depicting fasting glucose and insulin levels in high-fat fed mice. *p=0.0001; **p=0.02. FIG. 4E is a graph depicting insulin tolerance test on high-fat fed PGC-1α$^{+/+}$ (filled circle, n=5) and PGC-1α$^{-/-}$ (filled square, n=5) mice. *p<0.004. FIG. 4F is a graph depicting glucose tolerance test in high-fat fed mice following an overnight fast. *p<0.02. Insulin and glucose tolerance tests were performed as described in the Examples Section. The data in FIGS. 4A and 4C-F represent mean±s.e.m.

FIG. 5A illustrates that food intake was measured in a two-day period and normalized to body weight. FIG. 5B illustrates whole body $O_2$ consumption in PGC-1α$^{+/+}$ (n=5) and PGC-1α$^{-/-}$ (n=5) mice as monitored by CLAMS. Shown is the averaged value over two days and three nights. *p<0.006. FIG. 5C depicts body temperature of 6 to 7-week old PGC-1α$^{+/+}$ (circle, n=6) and PGC-1α$^{-/-}$ (square, n=6) mice exposed to cold temperature (4° C.). *p<0.008. Data in FIGS.

5B-C represent mean±s.e.m. FIG. 5D illustrates gene expression in brown fat analyzed by quantitative real-time PCR. Intrascapular brown fat was dissected from PGC-1α$^{+/+}$ (filled box) and PGC-1α$^{-/-}$ (open box) mice maintained at 24° C. or after 5 hours of cold exposure at 4° C. Primers specific for 18S ribosomal RNA were used for normalization. FIG. 5E depicts analysis of skeletal muscle gene expression in wild-type (filled box) and PGC-1α deficient (open box) mice by quantitative real-time PCR. Quadriceps muscle was dissected from 4-month old male mice and frozen at -80° C. before RNA isolation and analysis. Primers specific for 18S ribosomal RNA were used for normalization. FIG. 5F depicts the activation of AMPK in PGC-1α$^{-/-}$ skeletal muscle. Tissue extracts were prepared from wild-type or PGC-1α null quadriceps muscle and analyzed by immunoblotting using antibodies specific for phosphorylated AMPK (pAMPK) and ACC (pACC), or an antibody that reacts with both phosphorylated and non-phosphorylated forms of AMPK.

FIG. 6A depicts a representative trace of movement monitoring for PGC-1α$^{+/+}$ (circles) and PGC-1α$^{-/-}$ (squares) mice over a period of three days. FIG. 6B depicts a representative trace of whole body $O_2$ consumption in PGC-1α$^{+/+}$ (circles) and PGC-1α$^{-/-}$ (squares) mice. N and D denote night and day periods, respectively. FIG. 6C is a graph depicting measurements of physical activity in 3-month old male mice with CLAMS. Shown is the average movement counts during the monitoring period. *$p<0.01$. FIG. 6D illustrates the limb clasping in PGC-1α$^{-/-}$ mice.

FIGS. 7A-B depict low magnification pictures showing cortex (ctx) and striatum (STR) of PGC-1α$^{+/+}$ mouse brain (FIG. 7A) and PGC-1α$^{-/-}$ mice (FIG. 7B) stained with Luxol fast blue and H&E. Note spongiform pathology predominantly in the striatum of the PGC-1α$^{-/-}$ mouse brain (red arrows). (Scalebar-200 μm). FIGS. 7C-D depict high magnification pictures of the striatum of wild type (FIG. 7C) and PGC-1α$^{-/-}$ brains (FIG. 7D) stained with Luxol fast blue/H&E. Shown are spongiform lesions in the striatum that are predominantly associated with the white matter. FIGS. 7E-F depicts immunohistochemical staining with an anti-GFAP antibody. Note abundant presence of reactive astrocytes (blue arrows) in the striatum of PGC-1α$^{-/-}$ mice (FIG. 7F), but not in wild type controls (FIG. 7E). FIGS. 7G-H depicts less striatal neurites are detected in the PGC-1α$^{-/-}$ brain (FIG. 7H) with a neurofilament heavy chain antibody compared to wild-type striatum (FIG. 7G). (Scalebar=200 μm).

FIG. 8A is a graph depicting analysis of mitochondrial gene expression in wild-type (filled box, n=4) and PGC-1α deficient (open box, n=6) mouse brain by real-time PCR. Whole brain was dissected from 3-month old male mice and frozen at -80° C. before RNA isolation and analysis. Primers specific for 18S ribosomal RNA were used for normalization. *$p<0.02$. FIG. 8B is a graph depicting real-time PCR analysis of non-mitochondrial genes involved in normal brain function as in (Figure A). *$p<0.02$.

FIG. 9A illustrates DNA that was isolated from neomycin-resistant ES cell clones, digested with BamHI and subjected to hybridization using probe L to detect homologous recombination and the presence of the flox allele. FIGS. 9B-D illustrate chimeric founders which were bred with wild-type C57/B16 mice to obtain offspring containing a germ-line PGC-1α flox allele.

Primers used for genotyping include SEQ ID NO:s 41 and 42 for wild type animals and SEQ ID NO:s 43 and 44 for knockout animals.

Figure 10:
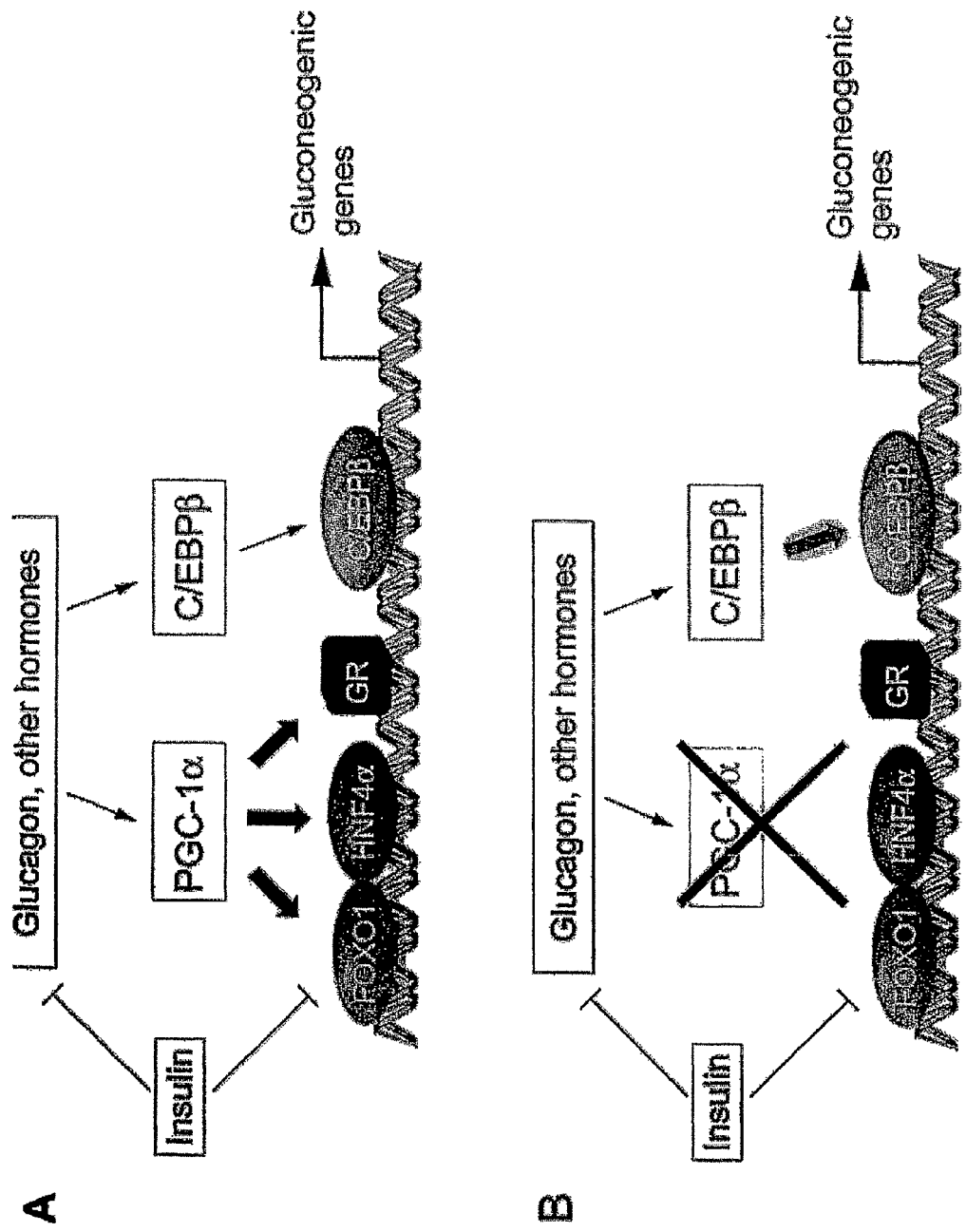

FIGS. 10A & B depict a model arising from these studies concerning the dietary control of gluconeogenesis.

DETAILED DESCRIPTION OF THE INVENTION

The present invention is based, at least in part, on the discovery that modulation of PGC-1α, e.g., PGC-1α expression or activity, leads to the modulation of lesion formation, e.g., brain lesion formation, neurological degeneration, and neurite formation. Therefore, in one aspect, the present invention provides methods for treating and/or preventing a neurological disease or disorder in a subject, e.g., a human subject, by administering to the subject a PGC-1α modulator, e.g., a PGC-1α agonist or antagonist.

PGC-1α null animals, e.g., mice, have been generated which display neurological defects, e.g., brain lesions, and histological abnormalities of the brain. The PGC-1αdeficient animals also display behavioral abnormalities, e.g., hyperactivity, and an increase in energy expenditure which correlates with their increased activity. Because of this increase in energy expenditure and hyperactivity, the PGC-1α-deficient animals are also resistant to obesity and insulin resistance.

It has been determined that the behavioral abnormalities of these animals are associated with lesions in the brain, e.g., the striatum, a brain area that plays a role in motor coordination. Without intending to be bound by theory, the prominent spongiform lesions in the striatum and in other areas of the PGC-1α null mouse brain suggest that abnormal CNS function is likely underlying the hyperactivity in the null animals. It is possible that many of these affected neurons play an inhibitory function with respect to physical movements of the mice, in that their loss is accompanied by increased movement and other neurological abnormalities. The PGC-1α-deficient animals also display alterations in the expression of genes involved in oxidative metabolism and neuronal function, and display impaired neurite growth. Furthermore, the hyperactivity displayed by mice deficient in PGC-1α with neurodegeneration is similar to the hyperactivity associated with neurological diseases and disorders, including, for example, Huntington's disease (HD).

Accordingly, in one aspect, the present invention is based, at least in part, on the discovery that PGC-1α functions in the development of neurological diseases and disorders, including neurodegenerative diseases and disorders and movement disorders, and is involved in mitochondrial function in the brain, lesion formation in the brain, neurite generation, and neurological degeneration. Therefore, modulation of PGC-1α, e.g., modulation of the expression or activity of PGC-1α and/or the pathways controlled by PGC-1α, through genetic or pharmacological methods, can improve brain function in neurological diseases and disorders or protect the brain from developing characteristics associated with neurological diseases or disorders, to thereby treat and/or prevent neurological diseases and disorders in a subject.

In another aspect, the present invention provides methods for modulating a neurological disease or disorder in a subject by administering a PGC-1α modulator to induce PGC-1α expression or activity. The present invention also provides methods for modulating mitochondrial function, e.g., in the brain, in a subject by administering a PGC-1α modulator to induce PGC-1α expression or activity. The present invention also provides methods for modulating lesion formation and neurite growth by administering a PGC-1α modulator to induce PGC-1α expression or activity.

In another aspect, the invention features methods for identifying a compound which modulates the expression or activity of PGC-1α. The methods include contacting PGC-1α or a cell expressing PGC-1α with a test compound and determining the effect of the test compound on the expression or activity of PGC-1α to, thereby, identify a compound which modulates, e.g., increases or decreases, PGC-1α expression or activity.

In another aspect, the invention features a non-human animal, in which the gene encoding the PGC-1α protein is misexpressed. In preferred embodiments, the non-human animal is a transgenic animal. The transgenic non-human animal can be, without limitation, a mammal; a bird; a reptile or an amphibian. Suitable mammals for uses described herein include, e.g., ruminants, ungulates, domesticated mammals, and dairy animals. Other suitable animals include goats, sheep, camels, cows, pigs, horses, oxen, llamas, chickens, geese, and turkeys. Methods for the preparation and use of such animals are known in the art. A protocol for the production of a transgenic pig can be found in White and Yannoutsos, *Current Topics in Complement Research: 64th Forum in Immunology*, pp. 88-94; U.S. Pat. Nos. 5,523,226; 5,573,933; PCT Application WO93/25071; and PCT Application WO95/04744. A protocol for the production of a transgenic rat can be found in Bader and Ganten, *Clinical and Experimental Pharmacology and Physiology, Supp.* 3:S81-S87, 1996. A protocol for the production of a transgenic cow can be found in *Transgenic Animal Technology, A Handbook*, 1994, ed., Carl A. Pinkert, Academic Press, Inc. A protocol for the production of a transgenic sheep can be found in *Transgenic Animal Technology, A Handbook*, 1994, ed., Carl A. Pinkert, Academic Press, Inc.

Definitions

As used herein, the term "modulator of PGC-1α expression or activity" includes a compound or agent that is capable of modulating or regulating PGC-1α expression or at least one PGC-1α activity, as described herein. A modulator of PGC-1α expression or activity can be an inducer of PGC-1α expression or activity or an inhibitor of PGC-1α expression or activity. As used herein, an "inducer or agonist of PGC-1α activity" agonizes, stimulates, enhances, and/or mimics a PGC-1α activity, either completely or partially. An "inducer or agonist of PGC-1α expression" increases, enhances, or stimulates PGC-1α expression, either completely or partially, directly or indirectly. As used herein, an "inhibitor or antagonist of PGC-1α activity" antagonizes, reduces, or blocks PGC-1α activity, either completely or partially. An "inhibitor or antagonist of PGC-1α expression" reduces or blocks PGC-1α expression, either completely or partially, directly or indirectly. Examples of PGC-1α inhibitors include small molecules, antisense PGC-1α nucleic acid molecules, ribozymes, siRNA molecules, and anti-PGC-1α antibodies. Examples of PGC-1α inducers include PGC-1α mimetics, e.g., peptidomimetics, small molecules, nucleic acid molecules encoding PGC-1α, and PGC-1α proteins or fragments thereof.

As used interchangeably herein, a "PGC-1α activity", "biological activity of PGC-1α" or "functional activity of PGC-1α" refers to an activity exerted by a PGC-1α polypeptide or nucleic acid molecule on a PGC-1α responsive molecule, cell, or tissue, as determined in vitro and/or in vivo, according to standard techniques. In an exemplary embodiment, a PGC-1α activity is the ability to modulate mitochondrial function, e.g., oxidative metabolism. In another embodiment, PGC-1α activity is the ability to modulate the activity or expression of a mitochondrial gene, e.g., LDH2, Ndufb5, COX6a1, or ATP5j. In yet another embodiment, a PGC-1α activity is the ability to modulate the expression or activity of a neuronal gene, e.g., NF-H, NF-M, MOBP, ATPa1, or ATP1a2. In a further embodiment, PGC-1α activity is the ability to modulate lesion formation, e.g., brain lesion formation, in, for example, the striatum. In yet another embodiment, PGC-1α activity is the ability to modulate neurite formation and/or neuronal degeneration. In another embodiment, PGC-1α activity is the ability to modulate body weight and energy expenditure, e.g., via hyperactivity. In a further embodiment, PGC-1α activity is the ability to modulate gluconeogenesis, e.g., via coactivation of Foxo1, HNF4a, GR, and other factors. In still another embodiment, PGC-1α activity is the ability to modulate interact with (e.g., bind to) nuclear hormone receptors. In a preferred embodiment, PGC-1α activity is the ability to modulate neurological diseases or disorders, e.g., neurodegenerative diseases or disorders, in a subject.

As used herein, the term "neurological disease or disorder" includes any disease, disorder, or condition which is caused by or related to dysfunction or deficiency of the central nervous system, including, but not limited to mitochondrial dysfunction, lesion formation, neural degeneration, or misregulation or modulation of any central nervous system specific pathway or central nervous system specific activity. Neurological diseases or disorders include neurodegenerative and cognitive disorders. Examples of neurological diseases and disorders include, but are not limited to, Alzheimer's disease, Parkinson's disease, Huntington's disease, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis (MS), amyotrophic lateral sclerosis (ALS), progressive supranuclear palsy (PSP), epilepsy, Creutzfeldt-Jakob disease, deafness-dytonia syndrome, Leigh syndrome, Leber hereditary optic neuropathy (LHON), parkinsonism, dystonia, motor neuron disease, neuropathy-ataxia and retinitis pimentosa (NARP), maternal inherited Leigh syndrome (MILS), Friedreich ataxia, hereditary spastic paraplegia, Mohr-Tranebjaerg syndrome, Wilson disease, sporatic Alzheimer's disease, sporadic amyotrophic lateral sclerosis, sporadic Parkinson's disease, autonomic function disorders, hypertension, sleep disorders, neuropsychiatric disorders, depression, schizophrenia, schizoaffective disorder, korsakoff's psychosis, mania, anxiety disorders, phobic disorder, learning or memory disorders, amnesia or age-related memory loss, attention deficit disorder, dysthymic disorder, major depressive disorder, obsessive-compulsive disorder, psychoactive substance use disorders, panic disorder, bipolar affective disorder, severe bipolar affective (mood) disorder (BP-1), migraines, hyperactivity and movement disorders. As used herein, the term "movement disorder" includes neurological diseases or disorders that involve the motor and movement systems, resulting in a range of abnormalities that affect the speed, quality and ease of movement. Movement disorders are often caused by or related to abnormalities in brain structure and/or function. Movement disorders include, but are not limited to (i) tremors: including, but not limited to, the tremor associated with Parkinson's Disease, physiologic tremor, benign familial tremor, cerebellar tremor, rubral tremor, toxic tremor, metabolic tremor, and senile tremor; (ii) chorea, including, but not limited to, chorea associated with Huntington's Disease, Wilson's Disease, ataxia telangiectasia, infection, drug ingestion, or metabolic, vascular or endocrine etiology (e.g., chorea gravidarum or thyrotoxicosis); (iii) ballism (defined herein as abruptly beginning, repetitive, wide, flinging movements affecting predominantly the proximal limb and girdle muscles); (iv) athetosis (defined herein as relatively slow, twisting, writhing, snake-like movements and postures involving the trunk, neck, face and extremities); (v) dystonia (defined herein as a movement disorder consisting of twisting, turning tonic skeletal muscle contractions, most, but not all of which are initiated distally); (vi) paroxysmal choreoathetosis and tonic spasm; (vii) tics (defined herein as sudden, behaviorally related, irregular, stereotyped, repetitive movements of variable complexity); (viii) tardive dyskinesia; (ix) akathesia, (x) muscle rigidity, defined herein as resistance of a muscle to stretch; (xi) postural instability; (xii) bradykinesia; (xiii) difficulty in initiating movements; (xiv) muscle cramps; (xv) dyskinesias and (xvi) myoclonus.

The term "mitochondrial function" includes any cellular activity carried out by mitochondria or mitochondrial genes, including mitochondria or mitochondrial genes in brain cells, e.g., neurons. For example, mitochondria play a role in a number of important cellular functions including, for example, oxidative energy metabolism, amino acid biosynthesis, fatty acid oxidation, steroid metabolism, and apoptosis. "Mitochondrial dysfunction" includes any failure or deficiency of mitochondria or mitochondrial genes to carry out a mitochondrial function, e.g., oxidative energy metabolism.

The term "treatment", as used herein, is defined as the application or administration of a therapeutic agent to a patient, or application or administration of a therapeutic agent to an isolated tissue or cell line from a patient, who has a disease or disorder, a symptom of a disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, small molecules, peptides, peptidomimetics, nucleic acid molecules, antibodies, ribozymes, siRNA molecules, and sense and antisense oligonucleotides described herein.

As used herein, "administering a treatment to an animal or cell" is intended to refer to dispensing, delivering or applying a treatment to an animal or cell. In terms of the therapeutic agent, the term "administering" is intended to refer to contacting or dispensing, delivering or applying the therapeutic agent to an animal by any suitable route for delivery of the therapeutic agent to the desired location in the animal, including delivery by either the parenteral or oral route, intramuscular injection, subcutaneous/intradermal injection, intravenous injection, buccal administration, transdermal delivery and administration by the intranasal or respiratory tract route.

As used herein, the term "compound" includes any agent, e.g., peptide, peptidomimetic, small molecule, or other drug, which binds to a PGC-1α protein or has a stimulatory or inhibitory effect on, for example, PGC-1α expression or PGC-1α activity.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter, e.g., a brain cell. PGC-1α may be expressed in specific portions of the brain, e.g., in an animal model or in a subject to treat or prevent a neurological disease or disorder. Furthermore, in another embodiment, tissue specific PGC-1α knockout animal models may also be produced wherein PGC-1α is flanked (or "foxed") by two or more lox sites, most commonly loxP sites, and is excised using the Cre recombinase protein, as is known in the art and described herein In one embodiment, a knock-out animal is used to evaluate the function of PGC-1α in a specific nervous system tissue.

The term "polymorphism" refers to the coexistence of more than one form of a gene or portion thereof. A portion of a gene of which there are at least two different forms, i.e., two different nucleotide sequences, is referred to as a "polymorphic region of a gene." A polymorphic locus can be a single nucleotide, the identity of which differs in the other alleles. A polymorphic locus can also be more than one nucleotide long. The allelic form occurring most frequently in a selected population is often referred to as the reference and/or wildtype form. Other allelic forms are typically designated, alternative, or variant alleles. Diploid organisms may be homozygous or heterozygous for allelic forms. A diallelic or biallelic polymorphism has two forms. A trialleleic polymorphism has three forms.

The term "single nucleotide polymorphism" (SNP) refers to a polymorphic site occupied by a single nucleotide, which is the site of variation between allelic sequences. A SNP usually arises due to substitution of one nucleotide for another at the polymorphic site. SNPs can also arise from a deletion of a nucleotide or an insertion of a nucleotide relative to a reference allele. Typically, the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site.

SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect.

The term "linkage" describes the tendency of genes, alleles, loci or genetic markers to be inherited together as a result of their location on the same chromosome. It can be measured by percent recombination between the two genes, alleles, loci, or genetic markers. The term "linkage disequilibrium," also referred to herein as "LD," refers to a greater than random association between specific alleles at two marker loci within a particular population. In general, linkage disequilibrium decreases with an increase in physical distance. If linkage disequilibrium exists between two markers, or SNPs, then the genotypic information at one marker, or SNP, can be used to make probabilistic predictions about the genotype of the second marker.

As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal. Transgenic animals also include inducible transgenic animals, such as those described in, for example, Chan I. T., et al. (2004) *J Clin Invest.* 113(4):528-38 and Chin L. et al (1999) *Nature* 400(6743):468-72.

As used herein, the term "rodent" refers to all members of the phylogenetic order Rodentia.

As used herein, the term "misexpression" includes a non-wild type pattern of gene expression. Expression as used herein includes transcriptional, post transcriptional, e.g., mRNA stability, translational, and post translational stages. Misexpression includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences.

As used herein, the term "knockout" refers to an animal or cell therefrom, in which the insertion of a transgene disrupts an endogenous gene in the animal or cell therefrom. This disruption can essentially eliminate PGC-1α in the animal or cell.

In preferred embodiments, misexpression of the gene encoding the PGC-1α protein is caused by disruption of the PGC-1α gene. For example, the PGC-1α gene can be disrupted through removal of DNA encoding all or part of the protein.

In preferred embodiments, the animal can be heterozygous or homozygous for a misexpressed PGC-1α gene, e.g., it can be a transgenic animal heterozygous or homozygous for a PGC-1α transgene.

In preferred embodiments, the animal is a transgenic mouse with a transgenic disruption of the PGC-1α gene, preferably an insertion or deletion, which inactivates the gene product.

In another aspect, the invention features, a nucleic acid molecule which, when introduced into an animal or cell, results in the misexpression of the PGC-1α gene in the animal or cell. In preferred embodiments, the nucleic acid molecule includes a PGC-1α nucleotide sequence which includes a disruption, e.g., an insertion or deletion and preferably the insertion of a marker sequence.

As used herein, "disruption of a gene" refers to a change in the gene sequence, e.g., a change in the coding region. Disruption includes insertions, deletions, point mutations, and rearrangements, e.g., inversions. The disruption can occur in a region of the native PGC-1α DNA sequence (e.g., one or more exons) and/or the promoter region of the gene so as to decrease or prevent expression of the gene in a cell as compared to the wild-type or naturally occurring sequence of the gene. The "disruption" can be induced by classical random mutation or by site directed methods. Disruptions can be transgenically introduced. The deletion of an entire gene is a disruption. Preferred disruptions reduce PGC-1α levels to about 50% of wild type, in heterozygotes or essentially eliminate PGC-1α in homozygotes.

As used herein, the term "transgenic cell" refers to a cell containing a transgene.

Various aspects of the invention are described in further detail in the following subsections:

I. Screening Assays:

The invention provides a method (also referred to herein as a "screening assay") for identifying modulators, i.e., candidate or test compounds or agents (e.g., peptides, peptidomimetics, small molecules (organic or inorganic) or other drugs) which bind to PGC-1α proteins, have a stimulatory or inhibitory effect on, for example, PGC-1α expression or PGC-1α activity, or have a stimulatory or inhibitory effect on, for example, the expression or activity of a PGC-1α substrate. Compounds identified using assays described herein may be useful for modulating PGC-1α expression or activity, e.g., increasing PGC-1α expression or activity. Thus, these compounds would be useful for treating or preventing neurological diseases or disorders.

These assays are designed to identify compounds that bind to or interact with a PGC-1α protein, or bind to or interact with other intracellular or extracellular proteins that interact with or modulate a PGC-1α protein. Such compounds may include, but are not limited to peptides, antibodies, nucleic acid molecules, siRNA molecules, or small organic or inorganic compounds. Such compounds may also include other cellular proteins.

Compounds identified via assays such as those described herein may be useful, for example, modulating PGC-1α, e.g., by causing increased PGC-1α expression or activity and, for example, decreased lesion formation, increased neurite growth and decreased mitochondrial dysfunction. Thus, these compounds would be useful for treating or preventing a neurological disease or disorder. In instances whereby increased PGC-1α activity or expression is desired compounds that interact with the PGC-1α protein may include compounds which accentuate or amplify the expression or activity of PGC-1α protein. Such compounds would bring about an effective increase in the level of PGC-1α protein activity, thus identifying, treating or preventing neurological diseases or disorders. For example, a partial agonist or an agonist administered in a dosage or for a length of time to increase expression or activity of PGC-1α would act to increase mitochondrial function, reduce lesion formation, induce neurite growth, and treat or prevent a neurological disease or disorder. Alternatively, in instances whereby decreased PGC-1α activity or expression is desired, e.g., to induce symptoms of a neurological disease or disorder in an animal model or to induce weight loss, compounds that interact with the PGC-1α protein may include compounds which inhibit or suppress the expression or activity of PGC-1α protein. Such compounds would bring about an effective decrease in the level of PGC- 1α protein activity, thus acting as an inducer for a neurological disease or disorder, depending on the dosage of the compound and the length of time the compound is administered.

In one embodiment, the invention provides assays for screening candidate or test compounds which are substrates of or interact with a PGC-1α protein or polypeptide or biologically active portion thereof. In another embodiment, the invention provides assays for screening candidate or test compounds which bind to or modulate the activity of a PGC-1α protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a PGC-1α protein or biologically active portion thereof is contacted with a test compound and the ability of the test compound to modulate PGC-1α activity is determined. Determining the ability of the test compound to modulate PGC-1α activity can be accomplished by monitoring, for example, intracellular calcium, $IP_3$, cAMP, or diacylglycerol concentration, or the phosphorylation profile of intracellular proteins, or the level of transcription of downstream genes. The cell can be of mammalian origin, e.g., a neuron. In one embodiment, compounds that interact with PGC-1α binding site can be screened for their ability to function as ligands, i.e., to bind to PGC-1α binding site and modulate transcription or modulate a signal transduction pathway. Identification of PGC-1α ligands, and measuring the activity of the ligand-PGC-1α complex, leads to the identification of modulators (e.g., antagonists or agonists) of this interaction. Such modulators may be useful in the treatment and prevention of a neurological disease or disorder modulation of PGC-1α, e.g., by causing increased expression or activity of PGC-1α.

The ability of the test compound to modulate PGC-1α binding to a substrate or to bind to PGC-1α can also be determined. Determining the ability of the test compound to modulate PGC-1α binding to a substrate can be accomplished, for example, by coupling the PGC-1α substrate with a radioisotope or enzymatic label such that binding of the PGC-1α substrate to PGC-1α can be determined by detecting the labeled PGC-1α substrate in a complex. PGC-1α could also be coupled with a radioisotope or enzymatic label to monitor the ability of a test compound to modulate PGC-1α binding to a PGC-1α substrate in a complex. Determining the ability of the test compound to bind PGC-1α can be accomplished, for example, by coupling the compound with a radioisotope or enzymatic label such that binding of the compound to PGC-1α can be determined by detecting the labeled PGC-1α compound in a complex. For example, compounds (e.g., PGC-1α ligands or substrates) can be labeled with $^{125}I$, $^{35}S$, $^{14}C$, or $^3H$, either directly or indirectly, and the radioisotope detected by direct counting of radioemmission or by scintillation counting. Compounds can further be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a PGC-1α ligand or substrate) to interact with PGC-1α without the labeling of any of the interactants. For example, a microphysiometer can be used to detect the interaction of a compound with PGC-1α without the labeling of either the compound or the PGC-1α (McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PGC-1α.

In another embodiment, an assay is a cell-based assay comprising contacting a cell expressing a PGC-1α target molecule (e.g., a PGC-1α substrate) with a test compound and determining the ability of the test compound to modulate (e.g., stimulate or inhibit) the activity of the PGC-1α target molecule. Determining the ability of the test compound to modulate the activity of a PGC-1α target molecule can be accomplished, for example, by determining the ability of the PGC-1α protein to bind to or interact with the PGC-1α target molecule.

Determining the ability of the PGC-1α protein or a biologically active fragment thereof, to bind to or interact with a PGC-1α target molecule can be accomplished by one of the methods described above for determining direct binding. In a preferred embodiment, determining the ability of the PGC-1α protein to bind to or interact with a PGC-1α target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, cAMP), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., gene expression).

In yet another embodiment, an assay of the present invention is a cell-free assay in which a PGC-1α protein or biologically active portion thereof, is contacted with a test compound and the ability of the test compound to bind to the PGC-1α protein or biologically active portion thereof is determined. Preferred biologically active portions of the PGC-1α proteins to be used in assays of the present invention include fragments which participate in interactions with non-PGC-1α molecules, e.g., fragments with high surface probability scores. Binding of the test compound to the PGC-1α protein can be determined either directly or indirectly as described above. In a preferred embodiment, the assay includes contacting the PGC-1α protein or biologically active portion thereof with a known compound which binds PGC-1α to form an assay mixture, contacting the assay mixture with a test compound, and determining the ability of the test compound to interact with a PGC-1α protein, wherein determining the ability of the test compound to interact with a PGC-1α protein comprises determining the ability of the test compound to preferentially bind to PGC-1α or biologically active portion thereof as compared to the known compound. Compounds that modulate the interaction of PGC-1α with a known target protein may be useful in regulating the activity of a PGC-1α protein, especially a mutant PGC-1α protein.

In another embodiment, the assay is a cell-free assay in which a PGC-1α protein or biologically active portion thereof is contacted with a test compound and the ability of the test compound to modulate (e.g., stimulate or inhibit) the activity of the PGC-1α protein or biologically active portion thereof is determined. Determining the ability of the test compound to modulate the activity of a PGC-1α protein can be accomplished, for example, by determining the ability of the PGC-1α protein to bind to a PGC-1α target molecule by one of the methods described above for determining direct binding. Determining the ability of the PGC-1α protein to bind to a PGC-1α target molecule can also be accomplished using a technology such as real-time Biomolecular Interaction Analysis (BIA) (Sjolander, S, and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, determining the ability of the test compound to modulate the activity of a PGC-1α protein can be accomplished by determining the ability of the PGC-1α protein to further modulate the activity of a downstream effector of a PGC-1α target molecule. For example, the activity of the effector molecule on an appropriate target can be determined or the binding of the effector to an appropriate target can be determined as previously described.

In yet another embodiment, the cell-free assay involves contacting a PGC-1α protein or biologically active portion thereof with a known compound which binds the PGC-1α protein to form an assay mixture, contacting the assay mixture with a test compound, and determining the ability of the test compound to interact with the PGC-1α protein, wherein determining the ability of the test compound to interact with the PGC-1α protein comprises determining the ability of the PGC-1α protein to preferentially bind to or modulate the activity of a PGC-1α target molecule.

In more than one embodiment of the above assay methods of the present invention, it may be desirable to immobilize either PGC-1α or its target molecule to facilitate separation of complexed from uncomplexed forms of one or both of the proteins, as well as to accommodate automation of the assay. Binding of a test compound to a PGC-1α protein, or interaction of a PGC-1α protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PGC-1α fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or PGC-1α protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PGC-1α binding or activity determined using standard techniques.

Other techniques for immobilizing proteins on matrices can also be used in the screening assays of the invention. For example, either a PGC-1α protein or a PGC-1α target molecule can be immobilized utilizing conjugation of biotin and streptavidin. Biotinylated PGC-1α protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PGC-1α protein or target molecules but which do not interfere with binding of the PGC-1α protein to its target molecule can be derivatized to the wells of the plate, and unbound target or PGC-1α protein trapped in the wells by antibody conjugation. Methods for detecting such complexes, in addition to those described above for the GST-immobilized complexes, include immunodetection of complexes using antibodies reactive with the PGC-1α protein or target molecule, as well as enzyme-linked assays which rely on detecting an enzymatic activity associated with the PGC-1α protein or target molecule.

In another embodiment, modulators of PGC-1α expression are identified in a method wherein a cell is contacted with a candidate compound and the expression of PGC-1α mRNA or protein in the cell is determined. The level of expression of PGC-1α mRNA or protein in the presence of the candidate compound is compared to the level of expression of PGC-1α mRNA or protein in the absence of the candidate compound. The candidate compound can then be identified as a modulator of PGC-1α expression based on this comparison. For example, when expression of PGC-1α mRNA or protein is greater (statistically significantly greater) in the presence of the candidate compound than in its absence, the candidate compound is identified as a stimulator of PGC-1α mRNA or protein expression. Alternatively, when expression of PGC-1α mRNA or protein is less (statistically significantly less) in the presence of the candidate compound than in its absence, the candidate compound is identified as an inhibitor of PGC-1α mRNA or protein expression. The level of PGC-1α mRNA or protein expression in the cells can be determined by methods described herein for detecting PGC-1α mRNA or protein.

In yet another aspect of the invention, the PGC-1α proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with PGC-1α ("PGC-1α-binding proteins" or "PGC-1α-bp") and are involved in PGC-1α activity. Such PGC-1α-binding proteins are also likely to be involved in the propagation of signals by the PGC-1α proteins or PGC-1α targets as, for example, downstream elements of a PGC-1α-mediated signaling pathway. Alternatively, such PGC-1α-binding proteins are likely to be PGC-1α inhibitors.

The two-hybrid system is based on the modular nature of most transcription factors, which consist of separable DNA-binding and activation domains. Briefly, the assay utilizes two different DNA constructs. In one construct, the gene that codes for a PGC-1α protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PGC-1α-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PGC-1α protein.

In a further embodiment, assays may be devised through the use of the invention for the purpose of identifying compounds which modulate (e.g., affect either positively or negatively) interactions between PGC-1α and its substrates and/or binding partners. Such compounds can include, but are not limited to, molecules such as small molecules, antibodies, peptides, hormones, oligonucleotides, nucleic acids, and analogs thereof. Such compounds may also be obtained from any available source, including systematic libraries of natural and/or synthetic compounds. The preferred assay components for use in this embodiment is a transcriptional coactivator, PGC-1α identified herein, the known binding partner and/or substrate of same, and the test compound. Test compounds can be supplied from any source.

The basic principle of the assay systems used to identify compounds that interfere with the interaction between PGC-1α and its binding partner involves preparing a reaction mixture containing PGC-1α and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of PGC-1α and its binding partner. Control reaction mixtures are incubated without the test compound or with a placebo. The formation of any complexes between PGC-1α and its binding partner is then detected. The formation of a complex in the control reaction, but less or no such formation in the reaction mixture containing the test compound, indicates that the compound interferes with the interaction of PGC-1α and its binding partner. Conversely, the formation of more complex in the presence of compound than in the control reaction indicates that the compound may enhance interaction of PGC-1α and its binding partner.

The assay for compounds that interfere with the interaction of PGC-1α with its binding partner may be conducted in a heterogeneous or homogeneous format. Heterogeneous assays involve anchoring either PGC-1α or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between PGC-1α and the binding partners (e.g., by competition) can be identified by conducting the reaction in the presence of the test substance, i.e., by adding the test substance to the reaction mixture prior to or simultaneously with PGC-1α and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either PGC-1α or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of PGC-1α or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/PGC-1α fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed PGC-1α or its binding partner, and the mixture incubated under conditions conducive to complex formation (e.g., physiological conditions). Following incubation, the beads or microtiter plate wells are washed to remove any unbound assay components; the immobilized complex assessed either directly or indirectly, for example, as described above. Alternatively, the complexes can be dissociated from the matrix, and the level of PGC-1α binding or activity determined using standard techniques.

Other techniques for immobilizing proteins on matrices can also be used in the screening assays of the invention. For example, either PGC-1α or PGC-1α binding partner can be immobilized utilizing conjugation of biotin and streptavidin. Biotinylated PGC-1α protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format; for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between PGC-1α and its binding partner.

Also within the scope of the present invention are methods for direct detection of interactions between PGC-1α and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., PGC-1α or test compound) such that its emitted fluorescent energy will be absorbed by a fluorescent label on a second, 'acceptor' molecule (e.g., PGC-1α or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between PGC-1α and its binding partner can be identified in controlled assays.

In another embodiment, modulators of PGC-1α expression are identified in a method wherein a cell is contacted with a candidate compound and the expression of mRNA or protein, corresponding to a PGC-1α in the cell, is determined. The level of expression of mRNA or protein in the presence of the candidate compound is compared to the level of expression of mRNA or protein in the absence of the candidate compound. The candidate compound can then be identified as a modulator of PGC-1α expression based on this comparison. For example, when expression of PGC-1α mRNA or protein is greater (statistically significantly greater) in the presence of the candidate compound than in its absence, the candidate compound is identified as a stimulator of PGC-1α mRNA or protein expression. Conversely, when expression of PGC-1α mRNA or protein is less (statistically significantly less) in the presence of the candidate compound than in its absence, the candidate compound is identified as an inhibitor of PGC-1α mRNA or protein expression. The level of PGC-1α mRNA or protein expression in the cells can be determined by methods described herein for detecting PGC-1α mRNA or protein.

In another aspect, the invention pertains to a combination of two or more of the assays described herein. For example, a modulating agent can be identified using a cell-based or a cell free assay, and the ability of the agent to modulate the activity of a PGC-1α protein can be confirmed in vivo, e.g., in an animal such as an animal model for a neurological disease or disorder, as described herein, or described in, for example, Sathasivam K et al. *Philos Trans R Soc Lond B Biol Sci.* 1999 Jun. 29; 354(1386):963-9; Bates G P, et al. *Hum Mol Genet.* 1997; 6(10):1633-7; Shaw C A et al *Neurosci Biobehav Rev.* 2003 October; 27(6):493-505; Menalled L B *Trends Pharmacol Sci.* 2002 January; 23(1):32-9; Legare M E et al. *Genet Mol Res.* 2003 Sep. 30; 2(3):288-94; Oiwa Y *J Neurosurg.*

2003 January; 98(1):136-44; and Bard F et al. *Nat Med.* 2000 August; 6(8):916-9, the contents of which are incorporated by reference herein.

This invention further pertains to novel agents identified by the above-described screening assays. Accordingly, it is within the scope of this invention to further use an agent identified as described herein in an appropriate animal model. For example, an agent identified as described herein (e.g., a small molecule, an antisense PGC-1α nucleic acid molecule, a PGC-1α-specific antibody, or a PGC-1α-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for a compound capable of treating or preventing a neurological disease or disorder comprising the ability of the compound to modulate PGC-1α nucleic acid expression or PGC-1α polypeptide activity, thereby identifying a compound capable of treating or preventing a neurological disease or disorder. Cell-based and animal model-based assays for the identification of compounds exhibiting such an ability to treat or prevent a neurological disease or disorder described herein.

In one aspect, cell-based systems, as described herein, may be used to identify compounds which may act to modulate PGC-1α nucleic acid expression or PGC-1α polypeptide activity or treat neurological diseases or disorders. For example, such cell systems may be exposed to a compound, suspected of exhibiting an ability to modulate PGC-1α or treat or prevent a neurological disease or disorder, at a sufficient concentration and for a time sufficient to elicit such an amelioration of disease symptoms in the exposed cells. After exposure, the cells are examined to determine whether one or more of the disease phenotypes, e.g., Huntington's Disease, for example, has been altered to resemble a more normal or more wild type disease phenotype.

In addition, animal-based disease systems, such as those described herein, may be used to identify compounds which may act to modulate PGC-1α nucleic acid expression or PGC-1α polypeptide activity or treat neurological diseases or disorders. Such animal models may be used as test substrates for the identification of drugs, pharmaceuticals, therapies, and interventions which may be effective in modulating PGC-1α, treating or preventing neurological diseases or disorders e.g., Huntington's disease.

In one embodiment, compounds which are capable of treating or preventing a neurological disease or disorder are identified by assaying the ability of the compound to modulate PGC-1α nucleic acid expression or PGC-1α polypeptide activity is determined by detecting modulation of mitochondrial function, e.g. mitochondrial function in the brain. Furthermore, the invention includes identifying compound which have the ability to modulate PGC-1α nucleic acid expression or PGC-1α polypeptide activity is determined by detecting modulation in the expression or activity of mitochondrial genes, e.g., LDH2, Ndufb5, COX6a1, and ATP5j.

In still another embodiment, compounds which are capable of treating or preventing a neurological disease or disorder are identified by assaying the ability of the compound to modulate PGC-1α is determined by detecting modulation in the expression or activity of neuronal genes, e.g., NF-H, NF-M, MOBP, ATPa1, and ATP1a2.

Additionally, gene expression patterns may be utilized to assess the ability of a compound to modulate PGC-1 e.g., by causing increased PGC-1α expression or activity. Thus, these compounds would be useful for treating, preventing, or assessing a neurological disease or disorder. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Gene expression profiles may be generated, for example, by utilizing a differential display procedure, Northern analysis and/or RT-PCR. In one embodiment, PGC-1α gene sequences may be used as probes and/or PCR primers for the generation and corroboration of such gene expression profiles.

Gene expression profiles may be characterized for known states within the cell- and/or animal-based model systems. Subsequently, these known gene expression profiles may be compared to ascertain the effect a test compound has to modify such gene expression profiles, and to cause the profile to more closely resemble that of a more desirable profile.

II. Methods of Treatment:

The present invention provides for both prophylactic and therapeutic methods of treating or preventing a neurological disease or disorder in a subject, e.g., a human, at risk of (or susceptible to) a neurological disease or disorder, by administering to said subject a PGC-1α modulator, such that the neurological disease or disorder is treated or prevented. In a preferred embodiment, which includes both prophylactic and therapeutic methods, the PGC-1α modulator is administered by in a pharmaceutically acceptable formulation.

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring a subject's prophylactic or therapeutic treatment with either the PGC-1α molecules of the present invention or PGC-1α modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the invention provides a method for treating or preventing a neurological disease or disorder by administering to a subject an agent which modulates PGC-1α expression or PGC-1α activity. The invention also provides methods for modulating the formation of brain lesions, neurodegeneration, and neurite growth in a subject. Subjects at risk for a neurological disease or disorder can be identified by, for example, any or a combination of the diagnostic or prognostic assays described herein. Administration of a prophylactic agent can occur prior to the manifestation of symptoms characteristic of a neurological disease or disorder, such that the neurological disease or disorder or symptom thereof, e.g., hyperactivity, is prevented or, alternatively, delayed in its progression. Depending on the type of PGC-1α aberrancy, for example, a PGC-1α agonist or PGC-1α antagonist agent can be used for treating the subject. The appropriate agent can be determined based on screening assays described herein.

B. Therapeutic Methods

The present invention provides methods for modulating PGC-1α in a subject by administering a PGC-1α modulator to either induce or inhibit PGC-1α expression or activity. In one embodiment, PGC-1α expression or activity is increased by administering an inducer or agonist of PGC-1α expression or activity, thereby modulating lesion formation, e.g., brain lesion formation, mitochondrial function, neurite growth, and/or neurodegeneration, and treating or preventing a neurological disease or disorder.

Accordingly, another aspect of the invention pertains to methods of modulating PGC-1α expression or activity for therapeutic purposes and for use in treatment of neurological diseases or disorders. In an exemplary embodiment, the modulatory method of the invention involves contacting a cell with a PGC-1α or agent that modulates one or more of the activities of PGC-1α protein activity associated with a neurological disease or disorder (e.g., modulation of mitochondrial function, brain lesion formation, neurite growth or neuronal degeneration). An agent that modulates PGC-1α protein activity can be an agent as described herein, such as a nucleic acid or a protein, an siRNA targeting PGC-1α mRNA, a naturally-occurring target molecule of a PGC-1α protein (e.g., a PGC-1α ligand or substrate), a PGC-1α antibody, a PGC-1α agonist or antagonist, a peptidomimetic of a PGC-1α agonist or antagonist, or other small molecule. In one embodiment, the agent stimulates one or more PGC-1α activities. Examples of such stimulatory agents include active PGC-1α protein, a nucleic acid molecule encoding PGC-1α, or a small molecule agonist, or mimetic, e.g., a peptidomimetic. In another embodiment, the agent inhibits one or more PGC-1α activities. Examples of such inhibitory agents include antisense PGC-1α nucleic acid molecules, siRNA molecules, anti-PGC-1α antibodies, small molecules, and PGC-1α inhibitors. These modulatory methods can be performed in vitro (e.g., by culturing the cell with the agent) or, alternatively, in vivo (e.g., by administering the agent to a subject). In one embodiment, the method involves administering an agent (e.g., an agent identified by a screening assay described herein), or combination of agents that modulates (e.g., upregulates or downregulates) PGC-1α expression or activity. In another embodiment, the method involves administering a PGC-1α protein or nucleic acid molecule as therapy to compensate for reduced, aberrant, or unwanted PGC-1α expression or activity.

Stimulation of PGC-1α activity is desirable in situations in which PGC-1α is abnormally downregulated and/or in which increased PGC-1α activity is likely to have a beneficial effect, e.g., as a treatment for a neurological disease or disorder. Likewise, inhibition of PGC-1α activity is desirable in situations in which PGC-1α is abnormally upregulated and/or in which decreased PGC-1α activity is likely to have a beneficial effect, e.g., to effect the creation of an animal model for a neurological disease or disorder, e.g., a non-human animal transgenic in which PGC-1α is misexpressed, or to modulate body weight in a subject, e.g., to treat or prevent obesity.

(i) Methods for Increasing PGC-1α Expression or Activity

Increasing PGC-1α expression or activity leads to treatment or prevention of a neurological disease or disorder, therefore providing a method for treating, preventing, and assessing a neurological disease or disorder. A variety of techniques may be used to increase the expression, synthesis, or activity of PGC-1α.

Described in this section are methods whereby the level PGC-1α activity may be increased, for example, by either increasing the level of PGC-1α gene expression or by increasing the level of active PGC-1α protein which is present.

For example, a PGC-1α protein may be administered to a subject. Any of the techniques discussed below may be used for such administration. One of skill in the art will readily know how to determine the concentration of effective, non-toxic doses of the PGC-1α protein, utilizing techniques such as those described below.

Additionally, RNA sequences encoding a PGC-1α protein may be directly administered to a subject, at a concentration sufficient to produce a level of PGC-1α protein such that PGC-1α is modulated. Any of the techniques discussed below, which achieve intracellular administration of compounds, such as, for example, liposome administration, may be used for the administration of such RNA molecules. The RNA molecules may be produced, for example, by recombinant techniques such as those described herein. Other pharmaceutical compositions, medications, or therapeutics may be used in combination with the PGC-1α agonists described herein. Further, subjects may be treated by gene replacement therapy, resulting in permanent modulation of PGC-1α. One or more copies of a PGC-1α gene, or a portion thereof, that directs the production of a normal PGC-1α protein with PGC-1α function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of PGC-1α gene sequences into human cells. Furthermore, expression or activity of transcriptional activators which act upon PGC-1α may be increased to thereby increase expression and activity of PGC-1α. Small molecules which induce PGC-1α expression or activity, either directly or indirectly may also be used. In one embodiment, a small molecule functions to disrupt a protein-protein interaction between PGC-1α and a target molecule or ligand, thereby modulating, e.g., increasing or decreasing the activity of PGC-1α.

Cells, preferably, autologous cells, containing PGC-1α expressing gene sequences may then be introduced or reintroduced into the subject. Such cell replacement techniques may be preferred, for example, when the gene product is a secreted, extracellular gene product.

(ii) Methods for Inhibiting PGC-1α Expressions Synthesis, or Activity

As discussed above, inhibition of PGC-1α expression or activity may be desirable in certain situations, e.g., to create a non-human animal transgenic in which PGC-1α is misexpressed, or to modulate body weight in a subject, e.g., to treat or prevent obesity. A variety of techniques may be used to inhibit the expression, synthesis, or activity of PGC-1α genes and/or proteins.

For example, compounds such as those identified through assays described above, which exhibit inhibitory activity, may be used in accordance with the invention. Such molecules may include, but are not limited to, small organic molecules, siRNA molecules, peptides, antibodies, and the like.

For example, compounds can be administered that compete with endogenous ligand for the PGC-1α protein. The resulting reduction in the amount of ligand-bound PGC-1α protein will modulate endothelial cell physiology. Compounds that can be particularly useful for this purpose include, for example, soluble proteins or peptides, such as peptides comprising one or more of the extracellular domains, or portions and/or analogs thereof, of the PGC-1α protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the PGC-1α receptor site, but do not activate the protein, (e.g., receptor-ligand antagonists) can be effective in inhibiting PGC-1α protein activity.

Further, antisense and ribozyme molecules and siRNA molecules which inhibit expression of the PGC-1α gene may also be used in accordance with the invention to inhibit aberrant PGC-1α gene activity. Still further, triple helix molecules may be utilized in inhibiting aberrant PGC-1α gene activity.

The antisense nucleic acid molecules used in the methods of the invention are typically administered to a subject or generated in situ such that they hybridize with or bind to cellular mRNA and/or genomic DNA encoding a PGC-1α protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, an antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave PGC-1α mRNA transcripts thereby to inhibit translation of PGC-1α mRNA. A ribozyme having specificity for a PGC-1α-encoding nucleic acid can be designed based upon the nucleotide sequence of a PGC-1α cDNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in a PGC-1α-encoding mRNA (see, for example, Cech et al. U.S. Pat. No. 4,987,071; and Cech et al. U.S. Pat. No. 5,116,742). Alternatively, PGC-1α mRNA can be used to select a catalytic RNA having a specific ribonuclease activity from a pool of RNA molecules (see, for example, Bartel, D. and Szostak, J. W. (1993) *Science* 261:1411-1418).

PGC-1α gene expression can also be inhibited by targeting nucleotide sequences complementary to the regulatory region of the PGC-1α (e.g., the PGC-1α promoter and/or enhancers) to form triple helical structures that prevent transcription of the PGC-1α gene in target cells (see, for example, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15).

An RNA interfering agent, e.g., an siRNA molecule, which is targeted to PGC-1α, can also be used in order to inhibit expression of PGC-1α, e.g., through degradation or specific post-transcriptional gene silencing (PTGS) of the messenger RNA (mRNA) of PGC-1α.

Antibodies that are both specific for the PGC-1α protein and interfere with its activity may also be used to modulate or inhibit PGC-1α protein function. Such antibodies may be generated using standard techniques described herein, against the PGC-1α protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889-7893).

C. Pharmaceutical Compositions

The methods of the invention involve administering to a subject an agent which modulates PGC-1α expression or activity (e.g., an agent identified by a screening assay described herein), or a combination of such agents. In another embodiment, the method involves administering to a subject a PGC-1α protein or nucleic acid molecule as therapy to compensate for reduced, aberrant, or unwanted PGC-1α expression or activity.

Stimulation of PGC-1α activity is desirable in situations in which PGC-1α is abnormally downregulated and/or in which increased PGC-1α activity is likely to have a beneficial effect, e.g., as a therapeutic or prophylactic.

The agents which modulate PGC-1α activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates PGC-1α activity (e.g., a fragment of a PGC-1α protein or an anti-PGC-1α antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate PGC-1α activity can also be prepared in the form of suppositories (e.g., with conventional suppository bases such as cocoa butter and other glycerides) or retention enemas for rectal delivery.

In one embodiment, the agents that modulate PGC-1α activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates PGC-1α activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such PGC-1α modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a PGC-1α molecule, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated, e.g., the intended use of the agonist or antagonize.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PGC-1α protein and/or nucleic acid expression as well as PGC-1α activity, in the context of a biological sample (e.g., blood, serum, fluid, e.g., cerebrospinal fluid, spinal fluid, cells, or tissue, e.g., neural tissue) to thereby determine whether an individual is afflicted with neurological disease or disorder neurological disease or disorder has a risk of developing a neurological disease or disorder. The invention also provides for prognostic (or predictive) assays for determining whether an individual is at risk of developing a neurological disease or disorder. For example, mutations in a PGC-1α gene can be assayed for in a biological sample. Such assays can be used for prognostic or predictive purpose to thereby phophylactically treat an individual prior to the onset of a neurological disease or disorder.

One particular embodiment includes a method for assessing whether a subject is afflicted with a neurological disease or disorder has a risk of developing a neurological disease or disorder comprising detecting the expression of the PGC-1α gene or the activity of PGC-1α in a cell or tissue sample of a subject, wherein a decrease in the expression of the PGC-1α gene or a decrease in the activity of PGC-1α indicates the presence of a neurological disease or disorder or the risk of developing a neurological disease or disorder in the subject. In this embodiment, subject samples tested are, for example, cerebrospinal fluid, spinal fluid, and neural tissue.

Another aspect of the invention pertains to monitoring the influence of PGC-1α modulators on the expression or activity of PGC-1α in clinical trials.

These and other agents are described in further detail in the following sections.

A. Prognostic and Diagnostic Assays

To determine whether a subject is afflicted with a neurological disease or disorder has a risk of developing a neurological disease or disorder, a biological sample may be obtained from a subject and the biological sample may be contacted with a compound or an agent capable of detecting a PGC-1α protein or nucleic acid (e.g., mRNA or genomic DNA) that encodes a PGC-1α protein, in the biological sample. A preferred agent for detecting PGC-1α mRNA or genomic DNA is a labeled nucleic acid probe capable of hybridizing to PGC-1α mRNA or genomic DNA. The nucleic acid probe can be, for example, the PGC-1α nucleic acid set forth in SEQ ID NO:1, or a portion thereof, such as an oligonucleotide of at least 15, 20, 25, 30, 25, 40, 45, 50, 100, 250 or 500 nucleotides in length and sufficient to specifically hybridize under stringent conditions to PGC-1α mRNA or genomic DNA. Other suitable probes for use in the diagnostic assays of the invention are described herein.

The term "biological sample" is intended to include tissues, cells, and biological fluids isolated from a subject, as well as tissues, cells, and fluids present within a subject, e.g., cerebrospinal fluid, spinal fluid, and neural tissue. That is, the detection method of the invention can be used to detect PGC-1α mRNA, protein, or genomic DNA in a biological sample in vitro as well as in vivo. For example, in vitro techniques for detection of PGC-1α mRNA include Northern hybridizations and in situ hybridizations. In vitro techniques for detection of PGC-1α protein include enzyme linked immunosorbent assays (ELISAs), Western blots, immunoprecipitations and immunofluorescence. In vitro techniques for detection of PGC-1α genomic DNA include Southern hybridizations. Furthermore, in vivo techniques for detection of PGC-1α protein include introducing into a subject a labeled anti-PGC-1α antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting PGC-1α protein, mRNA, or genomic DNA, such that the presence of PGC-1α protein, mRNA or genomic DNA is detected in the biological sample, and comparing the presence of PGC-1α protein, mRNA or genomic DNA in the control sample with the presence of PGC-1α protein, mRNA or genomic DNA in the test sample.

Analysis of one or more PGC-1α polymorphic regions in a subject can be useful for predicting whether a subject has or is likely to develop a neurological disease or disorder. In preferred embodiments, the methods of the invention can be characterized as comprising detecting, in a sample of cells from the subject, the presence or absence of a specific allelic variant of one or more polymorphic regions of a PGC-1α gene. The allelic differences can be: (i) a difference in the identity of at least one nucleotide or (ii) a difference in the number of nucleotides, which difference can be a single nucleotide or several nucleotides. The invention also provides methods for detecting differences in an PGC-1α gene such as chromosomal rearrangements, e.g., chromosomal dislocation. The invention can also be used in prenatal diagnostics.

A preferred detection method is allele specific hybridization using probes overlapping the polymorphic site and having about 5, 10, 20, 25, or 30 nucleotides around the polymorphic region. In a preferred embodiment of the invention, several probes capable of hybridizing specifically to allelic variants are attached to a solid phase support, e.g., a "chip". Oligonucleotides can be bound to a solid support by a variety of processes, including lithography. For example, a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism in the 5' upstream regulatory element can be determined in a single hybridization experiment.

In other detection methods, it is necessary to first amplify at least a portion of a PGC-1α gene prior to identifying the allelic variant. Amplification can be performed, e.g., by PCR and/or LCR (see Wu and Wallace, (1989) *Genomics* 4:560), according to methods known in the art. In one embodiment, genomic DNA of a cell is exposed to two PCR primers and amplification for a number of cycles sufficient to produce the required amount of amplified DNA. In preferred embodiments, the primers are located between 150 and 350 base pairs apart.

Alternative amplification methods include: self sustained sequence replication (Guatelli, J. C. et al., 1990, *Proc. Natl. Acad. Sci. USA* 87:1874-1878), transcriptional amplification system (Kwoh, D. Y. et al., 1989, *Proc. Natl. Acad. Sci. USA* 86:1173-1177), Q-Beta Replicase (Lizardi, P. M. et al., 1988, *Bio/Technology* 6:1197), and self-sustained sequence replication (Guatelli et al., (1989) *Proc. Nat. Acad. Sci.* 87:1874), and nucleic acid based sequence amplification (NABSA), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of a PGC-1α gene and detect allelic variants, e.g., mutations, by comparing the sequence of the sample sequence with the corresponding reference (control) sequence. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of a specific allele of a PGC-1α gene in DNA from a subject can be shown by restriction enzyme analysis. For example, a specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of an PGC-1α allelic variant with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al. (1988) *Proc. Natl Acad Sci USA* 85:4397; Saleeba et al (1992) *Methods Enzymol.* 217:286-295. In a preferred embodiment, the control or sample nucleic acid is labeled for detection.

In another embodiment, an allelic variant can be identified by denaturing high-performance liquid chromatography (DHPLC) (Oefner and Underhill, (1995) *Am. J. Human Gen.* 57:Suppl. A266). DHPLC uses reverse-phase ion-pairing chromatography to detect the heteroduplexes that are generated during amplification of PCR fragments from individuals who are heterozygous at a particular nucleotide locus within that fragment (Oefner and Underhill (1995) *Am. J. Human Gen.* 57:Suppl. A266). In general, PCR products are produced using PCR primers flanking the DNA of interest. DHPLC analysis is carried out and the resulting chromatograms are analyzed to identify base pair alterations or deletions based on specific chromatographic profiles (see O'Donovan et al. (1998) *Genomics* 52:44-49).

In other embodiments, alterations in electrophoretic mobility is used to identify the type of PGC-1α allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat Res* 285:125-144; and Hayashi (1992) *Genet*

*Anal Tech Appl* 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265: 1275).

Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163); Saiki et al (1989) *Proc. Natl Acad. Sci USA* 86:6230; and Wallace et al. (1979) *Nucl. Acids Res.* 6:3543). Such allele specific oligonucleotide hybridization techniques may be used for the simultaneous detection of several nucleotide changes in different polymorphic regions of PGC-1α. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238; Newton et al. (1989) *Nucl. Acids Res.* 17:2503). This technique is also termed "PROBE" for Probe Oligo Base Extension. In addition, it may be desirable to introduce a novel restriction site in the region of the mutation to create cleavage-based detection (Gasparini et al. (1992) *Mol. Cell Probes* 6:1).

In another embodiment, identification of the allelic variant is carried out using an oligonucleotide ligation assay (OLA), as described, e.g., in U.S. Pat. No. 4,998,617 and in Landegren, U. et al., (1988) *Science* 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., (1990) *Proc. Natl. Acad. Sci.* (*U.S.A.*) 87:8923-8927. In this method, PCR is used to achieve the exponential amplification of target DNA, which is then detected using OLA.

Several techniques based on this OLA method have been developed and can be used to detect specific allelic variants of a polymorphic region of an PGC-1α gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) *Nucleic Acids Res* 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in a PGC-1α gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each subject. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide presents in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site (Cohen, D. et al. (French Patent 2,650, 840; PCT Application No. WO91/02087). As in the Mundy method of U.S. Pat. No. 4,656,127, a primer is employed that is complementary to allelic, sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Application No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

For determining the identity of the allelic variant of a polymorphic region located in the coding region of a PGC-1α gene, yet other methods than those described above can be used. For example, identification of an allelic variant which encodes a mutated PGC-1α protein can be performed by using an antibody specifically recognizing the mutant protein in, e.g., immunohistochemistry or immunoprecipitation. Antibodies to wild-type PGC-1α or mutated forms of PGC-1α proteins can be prepared according to methods known in the art.

Alternatively, one can also measure an activity of a PGC-1α protein, such as binding to a PGC-1α ligand. Binding assays are known in the art and involve, e.g., obtaining cells from a subject, and performing binding experiments with a labeled lipid, to determine whether binding to the mutated form of the protein differs from binding to the wild-type of the protein.

Antibodies directed against reference or mutant PGC-1α polypeptides or allelic variant thereof, which are discussed above, may also be used in disease diagnostics and prognostics. Such diagnostic methods, may be used to detect abnormalities in the level of PGC-1α polypeptide expression, or abnormalities in the structure and/or tissue, cellular, or subcellular location of an PGC-1α polypeptide. Structural differences may include, for example, differences in the size, electronegativity, or antigenicity of the mutant PGC-1α polypeptide relative to the normal PGC-1α polypeptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al, 1989, supra, at Chapter 18. The protein detection and isolation methods employed herein may also be such as those described in Harlow and Lane, for example (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of PGC-1α polypeptides. In situ detection may be accomplished by removing a histological specimen from a subject, and applying thereto a labeled antibody of the present invention. The antibody (or fragment) is preferably applied by overlaying the labeled antibody (or fragment) onto a biological sample. Through the use of such a procedure, it is possible to determine not only the presence of the PGC-1α polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-PGC-1α polypeptide specific antibody is via linkage to an enzyme and use in an enzyme immunoassay (EIA) (Voller, "The Enzyme Linked Immunosorbent Assay (ELISA)", Diagnostic Horizons 2:1-7, 1978, Microbiological Associates Quarterly Publication, Walkersville, Md.; Voller, et al., J. Clin. Pathol. 31:507-520 (1978); Butler, Meth. Enzymol. 73:482-523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

If a polymorphic region is located in an exon, either in a coding or non-coding portion of the gene, the identity of the allelic variant can be determined by determining the molecular structure of the mRNA, pre-mRNA, or cDNA. The molecular structure can be determined using any of the above described methods for determining the molecular structure of the genomic DNA.

The methods described herein may be performed, for example, by utilizing pre-packaged diagnostic kits, such as those described above, comprising at least one probe or primer nucleic acid described herein, which may be conveniently used, e.g., to determine whether a subject has or is at risk of developing a disease associated with a specific PGC-1α allelic variant.

Sample nucleic acid to be analyzed by any of the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of subject tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

B. Monitoring of Effects During Clinical Trials

The present invention further provides methods for determining the effectiveness of a PGC-1α modulator (e.g., a PGC-1α modulator identified herein) in treating or preventing a neurological disease or disorder or assessing risk of developing a neurological disease or disorder in a subject. For example, the effectiveness of a PGC-1α modulator in increasing or decreasing PGC-1α gene expression, protein levels, or in upregulating or down-regulating PGC-1α activity, can be monitored in clinical trials of subjects exhibiting increased or decreased PGC-1α gene expression, protein levels, or upregulated or downregulated PGC-1α activity. In such clinical trials, the expression or activity of a PGC-1α gene, and preferably, other genes that have been implicated in, for example, a PGC-1α pathway can be used as a "read out" or marker of the phenotype of a particular cell.

For example, and not by way of limitation, genes, including PGC-1α, that are modulated in cells by treatment with an agent which modulates PGC-1α activity (e.g., identified in a screening assay as described herein) can be identified. Thus, to study the effect of agents which modulate PGC-1α activity on subjects suffering a neurological disease or disorder, or agents to be used as a prophylactic, for example, a clinical trial, cells can be isolated and RNA prepared and analyzed for the levels of expression of PGC-1α and other genes implicated in PGC-1α activity or expression. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of PGC-1α or other genes. In this way, the gene expression pattern can serve as a marker, indicative of the physiological response of the cells to the agent which modulates PGC-1α activity. This response state may be determined before, and at various points during treatment of the individual with the agent which modulates PGC-1α activity.

In a preferred embodiment, the present invention provides a method for monitoring the effectiveness of treatment of a subject with an agent which modulates PGC-1α activity (e.g., an agonist, antagonist, peptidomimetic, protein, peptide, nucleic acid, siRNA, or small molecule identified by the screening assays described herein) including the steps of (i) obtaining a pre-administration sample from a subject prior to administration of the agent; (ii) detecting the level of expression of a PGC-1α protein, mRNA, or genomic DNA in the pre-administration sample; (iii) obtaining one or more post-administration samples from the subject; (iv) detecting the level of expression or activity of the PGC-1α protein, mRNA, or genomic DNA in the post-administration samples; (v) comparing the level of expression or activity of the PGC-1α protein, mRNA, or genomic DNA in the pre-administration sample with the PGC-1α protein, mRNA, or genomic DNA in the post administration sample or samples; and (vi) altering the administration of the agent to the subject accordingly. For example, increased administration of the agent may be desirable to increase the expression or activity of PGC-1α to higher levels than detected, i.e., to increase the effectiveness of the agent. According to such an embodiment, PGC-1α expression or activity may be used as an indicator of the effectiveness of an agent, even in the absence of an observable phenotypic response.

IV. Recombinant Expression Vectors and Host Cells used in the Methods of the Invention The methods of the invention (e.g., the screening assays and therapeutic and/or preventative methods described herein) include the use of vectors, preferably expression vectors, containing a nucleic acid encoding a PGC-1α protein (or a portion thereof). For example, in one embodiment, a vector containing a nucleic acid encoding a PGC-1α protein, or portion thereof, is used to deliver a PGC-1α protein, or portion thereof, to a subject, to treat or prevent a neurological disease or disorder in the subject. In one embodiment, the vector containing a nucleic acid encoding a PGC-1α protein, or portion thereof, is targeted to a specific cell type, organ or tissue, e.g., a brain cell or a specific portion of the brain, e.g., the striatum, using, e.g., a tissue specific promoter as described herein.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PGC-1α proteins, mutant forms of PGC-1α proteins, fusion proteins, and the like).

The recombinant expression vectors to be used in the methods of the invention can be designed for expression of PGC-1α proteins in prokaryotic or eukaryotic cells. For example, PGC-1α proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PGC-1α activity assays, (e.g., direct assays or competitive assays described in detail below), or to generate antibodies specific for PGC-1α proteins. In a preferred embodiment, a PGC-1α fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual. 2nd ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include neuron-specific promoters (e.g., the neurofilament promoter; Byrne and Ruddle, 1989, *Proc. Natl. Acad. Sci. USA* 86:5473-5477), albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PGC-1α mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a PGC-1α nucleic acid molecule of the invention is introduced, e.g., a PGC-1α nucleic acid molecule within a recombinant expression vector or a PGC-1α nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PGC-1α protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a PGC-1α protein. Accordingly, the invention further provides methods for producing a PGC-1α protein using the host cells of the invention. In one embodiment, the method comprises culturing the host cell of the invention (into which a recombinant expression vector encoding a PGC-1α protein has been introduced) in a suitable medium such that a PGC-1α protein is produced. In another embodiment, the method further comprises isolating a PGC-1α protein from the medium or the host cell.

The host cells of the invention can also be used to produce nonhuman transgenic animals. For example, in one embodiment, a host cell of the invention is a fertilized oocyte or an embryonic stem cell into which sequences encoding a polypeptide corresponding to a marker of the invention have been introduced. Such host cells can then be used to create non-human transgenic animals in which exogenous sequences encoding a marker protein of the invention have been introduced into their genome or homologous recombinant animals in which endogenous gene(s) encoding a polypeptide corresponding to a marker of the invention sequences have been altered. Such animals are useful for studying the function and/or activity of PGC-1α, for identifying and/or evaluating modulators of PGC-1α polypeptide activity, as well as in pre-clinical testing of therapeutics or diagnostic molecules, for marker discovery or evaluation, e.g., therapeutic and diagnostic marker discovery or evaluation, or as surrogates of drug efficacy and specificity.

A transgenic animal of the invention can be created by introducing a nucleic acid encoding a polypeptide corresponding to PGC-1α into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide corresponding to a marker of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilnut et al. (1997) *Nature* 385:810-813 and PCT Publication NOS. WO 97/07668 and WO 97/07669.

V. Isolated Nucleic Acid Molecules used in the Methods of the Invention

The nucleotide sequence of the isolated human PGC-1α cDNA and the predicted amino acid sequence of the human PGC-1α polypeptide are shown in SEQ ID NOs:1 and 2, respectively. The nucleotide and amino acid sequences of human PGC-1α are also described in GenBank Accession No. GI:29570796. The nucleotide sequence of the isolated human PGC-1α cDNA and the predicted amino acid sequence of the human PGC-1α polypeptide are shown in SEQ ID NOs:45 and 46, respectively. The nucleotide and amino acid sequences of mouse PGC-1α are also described in GenBank Accession No. GI:6679432.

The methods of the invention include the use of isolated nucleic acid molecules that encode PGC-1α proteins or biologically active portions thereof, as well as nucleic acid fragments sufficient for use as hybridization probes to identify PGC-1α-encoding nucleic acid molecules (e.g., PGC-1α mRNA) and fragments for use as PCR primers for the amplification or mutation of PGC-1α nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:1, or a portion thereof, can be isolated using standard molecular biology techniques and the sequence information provided herein. Using all or portion of the nucleic acid sequence of SEQ ID NO:1 as a hybridization probe, PGC-1α nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to PGC-1α nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:1, a complement of the nucleotide sequence shown in SEQ ID NO:1, or a portion of any of these nucleotide sequences. A nucleic acid molecule which is complementary to the nucleotide sequence shown in SEQ ID NO:1, is one which is sufficiently complementary to the nucleotide sequence shown in SEQ ID NO:1 such that it can hybridize to the nucleotide sequence shown in SEQ ID NO:1 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:1 or a portion of any of this nucleotide sequence.

Moreover, the nucleic acid molecules used in the methods of the invention can comprise only a portion of the nucleic acid sequence of SEQ ID NO:1, for example, a fragment which can be used as a probe or primer or a fragment encoding a portion of a PGC-1α protein, e.g., a biologically active portion of a PGC-1α protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 of an anti-sense sequence of SEQ ID NO:1 or of a naturally occurring allelic variant or mutant of SEQ ID NO:1. In one embodiment, a nucleic acid molecule used in the methods of the present invention comprises a nucleotide sequence which is greater than 100, 100-200, 200-300, 300-400, 400-500, 500-600, 600-700, 700-800, 800-900, 900-1000, 1000-1100, 1100-1200, 1200-1300, or more nucleotides in length and hybridizes under stringent hybridization conditions to a nucleic acid molecule of SEQ ID NO:1.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(°C.)=2(\# \text{ of } A+T \text{ bases})+4(\# \text{ of } G+C \text{ bases})$. For hybrids between 18 and 49 base pairs in length, $T_m(°C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express a PGC-1α protein, such as by measuring a level of a PGC-1α-encoding nucleic acid in a sample of cells from a subject e.g., detecting PGC-1α mRNA levels or determining whether a genomic PGC-1α gene has been mutated or deleted.

The methods of the invention further encompass the use of nucleic acid molecules that differ from the nucleotide sequence shown in SEQ ID NO:1 due to degeneracy of the genetic code and thus encode the same PGC-1α proteins as those encoded by the nucleotide sequence shown in SEQ ID NO:1. In another embodiment, an isolated nucleic acid molecule included in the methods of the invention has a nucleotide sequence encoding a protein having an amino acid sequence shown in SEQ ID NO:2.

The methods of the invention further include the use of allelic variants of human PGC-1α, e.g., functional and non-functional allelic variants. Functional allelic variants are naturally occurring amino acid sequence variants of the human PGC-1α protein that maintain a PGC-1α activity. Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the human PGC-1α protein that do not have a PGC-1α activity. Non-functional allelic variants will typically contain a non-conservative substitution, deletion, or insertion or premature truncation of the amino acid sequence of SEQ ID NO:2, or a substitution, insertion or deletion in critical residues or critical regions of the protein.

The methods of the present invention may further use non-human orthologues of the human PGC-1α protein. Orthologues of the human PGC-1α protein are proteins that are isolated from non-human organisms and possess the same PGC-1α activity.

The methods of the present invention further include the use of nucleic acid molecules comprising the nucleotide sequence of SEQ ID NO:1 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of PGC-1α (e.g., the sequence of SEQ ID NO:2) without altering the biological activity, whereas an "essential" amino acid residue is required for biological activity. For example, amino acid residues that are conserved among the PGC-1α proteins of the present invention and other members of the PGC-1 family are not likely to be amenable to alteration.

Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PGC-1α protein is preferably replaced with another amino acid residue from the same side chain family. Alternatively, in another embodiment, mutations can be introduced randomly along all or part of a PGC-1α coding sequence, such as by saturation mutagenesis, and the resultant mutants can be screened for PGC-1α biological activity to identify mutants that retain activity. Following mutagenesis of SEQ ID NO:1 the encoded protein can be expressed recombinantly and the activity of the protein can be determined using the assay described herein.

Another aspect of the invention pertains to the use of isolated nucleic acid molecules which are antisense to the nucleotide sequence of SEQ ID NO: 1. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PGC-1α coding strand, or to only a portion thereof. In one embodiment, an antisense nucleic acid molecule is antisense to a "coding region" of the coding strand of a nucleotide sequence encoding a PGC-1α. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PGC-1α. The term "noncoding region" refers to 5' and 3' sequences which flank the coding region that are not translated into amino acids (also referred to as 5' and 3' untranslated regions).

Given the coding strand sequences encoding PGC-1α disclosed herein, antisense nucleic acids of the invention can be designed according to the rules of Watson and Crick base pairing. The antisense nucleic acid molecule can be complementary to the entire coding region of PGC-1α mRNA, but more preferably is an oligonucleotide which is antisense to only a portion of the coding or noncoding region of PGC-1α mRNA. For example, the antisense oligonucleotide can be complementary to the region surrounding the translation start site of PGC-1α mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acid molecules used in the methods of the invention are further described above, in section IV.

In yet another embodiment, the PGC-1α nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670-675.

PNAs of PGC-1α nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of PGC-1α nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of PGC-1α can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PGC-1α nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)

amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

VI. Isolated PGC-1α Proteins and Anti-PGC-1α Antibodies used in the Methods of the Invention The methods of the invention include the use of isolated PGC-1α proteins, and biologically active portions thereof, as well as polypeptide fragments suitable for use as immunogens to raise anti-PGC-1α antibodies. In one embodiment, native PGC-1α proteins can be isolated from cells or tissue sources by an appropriate purification scheme using standard protein purification techniques. In another embodiment, PGC-1α proteins are produced by recombinant DNA techniques. Alternative to recombinant expression, a PGC-1α protein or polypeptide can be synthesized chemically using standard peptide synthesis techniques.

As used herein, a "biologically active portion" of a PGC-1α protein includes a fragment of a PGC-1α protein having a PGC-1α activity. Biologically active portions of a PGC-1α protein include peptides comprising amino acid sequences sufficiently identical to or derived from the amino acid sequence of the PGC-1α protein, e.g., the amino acid sequence shown in SEQ ID NO:2, which include fewer amino acids than the full length PGC-1α proteins, and exhibit at least one activity of a PGC-1α protein. Typically, biologically active portions comprise a domain or motif with at least one activity of the PGC-1α protein (e.g., the N-terminal region of the PGC-1α protein that is believed to be involved in the regulation of apoptotic activity). A biologically active portion of a PGC-1α protein can be a polypeptide which is, for example, 25, 50, 75, 100, 125, 150, 175, 200, 250, 300 or more amino acids in length. Biologically active portions of a PGC-1α protein can be used as targets for developing agents which modulate a PGC-1α activity.

In a preferred embodiment, the PGC-1α protein used in the methods of the invention has an amino acid sequence shown in SEQ ID NO:2. In other embodiments, the PGC-1α protein is substantially identical to SEQ ID NO:2, and retains the functional activity of the protein of SEQ ID NO:2, yet differs in amino acid sequence due to natural allelic variation or mutagenesis, as described in detail in subsection V above. Accordingly, in another embodiment, the PGC-1α protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the PGC-1α amino acid sequence of SEQ ID NO:2 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg-.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11-17 (1988)) which has been incorporated into the ALIGN program (version 2.0 or 2.0U), using a PAM120 weight residue table, a gap length penalty of 12 and a gap penalty of 4.

The methods of the invention may also use PGC-1α chimeric or fusion proteins. As used herein, a PGC-1α "chimeric protein" or "fusion protein" comprises a PGC-1α polypeptide operatively linked to a non-PGC-1α polypeptide. An "PGC-1α polypeptide" refers to a polypeptide having an amino acid sequence corresponding to a PGC-1α molecule, whereas a "non-PGC-1α polypeptide" refers to a polypeptide having an amino acid sequence corresponding to a protein which is not substantially homologous to the PGC-1α protein, e.g., a protein which is different from the PGC-1α protein and which is derived from the same or a different organism. Within a PGC-1α fusion protein the PGC-1α polypeptide can correspond to all or a portion of a PGC-1α protein. In a preferred embodiment, a PGC-1α fusion protein comprises at least one biologically active portion of a PGC-1α protein. In another preferred embodiment, a PGC-1α:

fusion protein comprises at least two biologically active portions of a PGC-1α protein. Within the fusion protein, the term "operatively linked" is intended to indicate that the PGC-1α (polypeptide and the non-PGC-1α polypeptide are fused in-frame to each other. The non-PGC-1α polypeptide can be fused to the N-terminus or C-terminus of the PGC-1α polypeptide.

For example, in one embodiment, the fusion protein is a GST-PGC-1α fusion protein in which the PGC-1α sequences are fused to the C-terminus of the GST sequences. Such fusion proteins can facilitate the purification of recombinant PGC-1α.

In another embodiment, this fusion protein is a PGC-1α protein containing a heterologous signal sequence at its N-terminus. In certain host cells (e.g., mammalian host cells), expression and/or secretion of PGC-1α can be increased through use of a heterologous signal sequence.

The PGC-1α fusion proteins used in the methods of the invention can be incorporated into pharmaceutical compositions and administered to a subject in vivo. The PGC-1α fusion proteins can be used to affect the bioavailability of a PGC-1α substrate. Use of PGC-1α fusion proteins may be useful therapeutically for the treatment of disorders caused by, for example, (i) aberrant modification or mutation of a gene encoding a PGC-1α protein; (ii) mis-regulation of the PGC-1α gene; and (iii) aberrant post-translational modification of a PGC-1α protein.

Moreover, the PGC-1α-fusion proteins used in the methods of the invention can be used as immunogens to produce anti-PGC-1α antibodies in a subject, to purify PGC-1α ligands and in screening assays to identify molecules which inhibit the interaction of PGC-1α with a PGC-1α substrate.

Preferably, a PGC-1α chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PGC-1α-encoding nucleic acid can be cloned into such an expression vector such that the fusion moiety is linked in-frame to the PGC-1α protein.

The present invention also pertains to the use of variants of the PGC-1α proteins which function as either PGC-1α agonists (mimetics) or as PGC-1α antagonists. Variants of the PGC-1α proteins can be generated by mutagenesis, e.g., discrete point mutation or truncation of a PGC-1α protein. An agonist of the PGC-1α proteins can retain substantially the same, or a subset, of the biological activities of the naturally occurring form of a PGC-1α protein. An antagonist of a PGC-1α protein can inhibit one or more of the activities of the naturally occurring form of the PGC-1α protein by, for example, competitively modulating a PGC-1α-mediated activity of a PGC-1α protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PGC-1α protein.

In one embodiment, variants of a PGC-1α protein which function as either PGC-1α agonists (mimetics) or as PGC-1α antagonists can be identified by screening combinatorial libraries of mutants, e.g., truncation mutants, of a PGC-1α protein for PGC-1α protein agonist or antagonist activity. In one embodiment, a variegated library of PGC-1α variants is generated by combinatorial mutagenesis at the nucleic acid level and is encoded by a variegated gene library. A variegated library of PGC-1α variants can be produced by, for example, enzymatically ligating a mixture of synthetic oligonucleotides into gene sequences such that a degenerate set of potential PGC-1α sequences is expressible as individual polypeptides, or alternatively, as a set of larger fusion proteins (e.g., for phage display) containing the set of PGC-1α sequences therein. There are a variety of methods which can be used to produce libraries of potential PGC-1α variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PGC-1α sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a PGC-1α protein coding sequence can be used to generate a variegated population of PGC-1α fragments for screening and subsequent selection of variants of a PGC-1α protein. In one embodiment, a library of coding sequence fragments can be generated by treating a double stranded PCR fragment of a PGC-1α coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PGC-1α protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PGC-1α proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PGC-1α variants (Arkin and Yourvan (1992) *Proc. Natl. Acad. Sci. USA* 89:7811-7815; Delgrave et al. (1993) *Protein Engineering* 6(3):327-331).

The methods of the present invention further include the use of anti-PGC-1α antibodies. An isolated PGC-1α protein, or a portion or fragment thereof, can be used as an immunogen to generate antibodies that bind PGC-1α using standard techniques for polyclonal and monoclonal antibody preparation. A full-length PGC-1α protein can be used or, alternatively, antigenic peptide fragments of PGC-1α can be used as immunogens. The antigenic peptide of PGC-1α comprises at least 8 amino acid residues of the amino acid sequence shown in SEQ ID NO:2 and encompasses an epitope of PGC-1α such that an antibody raised against the peptide forms a specific immune complex with the PGC-1α protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PGC-1α that are located on the surface of the protein, e.g., hydrophilic regions, as well as regions with high antigenicity.

A PGC-1α immunogen is typically used to prepare antibodies by immunizing a suitable subject, (e.g., rabbit, goat, mouse, or other mammal) with the immunogen. An appropriate immunogenic preparation can contain, for example, recombinantly expressed PGC-1α protein or a chemically synthesized PGC-1α polypeptide. The preparation can further include an adjuvant, such as Freund's complete or incomplete adjuvant, or similar immunostimulatory agent. Immunization of a suitable subject with an immunogenic PGC-1α preparation induces a polyclonal anti-PGC-1α antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a PGC-1α. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PGC-1α molecules. The term "monoclonal antibody" or "monoclonal antibody composition", as used herein, refers to a population of antibody molecules that contain only one species of an antigen binding site capable of immunoreacting with a particular epitope of PGC-1α. A monoclonal antibody composition thus typically displays a single binding affinity for a particular PGC-1α protein with which it immunoreacts.

Polyclonal anti-PGC-1α antibodies can be prepared as described above by immunizing a suitable subject with a PGC-1α immunogen. The anti-PGC-1α antibody titer in the immunized subject can be monitored over time by standard techniques, such as with an enzyme linked immunosorbent assay (ELISA) using immobilized PGC-1α. If desired, the antibody molecules directed against PGC-1α can be isolated from the mammal (e.g., from the blood) and further purified by well known techniques, such as protein A chromatography to obtain the IgG fraction. At an appropriate time after immunization, e.g., when the anti-PGC-1α antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J Cancer* 29:269-75), the more recent human B cell hybridoma technique (Kozbor et al. (1983) *Immunol Today* 4:72), the EBV-hybridoma technique (Cole et al (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with a PGC-1α immunogen as described above, and the culture supernatants of the resulting hybridoma cells are screened to identify a hybridoma producing a monoclonal antibody that binds PGC-1α.

Any of the many well known protocols used for fusing lymphocytes and immortalized cell lines can be applied for the purpose of generating an anti-PGC-1α monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag-4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1α, e.g., using a standard ELISA assay.

Alternative to preparing monoclonal antibody-secreting hybridomas, a monoclonal anti-PGC-1α antibody can be identified and isolated by screening a recombinant combinatorial immunoglobulin library (e.g., an antibody phage display library) with PGC-1α to thereby isolate immunoglobulin library members that bind PGC-1α. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PGC-1α antibodies, such as chimerzic and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; Shaw et al. (1988) *J. Natl. Cancer Inst.* 80:1553-1559; Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PGC-1α antibody can be used to detect PGC-1α protein (e.g., in a cellular lysate or cell supernatant) in order to evaluate the abundance and pattern of expression of the PGC-1α protein. Anti-PGC-1α antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

This invention is further illustrated by the following Exemplification which should not be construed as limiting. The contents of all references, sequences, Figures, GenBank Accession Numbers, and published patent applications cited throughout this application are hereby incorporated by reference.

EXAMPLES

Materials and Methods

The following materials and methods were used for the experiments described below.

Generation of PGC-1α$^{-/-}$ Mice

Figure 9:
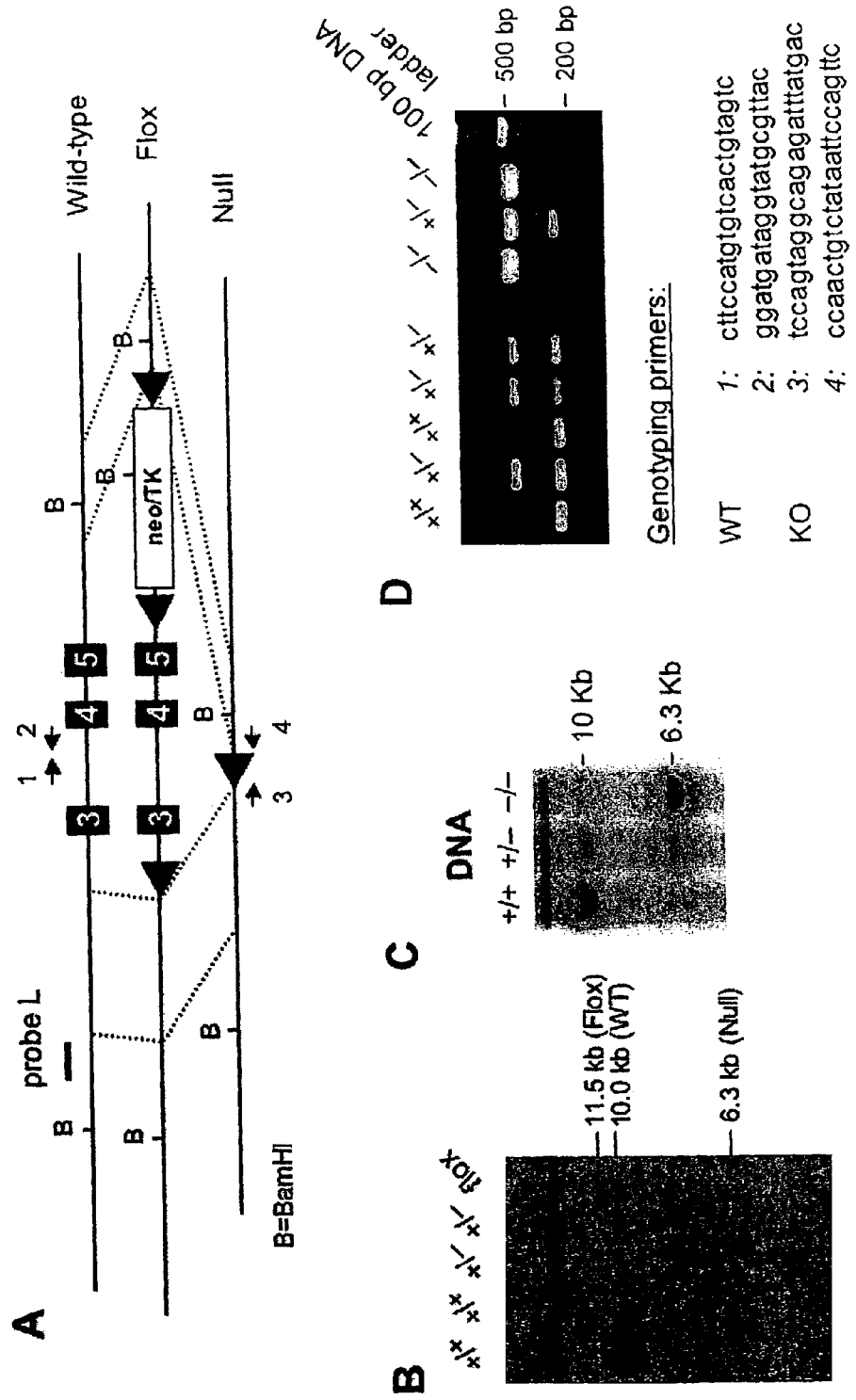
FIGS. 9A-D depict genotyping of mice of the present invention by PCR with tail DNA. In particular.

A targeting plasmid was constructed using genomic DNA fragments derived from Sv129 mouse strain. A loxP site and a neomycin/thymidine kinase cassette flanked by two loxP sites were introduced into the PGC-1α locus. Embryonic stem (ES) cell (derived from Sv129 strain) electroporation, selection and screening were performed using standard gene targeting techniques. Genomic DNA was isolated from neomycin-resistant ES cell clones, digested with BamHI and subjected to hybridization using probe L to detect homologous recombination and the presence of the flox allele (FIG. 9A). Chimeric founders were bred with wild-type C57/B16 mice to obtain offspring containing a germ-line PGC-1α flox allele. These mice were subsequently bred with ZP3-cre transgenic (in C57/B16 background) mice to generate PGC-1α$^{+/-}$ offspring. The cre recombinase-mediated generation of PGC-1α$^{+/-}$ allele was confirmed by Southern hybridization using probe L following restriction digestion by BamHI. Heterozygous mice were mated to obtain PGC-1α$^{-/-}$ mice. Genotyping of mice used in this study was performed by PCR with tail DNA as shown in FIG. 9.

Animal Experiments

Mice were maintained on a standard rodent chow or a high-fat diet containing 57% fat-derived calories (D12331, Research Diets™) with twelve-hour light and dark cycles. Plasma glucose and insulin concentrations were measured from tail blood using glucometer (Lifescan, Johnson & Johnson™) and an insulin ELISA kit (Crystal Chem. Inc.™), respectively.

For diet-induced obesity, body weight was measured weekly for a period of 4 months. Body fat content was measured using a dual X-ray absorptiometry (Piximus, Lunar Corporation™) after three months on the high-fat diet.

For cold exposure, 6 to 7-week old male mice were individually housed in cages kept at 4° C. with free access to food and water. Core body temperature was monitored using a rectal thermometer at various times after the start of cold exposure. Brown fat was dissected 5 hours after cold exposure and subjected to gene expression analysis.

Metabolic monitoring was performed using a Comprehensive Lab Animal Monitoring System (CLAMS, Columbia Instruments) that simultaneously measures whole body oxygen consumption and physical movements for sixteen mice. Mice were acclimated in the monitoring chambers for two days before the experiment to minimize the changes in housing environments. Data was collected every 48 minutes for each mouse over a period of three days. Metabolic rate and physical activity were averaged for the whole study period with the exception of the first five data points that tend to be influenced by animal handling at the beginning of studies.

Histological Analysis

Tissues were dissected and fixed in 4% paraformaldehyde overnight and rinsed with phosphate-buffered saline. Brown fat was subsequently dehydrated and embedded in plastic (JB-4, Electron Microscopy Sciences™) and sectioned at 1.5 μm for Hematoxylin and Eosin (H&E) staining. Liver tissue was dehydrated in ethanol, paraffin-embedded, and sectioned at 4 μm for H&E staining.

Brain tissue for neuropathological examination was prepared from 6 and 12-week old wild-type and PGC-1α null mice. Tissues were fixed in situ by intracardiac perfusion with 15 ml PBS followed by 30 ml 4% paraformaldehyde (PFA) in phosphate buffer solution (PBS). Brains were removed, post-fixed in 4% PFA overnight at 4° C. and embedded in paraffin. Coronal sections (6 μm) were stained both conventionally with H&E, luxol fast blue (H&E+LFB), and 0.1% cresyl echt violet (Nissl), and immunohistochemically with antibodies against glial fibrillary acidic protein (GFAP, polyclonal antibody 1:200; Dako™, Hamburg, Germany) as an astrocyte marker and against neurofilament 200 kD (monoclonal antibody 1:50; Sigma™) to label axons.

RNA and Protein Analysis

Total RNA was isolated from cultured hepatocytes or tissues using Trizol reagents (Invitrogen™). For hybridization, 10-20 μg of RNA samples were separated on a formaldehyde gel, transferred to nylon membrane and then hybridized with gene-specific probes. For real-time PCR analysis, RNA samples were reverse-transcribed and used in quantitative PCR reactions in the presence of a fluorescent dye (Cybergreen™, Bio-rad™). Relative abundance of mRNA was calculated after normalization to 18S ribosomal RNA. Sequences for the primers used in this study were shown in Table 1.

TABLE 1

List of primers used in real-time PCR analysis.

| Gene | Forward primer | SEQ ID NO. | Reverse primer | SEQ ID NO. |
|---|---|---|---|---|
| PGC-1α | agccgtgaccactgacaacgag | 3 | gctgcatggttctgagtgctaag | 22 |
| PGC-1β | cgctccaggagactgaatccag | 4 | cttgactactgtctgtgaggc | 23 |
| PEPCK | catatgctgatcctgggcataac | 5 | caaacttcatccaggcaatgtc | 24 |
| G6Pase | acaccgactactacagcaacag | 6 | cctcgaaagatagcaagagtag | 25 |
| UCP1 | ggcattcagaggcaaatcagct | 7 | caatgaacactgccacacctc | 26 |
| Cox7a1 | gtctcccaggctctggtccg | 8 | ctgtacaggacgttgtccattc | 27 |
| Ndufb5 | tccgaagactgtcgctcctgtg | 9 | tatgttcaccagtgttatgcca | 28 |
| CKmt2 | ggtacgcactggccgaagcatc | 10 | tgatcctgctccgtcatctcag | 29 |
| H-FABP | gtcggtacctggaagctagtggac | 11 | gatctctgtgttcttgaaggtac | 30 |
| Atp5J | gttctgcagaggatcttcaggc | 12 | gtcctccagatgcctgtcgctt | 31 |
| Dio2 | cagtgtggtgcacgtctccaatc | 13 | tgaaccaaagttgaccaccag | 32 |
| UCP2 | caggtcactgtgcccttacca | 14 | cactacgttccaggatcccaa | 33 |
| 18S | agtccctgccctttgtacaca | 15 | cgatccgagggcctcacta | 34 |
| LDH2 | cactgtagtgggcgttggacaa | 16 | cggccacaattttcggagtctg | 35 |
| Cox6a1 | caacgtgttcctcaagtcgcgg | 17 | gccaggttctctttactcatc | 36 |
| NF-H | gctggacagtgagctgagaaac | 18 | caaagccaatccgacactcttc | 37 |
| NF-M | gatgagctacacgctggactcg | 19 | tgtaggaggaggacacggtgct | 38 |
| MOBP | actccaagcgtgagatcgtggac | 20 | ggacgcagctggctggtgcttg | 39 |
| ATP1a1 | tcatcgtagccaacgtgccag | 21 | gtcttgtctgagcagatggtag | 40 |

For the detection of PGC-1α protein, nuclear extracts (80 μg) prepared from brown fat were analyzed by immunoblotting using mouse polyclonal antibodies raised against purified C-terminus of PGC-1α. Muscle AMPK was detected with antibodies that recognize total AMPK (#07-181, Upstate Biotechnology™) or phosphorylated AMPK (2531, Cell Signaling Technology™). ACC phosphorylation was detected using a phospho-ACC specific antibody (3661, Cell Signaling Technology™).

Primary Hepatocytes

Primary hepatocytes were isolated following perfusion of whole liver first with perfusion buffer (Hank's Balanced Saline, HBSS) and then collagenase solution (HBSS with 1% BSA and 0.05% collagenase) for 10 minutes. Dispersed cells were resuspended and seeded onto collagen-coated plates in DMEM supplemented with 10% fetal bovine serum in the presence of 1 mM sodium pyruvate, 1 μM dexamethasone (dex) and 50 nM insulin. Two hours after plating, the medium was changed to a maintenance medium containing DMEM supplemented with 0.1% BSA and 1 μM sodium pyruvate. For hormonal treatments, hepatocytes were cultured in minimal media (DMEM with 0.1% BSA) for 40 hours and then treated with 0.2 μM or 1 μM of a combination of forskolin and dex for 3 or 6 hours before RNA isolation.

For adenoviral infection, hepatocytes were incubated with varying titers of adenovirus expressing either GFP or C/EBPβ for 3 hours and then maintained in starvation media for 24 hours. Infected cells were treated with 0.2 μM forskolin and 0.1 μM dex for 3 hours before RNA isolation.

For respiration measurements, hepatocytes were cultured in the presence of 0.2 μM dex overnight and then removed from plates by incubating with the trypsin/EDTA solution. Oxygen consumption was measured essentially as previously described (Fan, M., et al. (2004) Genes Dev 18, 278-289; Wu, Z., (1999) Cell 98, 115-124). Measurements were performed in the presence of 25 mM glucose, 1 mM pyruvate and 2% BSA.

Insulin/glucose/pyruvate Tolerance Tests

For insulin tolerance test, high-fat fed mice were fasted for 4 hours before receiving an intraperitoneal injection of insulin at 0.8 mU/kg. Plasma glucose levels were measured from tail blood before or 15, 30, 45, 60, 100 minutes after insulin infusion.

For glucose tolerance test, high-fat fed mice were fasted overnight (14 hours) and injected intraperitoneally with a glucose solution (prepared in saline) at 2 g/kg. Plasma glucose levels were measured from tail blood before or 15, 30, 45, 60, 90, 180 minutes after glucose infusion.

Pyruvate tolerance test was performed as described (Miyake, K., et al. (2002) *J Clin Invest* 110, 1483-1491). Briefly, three-month old male mice were fasted for 14 hours before receiving an intraperitoneal dose of pyruvate (in saline) at 2 g/kg. Plasma glucose levels were determined as indicated above.

Transient Transfection

Mouse H2.35 hepatoma cells (CRL-1995, ATCC) were maintained in DMEM supplemented with 4% fetal bovine serum in the presence of 0.2 µM dex. For transfection, 100 ng of reporter plasmid (Gal-C/EBPβ) was transiently transfected using Superfect™ (Qiagen™) in the presence of 500 ng of vector or pcDNA3-PGC-1α. Luciferase activity was measured 40 hours following transfection.

Example 1

Generation of PGC-1α Null Mice

Figure 1:
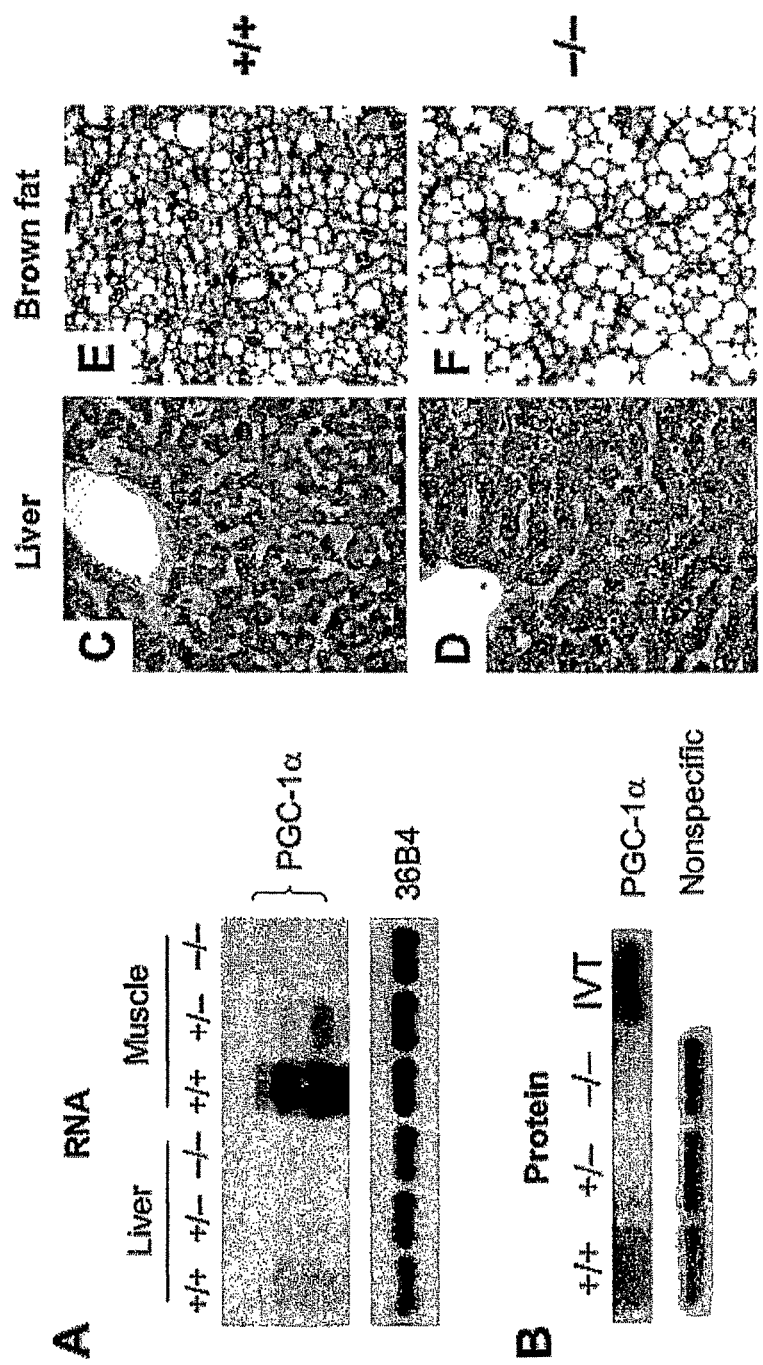
FIGS. 1A-F depict the generation of PGC-1α deficient mice. In particular.

To generate mouse strains deficient in PGC-1α by homologous recombination, a targeting plasmid was constructed flanking exons 3 to 5 of the PGC-1α gene with loxP sites (FIG. 9A). These three exons encode a highly conserved region in PGC-1α, including the LXXLL (SEQ ID NO: 47) motif that mediates its interaction with many nuclear receptors. PGC-1α$^{+/-}$ mice were generated through transgenic expression of cre recombinase under the control of ZP3 promoter, which is transiently activated during oocyte development (Lewandoski, M. et al. (1997) *Curr Biol* 7, 148-151). PGC-1α$^{-/-}$ mice were obtained from offspring of heterozygous breeding pairs. Homologous recombination and cre-mediated excision events were confirmed by hybridization and PCR analysis of genomic DNA isolated from PGC-1α$^{+/+}$, PGC-1α$^{+/-}$ and PGC-1α$^{-/-}$ mice (FIGS. 9B-D). Analysis of PGC-1α expression revealed that its mRNA was absent in skeletal muscle and liver from PGC-1α$^{-/-}$ mice and reduced to approximately 50% in PGC-1α$^{+/-}$ mice as revealed by RNA hybridization and real-time PCR analysis (FIG. 1A). As expected, no PGC-1α protein was detected in the nuclear extract prepared from PGC-1α$^{-/-}$ brown fat (FIG. 1B).

Pups lacking PGC-1α were born at the expected Mendelian ratio, suggesting that PGC-1α is dispensable for embryonic development. However, only half of PGC-1α$^{-/-}$ pups survive early postnatal period and grow into adults (Table 2).

TABLE 2

Genotypes of offspring from heterozygous breeding pairs at various stages.

| Genotype | Total | PGC-1α$^{+/+}$ | PGC-1α$^{+/-}$ | PGC-1α$^{-/-}$ |
|---|---|---|---|---|
| Day 1 pups | 73 | 17 (23%) | 38 (52%) | 18 (25%) |
| Weaning (day 21) | 464 | 135 (29%) | 264 (57%) | 65 (14%) |

PGC-1α$^{-/-}$ mice weigh approximately 10-15% less than the PGC-1α$^{+/+}$ and PGC-1α$^{+/-}$ littermates at two months of age and are fertile. Hematoxylin/eosin (H&E) staining of tissue sections revealed normal histology in several tissues including heart, skeletal muscle, pancreas and liver (FIGS. 1C-D). In contrast, PGC-1α$^{-/-}$ brown fat appeared abnormal, with abundant accumulation of large lipid droplets (FIG. 1E-F), a feature commonly associated with impaired thermogenic function. Electron microscopy studies revealed no obvious changes in the abundance and morphology of mitochondria in brown fat and liver. Measurement of plasma and liver lipid levels shows no significant difference between wild-type and PGC-1α null mice in the fed state while the triglyceride content is lower in the liver of null mice (Table 3).

TABLE 3

Plasma and liver lipids and liver glycogen content in wild type. Shown is Mean ± SEM.

| Lipids/glycogen | | PGC-1α$^{+/+}$ | PGC-1α$^{-/-}$ |
|---|---|---|---|
| Chow-fed | | | |
| Plasma triglyceride (mg/dL) | Fed | 78.6 ± 9.0 | 75.7 ± 5.4 |
| | 24-hr fasting | 75.7 ± 9.3 | 68.3 ± 9.7 |
| | 48-hr fasting | 56.4 ± 5.7 | 54.6 ± 5.9 |
| Plasma cholesterol (mg/dL) | Fed | 68.0 ± 3.8 | 65.3 ± 2.5 |
| | 24-hr fasting | 81.3 ± 3.6 | 72.1 ± 1.9 |
| Plasma free fatty acids (mM) | Fed | 0.97 ± 0.09 | 1.09 ± 0.04 |
| | 24-hr fasting | 1.77 ± 0.16 | 1.56 ± 0.06 |
| Liver triglyceride (mg/g) | Fed | 3.4 ± 0.7 | 3.8 ± 0.9 |
| | 24-hr fasting | 56.5 ± 4.1 | 34.9 ± 6.7 (p = 0.024) |
| Liver glycogen (mg/g) | Fed | 7.6 ± 0.6 | 10.3 ± 1.3 (p = 0.09) |
| | 24-hr fasting | 2.0 ± 0.2 | 2.8 ± 0.4 (p = 0.11) |
| High-fat fed | | | |
| Plasma triglyceride (mg/dL) | Fed | 94.0 ± 9.0 | 77.0 ± 8.9 |
| Plasma cholesterol (mg/dL) | Fed | 129.9 ± 8.3 | 106.2 ± 4.6 (p = 0.016) |

Example 2

PGC-1α Plays a Critical Role in Hormone-Induced Gluconeogenesis

Figure 2:
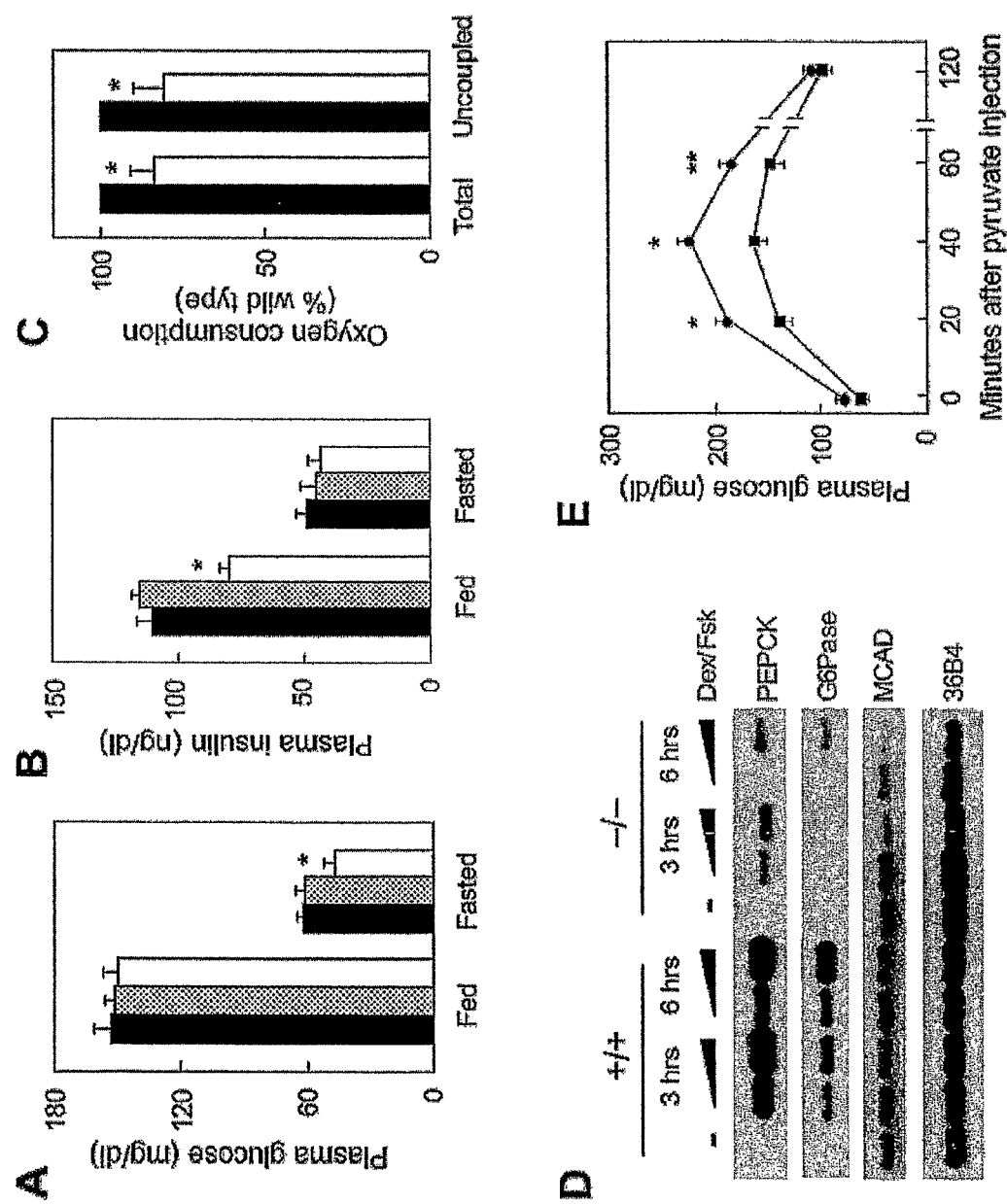
FIGS. 2A-E depict impaired glucose homeostasis and hepatic energy metabolism in the absence of PGC-1α. In particular.

PGC-1α has been shown to influence glucose metabolism in muscle and liver. The expression of PGC-1α (itself is induced in liver in response to fasting, a metabolic state characterized by active glycogenolysis, gluconeogenesis and fatty acid β-oxidation (Aoki, T. T. (1981) *Prog Clin Biol Res* 67, 161-177). To examine the requirement for PGC-1α in the regulation of glucose metabolism, measured blood glucose and insulin levels were measured in mice under various nutritional states. There is no difference in plasma glucose levels in PGC-1α$^{+/+}$, PGC-1α$^{+/-}$ and PGC-1α$^{-/-}$ mice when food is provided ad libitum (FIG. 2A). Mice deficient in PGC-1α, however, develop mild hypoglycemia after 24 hours of fasting. Examination of blood insulin levels revealed that although PGC-1α-mice are able to maintain euglycemia in the fed state, they do so with reduced circulating insulin concentrations (FIG. 2B). In contrast, no reduction in insulin levels was observed in PGC-1α$^{-/-}$ mice in the fasted state. Blood glucose levels tend to be lower in the PGC-1α$^{-/-}$ mice after prolonged fasting (48 hours) although the difference does not reach statistical significance.

PGC-1α has been shown to control the expression of genes involved in mitochondrial fatty acid β-oxidation and oxidative phosphorylation in various cell types including hepatocytes. Proper mitochondrial respiration is necessary to generate the ATP that supports the enzymatic function of the gluconeogenic pathway. To determine the effects of PGC-1α deficiency on mitochondrial respiration, an oxygen electrode was used to measure oxygen consumption in isolated hepatocytes. Total oxygen consumption rate is reduced 17% in PGC-1α$^{-/-}$ hepatocytes compared to wild-type controls (FIG. 2C). Respiration due to mitochondrial proton leak is also reduced approximately 20% in the PGC-1α deficient hepatocytes (FIG. 2C). These data illustrate that mitochondrial function is impaired in the hepatocytes from PGC-1α$^{-/-}$ mice.

Hepatic gluconeogenesis is of major importance in the fasted state (Hanson, R. W., and Reshef, L. (1997) *Annu Rev Biochem* 66, 581-611; Pilkis, S. J., and Granner, D. K. (1992) *Annu Rev Physiol* 54, 885-909) and is controlled by PGC-1α in gain of function experiments (Herzig, S., et al. (2001) *Nature* 413, 179-183; Yoon, J. C., et al. (2001) *Nature* 413, 131-138). The induction of PGC-1α and gluconeogenic genes, such as phosphoenolpyruvate carboxykinase (PEPCK) and glucose-6-phosphatase (G6Pase), are mediated by a rise in the circulating concentrations of counter-regulatory hormones, such as glucagon and glucocorticoids, and a fall in insulin levels. To determine whether PGC-1α is essential for expression of this program, primary hepatocytes were isolated from PGC-1α$^{+/+}$ and PGC-1α$^{-/-}$ mice and examined the expression of the PEPCK and G6Pase genes in response to hormonal treatments. Basal levels of PEPCK and G6Pase mRNA were similar in PGC-1α$^{+/+}$ and PGC-1α$^{-/-}$ hepatocytes, as revealed by RNA hybridization and quantitative real-time PCR analysis (FIG. 2D). Following treatments with glucocorticoid and forskolin, PGC-1α$^{+/+}$ hepatocytes exhibit a robust and dose-dependent increase in PEPCK and G6Pase mRNA (FIG. 2D). In contrast, the induction of PEPCK and G6Pase mRNA expression is greatly diminished in hepatocytes isolated from PGC-1α$^{-/-}$ mice at all treatment conditions examined. These results clearly demonstrate that PGC-1α is an essential mediator of transcriptional activation of gluconeogenic genes in response to hormonal stimulation in isolated hepatocytes.

To determine whether PGC-1α is necessary for gluconeogenesis in vivo, blood glucose levels in mice were examined following intra-peritoneal injection of pyruvate, an important substrate for this pathway. Consistent with defects in gluconeogenic gene expression and mitochondrial function in the PGC-1α$^{-/-}$ hepatocytes, mice lacking PGC-1α have greatly reduced ability to convert pyruvate into glucose compared to wild-type littermates (FIG. 2E).

Example 3

Constitutive Activation of the Hepatic Gluconeogenic Program in vivo in the Absence of PGC-1α

Figure 3:
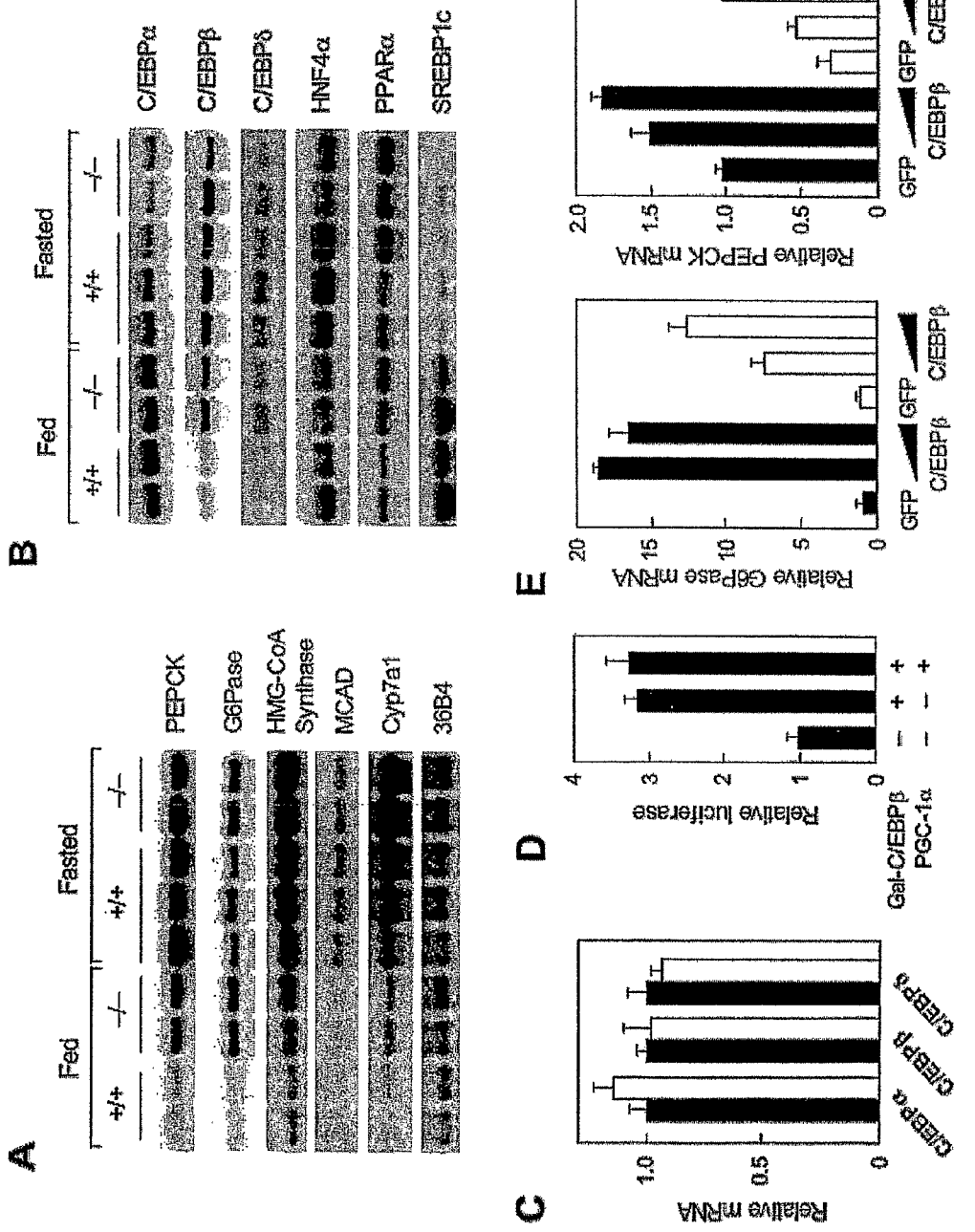
FIGS. 3A-E depict the constitutive activation of the gluconeogenic program in PGC-1α deficient liver. In particular.

The nutritional regulation of PEPCK and G6Pase genes under fed and fasted states in the mice was examined. As expected, wild-type mice activate multiple adaptive metabolic changes in response to fasting (FIG. 3A), as shown by increased expression of gluconeogenic genes and those involved in fatty acid oxidation (MCAD), ketone body synthesis (mitochondrial HMG-CoA synthase) and bile acid synthesis (Cyp7a1) (Rhee, J., et al (2003) *Proc Natl Acad Sci USA* 100, 4012-4017; Shin, D. J., et al. (2003) *J Biol Chem* 278, 50047-50052). Surprisingly, the expression of PEPCK, G6Pase, HMG-CoA synthase and MCAD is similar in PGC-1α$^{+/+}$ and PGC-1α$^{-/-}$ liver in the fasted state (FIG. 3A). More unexpectedly, the mRNA levels of PEPCK, G6Pase and HMG-CoA synthase are greatly elevated in PGC-1α$^{-/-}$ mouse liver under fed conditions (FIG. 3A). Notably, expression of G6Pase in the fed state is near the level that is usually seen in fasted liver. These results indicate that although PGC-1α is not required for the expression of gluconeogenic and ketogenic genes, this coactivator is essential for proper nutritional regulation of this response. Since basal levels of PEPCK and G6Pase expression are similar in untreated primary hepatocytes in the presence or absence of PGC-1α (FIG. 2D), this indicates that systemic signals are probably responsible for the constitutive activation of these genes under fed conditions in mice lacking PGC-1α.

The aberrant activation of PEPCK and G6Pase expression is likely due to dysregulation of one or more transcription factors that can regulate the PEPCK and G6Pase genes in the absence of PGC-1α. To assess this possibility, mRNA levels of several transcription factors known to have at least some connection with this process were examined. As shown in FIG. 3B, the expression of HNF4α and PPARα, key regulators of hepatic metabolism in the fasted state, was comparable in PGC-1α$^{+/+}$ and PGC-1α$^{-/-}$ liver in the fed state, although the induction of HNF4α in response to fasting is blunted in the absence of PGC-1α. The mRNA levels for FOXO1 and GR remain unchanged between genotypes in both fed and fasted states. As expected, the expression of sterol response element binding protein 1c (SREBP1c), a central regulator of hepatic lipogenesis (Horton, J. D., et al. (2002) *J Clin Invest* 109, 1125-1131), is suppressed in response to fasting in both PGC-1α$^{+/+}$ and PGC-1α$^{-/-}$ mice. This indicates that although the expression of gluconeogenic and ketogenic genes is dysregulated in the absence of PGC-1α, the nutritional regulation of SREBP1c is still intact. In contrast, there is a striking increase in the abundance of C/EBPβ mRNA in PGC-1α$^{-/-}$ mouse liver, precisely mirroring the aberrant expression of PEPCK and G6Pase in the fed state (FIG. 3A). C/EBPβ is normally induced in the fasted state in wild-type animals but is abnormally activated in the fed state in the null mice. C/EBPδ is also induced in the fed liver lacking PGC-1α while C/EBPα is expressed normally with respect to PGC-1α genotypes. The aberrant induction of C/EBPβ and C/EBPδ, however, is absent when PGC-1α-deficient hepatocytes are grown in cell culture, indicating that systemic signals are likely responsible for their increased expression (FIG. 3C). These results indicate that altered C/EBP transcription factor activities, particularly C/EBPβ, may play a role in the constitutive activation of gluconeogenic gene expression seen in the PGC-1α deficient mouse liver.

Example 4

PGC-1α-Independent Activation of Gluconeogenic Genes by C/EBPβ

C/EBPβ is a transcription factor that belongs to the basic leucine-zipper family and has been shown to modulate the activity of the transfected PEPCK promoter in response to gluconeogenic hormones (Croniger, C. et al. (1998) *J Biol Chem* 273, 31629-31632; Park, E. A. et al. (1993) *J Biol Chem* 268, 613-619; Roesler, W. J. (2001) *Annu Rev Nutr* 21, 141-165). Pups lacking C/EBPβ develop severe hypoglycemia and half of them died shortly after birth due to a failure to activate hepatic gluconeogenic gene expression and glucose production (Croniger, C. et al. (1997) *J Biol Chem* 272, 26306-26312; Liu, S. et al (1999) *J Clin Invest* 103, 207-213). The effects of C/EBPβ on the endogenous gluconeogenic genes have not been studied. Moreover, a functional interaction between C/EBPβ and PGC-1α has not been examined to date. As shown in FIG. 3D, PGC-1 does not coactivate C/EBPβ in transient transfection assays. Whether C/EBPβ could modulate expression of endogenous genes of gluconeogenesis and whether it could do so in the absence of PGC-1α was next examined. Primary hepatocytes were isolated from wild-type and PGC-1α deficient mice, infected with a recombinant adenovirus expressing a control GFP protein or C/EBPβ and examined for the expression of PEPCK and G6Pase. As shown in FIG. 3E, adenoviral mediated expression of C/EBPβ activates the transcription of the G6Pase gene approximately 17-fold in wild-type hepatocytes. PEPCK mRNA level is also elevated 1.8-fold in response to ectopic C/EBPβ expression. Importantly, induction of gluconeogenic gene expression by C/EBPβ was also observed in the PGC-1α$^{-/-}$ cells with a 12-fold increase in G6Pase mRNA and approximately 3-fold induction of PEPCK mRNA. The absolute levels of these mRNAs are somewhat higher in hepatocytes with an intact PGC-1α gene. These results demonstrate that C/EBPβ is able to turn on gluconeogenic gene expression in a PGC-1α-independent manner and indicate that elevated C/EBPβ in PGC-1α$^{-/-}$ animals may be at least partially responsible for the inappropriate activation of those gluconeogenic genes in the fed state.

Example 5

PGC-1α—Mice are Resistant to Diet-induced Obesity

Figure 4:
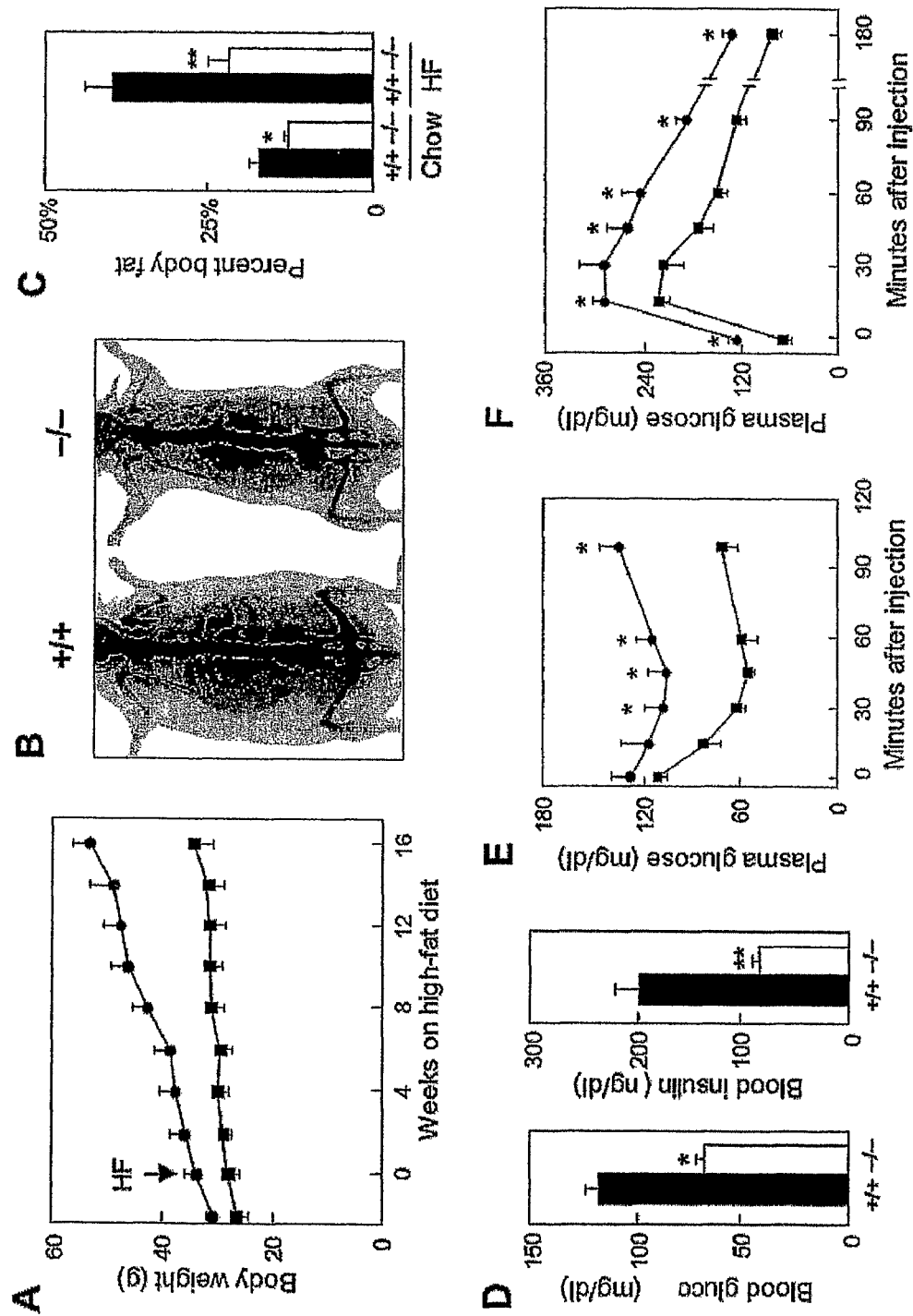
FIGS. 4A-F depict resistance to diet-induced obesity and insulin resistance in PGC-1α$^{-/-}$ mice.

The well-established role of PGC-1α in stimulating mitochondrial respiration, as well as the reduction of respiration in PGC-1α deficient hepatocytes (FIG. 2C) and abnormal brown fat morphology (FIG. 1D) all suggest that the null mice may be prone to the development of obesity due to reduced energy expenditure. To critically assess this, the animals were fed a high-fat diet containing 58% of calories derived from fat. As shown in FIG. 4A, and as expected, wild-type mice gain substantial body weight throughout the course of high-fat feeding. In contrast, PGC-1α$^{-/-}$ mice are surprisingly resistant to diet-induced obesity (FIG. 4A). Analysis of body fat content using a dual energy X-ray absorptiometry (DEXA) scanner revealed that PGC-1α$^{-/-}$ mice are remarkably leaner (22.6±2.4% body fat, n=6) than the PGC-1α$^{+/+}$ controls (39.8±2.8% body fat, n=5) after 16 weeks of high-fat feeding (FIGS. 4B-C). In fact, a small but significant decrease in body fat content was observed in PGC-1α$^{-/-}$ mice fed a chow diet (FIG. 4C). As expected from their obesity, high-fat fed PGC-1α$^{+/+}$ mice developed insulin resistance as indicated by elevated fasting glucose and insulin concentrations and in vivo insulin tolerance test (FIGS. 4D-E). PGC-1α$^{-/-}$ mice, however, display significantly enhanced insulin sensitivity and improved glycemic control in a glucose tolerance test (FIGS. 4E-F) compared to the control mice. Similar results were seen in PGC-1α$^{-/-}$ mice when maintained on a normal rodent chow. These data clearly indicate that PGC-1α null mice are resistant to obesity caused by high-fat feeding and are protected from developing insulin resistance and glucose intolerance that ordinarily accompanies this obesity.

Figure 5:
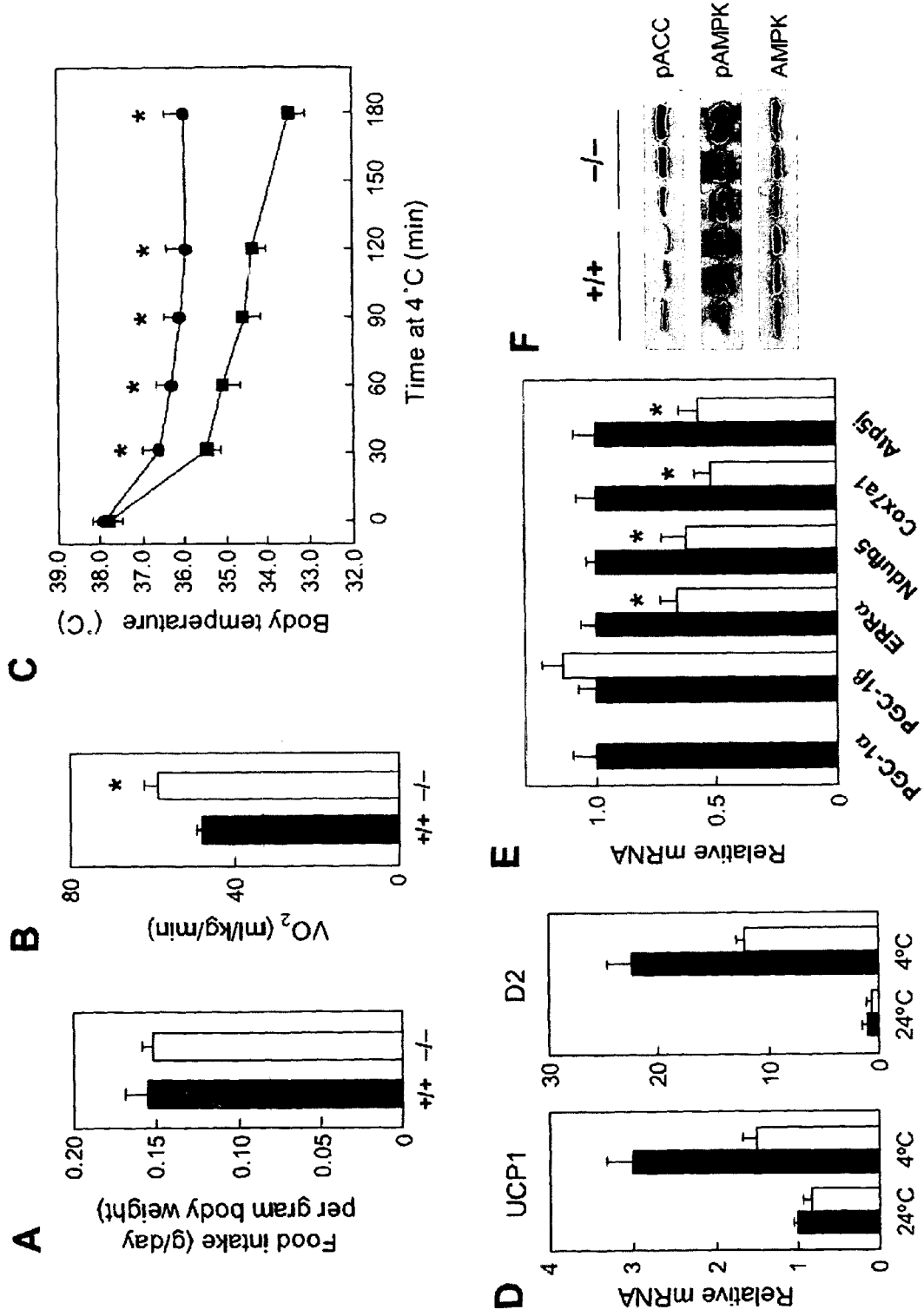
FIGS. 5A-F are graphs depicting analysis of whole-body energy balance and thermogenesis in PGC-1α$^{-/-}$ mice.

The two major arms of energy balance were also examined: energy intake as measured by food intake and energy expenditure. Both PGC-1α$^{+/+}$ and PGC-1α$^{-/-}$ mice show similar food intake at various time points during postnatal development and high-fat feeding (FIG. 5A). In contrast, energy expenditure, measured as $O_2$ consumption, is approximately 23% higher in PGC-1α$^{-/-}$ mice throughout a three-day period of metabolic monitoring (FIG. 5B). Thus, the resistance to diet-induced obesity in PGC-1α$^{-/-}$ mice correlates with a substantial increase in energy expenditure.

Example 6

Reduced Thermogenic Capacity and Hyperactivity in PGC-1α$^{-/-}$ Mice

Two key components of energy expenditure are adaptive thermogenesis and physical activity. To determine whether increased oxygen consumption in PGC-1α$^{-/-}$ mice is due to enhanced thermogenesis, the thermogenic capacity of these animals was examined with a standard cold challenge. Resting body temperature is similar between PGC-1α$^{+/+}$ and PGC-1α$^{-/-}$ mice (FIG. 5C, t=0). 6-week old mice were exposed to 4° C. and their core body temperature monitored. Both PGC-1α$^{+/+}$ and PGC-1α$^{-/-}$ mice respond to cold temperature by increasing frequency of shivering. In contrast to wild-type littermates, which are able to keep body temperature around 36.5° C. after an initial drop of approximately 1.5° C., PGC-1α$^{-/-}$ mice display striking sensitivity to the cold temperature (FIG. 5C). Body temperature of PGC-1α$^{-/-}$ mice drops to 33.5° C. within 3 hours and the hypothermia becomes lethal if the exposure of the null mice is extended beyond 6 hours. Defense of body temperature in mice is mainly the function of brown adipose tissue, which generates heat due in large part to abundant expression of the mitochondrial uncoupler, UCP1 (Bouillaud, F. et al. (1985) *Proc Natl Acad Sci USA* 82, 445-448; Jacobsson, A., et al. (1985) *J Biol Chem* 260, 16250-16254). Analysis of brown fat gene expression revealed that the induction of UCP1 in the null mice was reduced to approximately 45% of the wild-type level while the induction of type 2 iodothyronine deiodinase (D2) mRNA was reduced nearly 50% in PGC-1α$^{-/-}$ mice compared to controls (FIG. 5D). The expression of PGC-1β is unchanged while mRNAs encoding several enzymes involved in mitochondrial electron transport and fatty acid oxidation are reduced in PGC-1α$^{-/-}$ brown fat. These data indicate that the increased energy expenditure in the PGC-1α$^{-/-}$ mice is not due to increased thermogenesis in these animals; on the contrary, the mice are hypothermic when challenged.

Skeletal muscle is a major tissue involved in energy expenditure in vivo. To determine whether PGC-1α is also required for normal mitochondrial function in skeletal muscle, mitochondrial gene expression in quadriceps muscle from wild-type and PGC-1α null mice was examined. mRNA levels for a large number of genes involved in fatty acid oxidation and mitochondrial function are reduced 30-60% in PGC-1α$^{-/-}$ mice, including those involved in intracellular fatty acid trafficking, the Krebs Cycle, electron transport (Ndufb5 and Cox7a1), ATP synthesis (Atp5j) and mitochondrial protein translation (FIG. 5E). Interestingly, the expression of ERRα, a direct target of PGC-1α and an important mediator of PGC-1α action, is also reduced in the absence of PGC-1α while PGC-1β RNA level remains largely unchanged (FIG. 5E).

Impaired mitochondrial energy metabolism might be expected to negatively affect ATP/AMP ratios. Consistent with this, AMP-activated protein kinase (AMPK), a key component of cellular energy-sensing pathways (Carling, D. (2004) *Trends Biochem Sci* 29, 18-24), is strongly activated in PGC-1α deficient skeletal muscle. The levels of phosphorylated AMPK and acetyl-CoA carboxylase (ACC), a known substrate for activated AMPK, are significantly increased in PGC-1α$^{-/-}$ muscle (FIG. 5F). These data clearly indicate that PGC-1α is essential for normal mitochondrial gene expression and energy metabolism in skeletal muscle.

Figure 6:
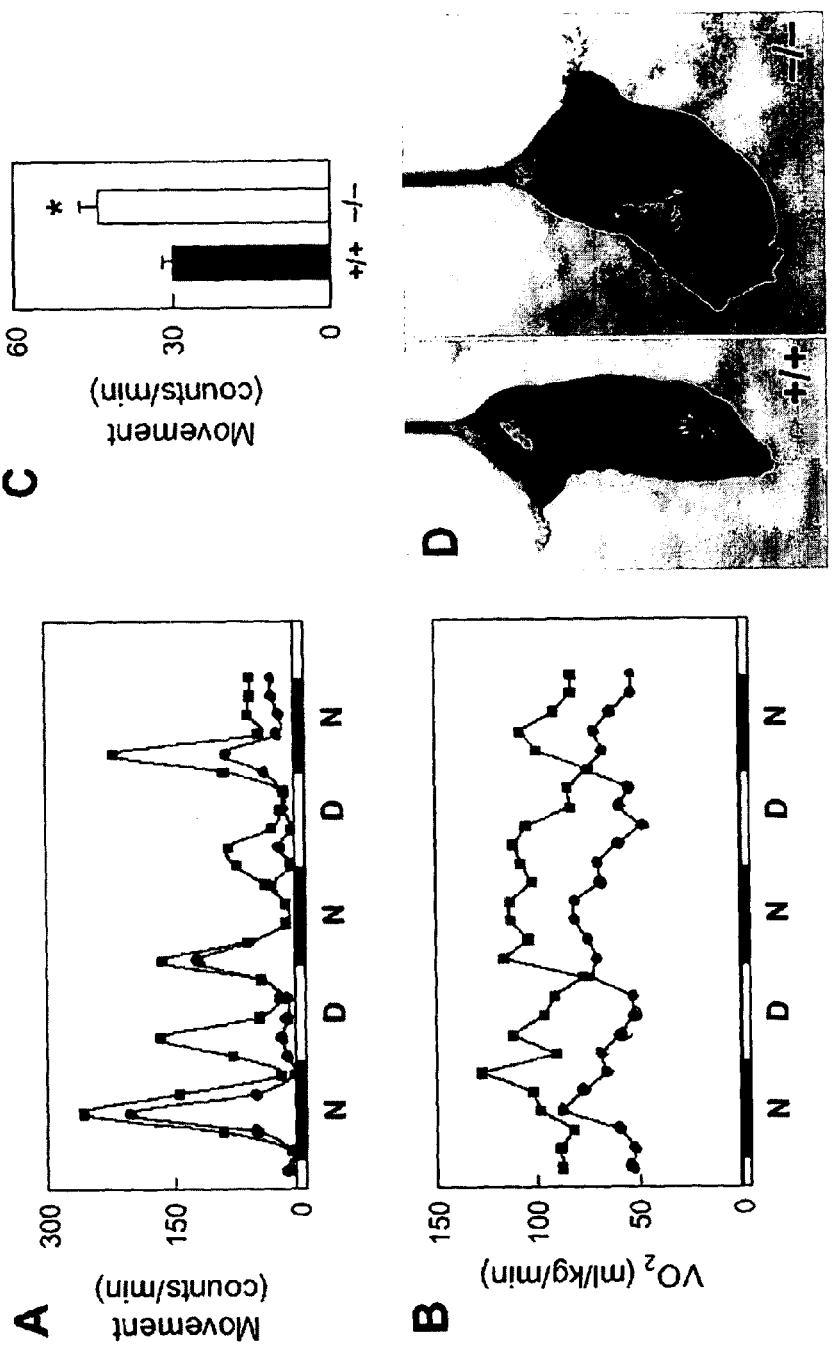
FIGS. 6A-D depict hyperactivity and limb clasping in PGC-1α$^{-/-}$ mice.

The lack of an increase in thermogenesis or mitochondrial gene expression in the mutant animals suggested that the higher metabolic rate in PGC-1α deficient mice might be caused by altered levels of physical activity. To assess this, the frequency of animal movements was monitored and quantitated using the Comprehensive Lab Animal Monitoring System (CLAMS), which is capable of simultaneously recording whole body oxygen consumption and physical activity. As shown in FIGS. 6A-B, a higher oxygen consumption rate in PGC-1α$^{-/-}$ mice is accompanied by profound hyperactivity as indicated by increased physical movement. PGC-1α deficient mice are hypermetabolic and hyperactive compared to wild-type controls both during daytime and at night. In fact, the PGC-1α null mice displayed a 40% increase in the frequency of random movements during the monitoring period (FIG. 6C). These results strongly indicate that the increase in energy expenditure seen in PGC-1α$^{-/-}$ mice is due to the hyperactivity displayed by the null animals.

Example 7

Striatal Degeneration in PGC-1α Null Mouse Brain

Hyperactivity in PGC-1α$^{-/-}$ mice could result from altered circulating hormones and/or signals that originated from the central nervous system. Measurements of several hormones known to influence animal movement, including thyroid hormone and catecholamines, showed no significant alterations (Table 4).

TABLE 4

Concentrations of circulating hormones in wild type and PGC-1α null mice.

| Hormones | PGC-1α$^{+/+}$ | PGC-1α$^{-/-}$ |
|---|---|---|
| Triiodothyronine (ng/ml) | 0.43 ± 0.06 | 0.44 ± 0.04 (n.s.) |
| Leptin (ng/ml) | 0.86 ± 0.22 | 0.25 ± 0.09 (p = 0.01) |
| Glucagon (pg/ml) | 61 ± 23 | 52 ± 14 (n.s.) |
| Corticosterone (ng/ml) | 231 ± 35 | 196 ± 27 (n.s.) |
| Epinephrine (pg/ml) | 485 ± 144 | 768 ± 304 (n.s.) |
| Norepinephrine (pg/ml) | 1484 ± 280 | 1042 ± 291 (n.s.) |

Besides a simple increase in total movement, it was observed that PGC-1α null mice display behavioral changes that are characteristic of certain neurological disorders, including stimulus-induced myoclonus, exaggerated startle responses, dystonic posturing and frequent limb clasping (FIG. 6D). These findings are consistent with lesions in the striatum, the brain area that is affected in certain neurological diseases characterized by disorders of movement, including Huntington's disease.

Figure 7:
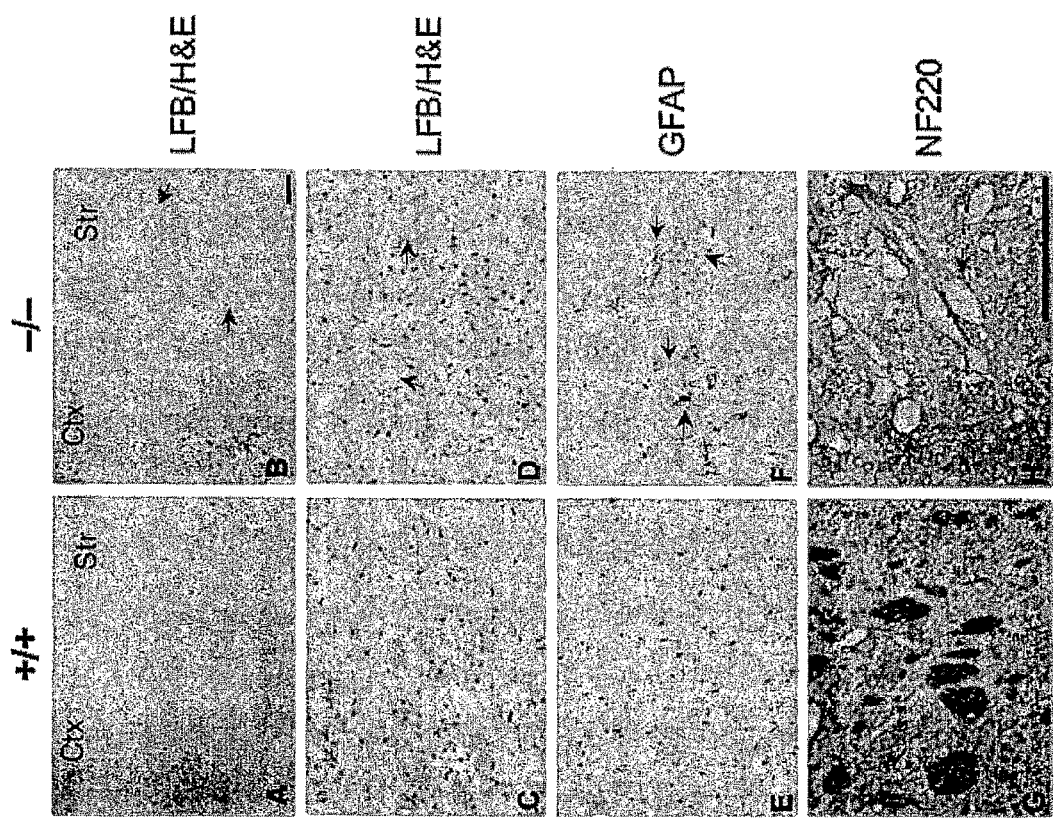
FIGS. 7A-H depict the results of histological staining of brain sections from wild type and PGC-1α null mice.

Neuropathology in the PGC-1α$^{-/-}$ mouse brain was assessed by histological analysis. The overall brain anatomy appeared similar in the PGC-1α$^{+/+}$ and PGC-1α mice. However, a striking spongiform pattern of lesions was found predominantly in the striatum of three-month old PGC-1α$^{-/-}$ mice (FIG. 7). The number and size of lesions decrease from the dorsal to the ventral side and also from the lateral to the medial parts of the striatum. Occasionally, much smaller and less abundant lesions were also found in the cortex, especially in cortical layer V/VI of the motor cortex, nucleus accumbens, thalamus, substantia nigra, hippocampus and the mammalliary body. The spongiform lesions in the striatum and brain stem were associated with gliosis, as indicated by strong immunoreactivity for glial fibrillary associated protein (GFAP), a hallmark for reactive astrocytes (FIGS. 7E-F). No reactive astrocytes were found in the minor lesions in other brain areas. To determine if the lesions were mainly affecting the white matter, brain sections of PGC-1α$^{+/+}$ and PGC-1α$^{-/-}$ mice were stained with Luxol fast blue for myelin.

As seen in FIGS. 7A-D, lesions are predominantly associated with the white matter and rarely with the grey matter. The overall neuronal density appeared similar in wild-type mice and PGC-1α null mice, although neurons containing vacuoles in PGC-1α$^{-/-}$ mouse brain were occasionally observed. Immunostaining using a neurofilament-heavy chain (NF220) antibody showed that striatal neurons have lost NF220-positive neurites in the absence of PGC-1α (FIGS. 7G-H). In fact, the spongiform lesions appear to arise from the loss of axons in the striatal area in PGC-1α$^{-/-}$ mouse brain. These results clearly demonstrate that PGC-1α is required for normal brain function and that loss of PGC-1α leads to neuronal degeneration in specific brain areas, most prominently in the striatum.

PGC-1α has been shown to regulate oxidative metabolism and biological programs associated with increased oxidative capacity in a tissue-specific manner. Analysis of gene expression in the brains of wild-type and mutant mice by real-time PCR revealed that mRNA levels of many mitochondrial genes are reduced in mutants (FIG. 8A).

Figure 8:
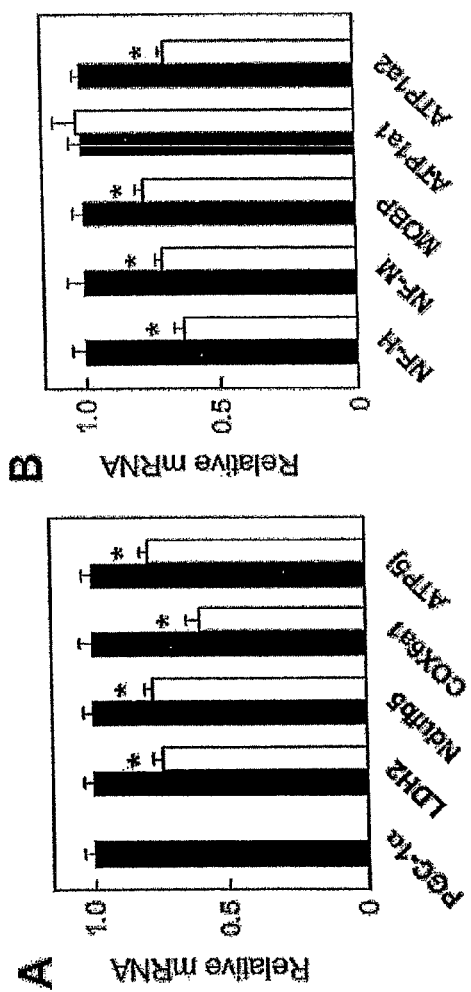
FIGS. 8 A-B depict gene expression analysis in mouse brain and neurite growth in cultured primary striatal neurons.

Interestingly, the expression of several brain-specific genes not involving mitochondrial function, including those encoding neurofilament proteins (NF-H and NF-M), myelin-associated oligodendrocyte basic protein (MOBP) and Na$^+$/K$^+$ ATPase (ATP1a2) is also significantly reduced in the PGC-1α null brain compared to wild-type controls (FIG. 8B). In contrast, mRNA encoding another sodium pump subunit, ATP1a1, is not altered. These results indicate that, in addition to its key role in the regulation of mitochondrial gene expression, PGC-1α may also have important function in the control of neuronal gene expression and function. In fact, primary striatal neurons isolated from PGC-1α$^{-/-}$ mouse embryos display a severe impairment in neurite growth. Striatal neurons lacking PGC-1α have greatly reduced branches of neurites whereas wild-type neurons exhibit robust neurite outgrowth and form an extensive network in culture.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for treating Huntington's disease in a subject comprising the step of administering to said subject a peroxisome proliferator-activated receptor gamma coactivator 1 alpha (PGC-1α) polypeptide comprising the amino acid sequence of SEQ ID NO:2 such that the Huntington's disease is treated.

2. The method of claim 1, wherein the PGC-1α polypeptide further comprises a heterologous polypeptide.

3. A method for treating Huntington's disease in a subject, comprising the step of administering to said subject a PGC-1α polypeptide comprising an amino acid sequence which is at least 90 percent identical to the amino acid sequence of SEQ ID NO: 2, which has an LXXLL motif of the amino acid sequence of SEQ ID NO: 47, and which maintains the ability to modulate one or more of the following biological activities: mitochondrial function; the activity or expression of a mitochondrial gone selected from the group consisting of LDH2, Ndufb5, COX6a1, and ATP5j; the activity or expression of a neuronal gene selected from the group consisting of NF-H, NF-M, MOBP, ATPα1, and ATP1α2; lesion formation; neurite formation; neurite growth; neuronal degeneration; body weight: energy expenditure; gluconeogenesis; and interaction with nuclear hormone receptors, such that the Huntington's disease is treated.

4. The method of claim 1 or 3, wherein the PGC-1α polypeptide is administered in a pharmaceutically acceptable formulation.

5. The method of claim 1 or 3, wherein the PGC-1α polypeptide modulates mitochondrial function.

6. The method of claim 5, wherein mitochondrial function is modulated in the brain.

7. The method of claim 1 or 3, wherein the PGC-1α polypeptide modulates lesion formation in the brain.

8. The method of claim 1 or 3, wherein the PGC-1α polypeptide modulates neurite growth.

* * * * *